(12) United States Patent
Rajagopalan et al.

(10) Patent No.: US 12,127,785 B2
(45) Date of Patent: Oct. 29, 2024

(54) METHODS AND SYSTEMS FOR TREATING DIABETES AND RELATED DISEASES AND DISORDERS

(71) Applicant: Fractyl Health, Inc., Burlington, MA (US)

(72) Inventors: Harith Rajagopalan, Wellesley Hills, MA (US); Jay Caplan, Belmont, MA (US); Craig M. Gardner, Belmont, MA (US); J. Christopher Flaherty, Auburndale, FL (US)

(73) Assignee: Fractyl Health, Inc., Lexington, MA (US)

( * ) Notice: Subject to any disclaimer, the term of this patent is extended or adjusted under 35 U.S.C. 154(b) by 824 days.

(21) Appl. No.: 17/096,855

(22) Filed: Nov. 12, 2020

(65) Prior Publication Data
US 2021/0307816 A1 Oct. 7, 2021

Related U.S. Application Data

(63) Continuation of application No. 15/406,572, filed on Jan. 13, 2017, now Pat. No. 10,869,718, which is a
(Continued)

(51) Int. Cl.
*A61B 18/14* (2006.01)
*A61B 18/04* (2006.01)
(Continued)

(52) U.S. Cl.
CPC .......... *A61B 18/1492* (2013.01); *A61B 18/04* (2013.01); *A61B 18/06* (2013.01);
(Continued)

(58) Field of Classification Search
CPC ..... A61B 18/1492; A61B 18/04; A61B 18/06; A61B 2018/00029; A61B 2018/00196;
(Continued)

(56) References Cited

U.S. PATENT DOCUMENTS 5,084,044 A 1/1992 Quint
5,190,540 A 3/1993 Lee
(Continued)

FOREIGN PATENT DOCUMENTS

CA 2666661 C 1/2015
CN 1771888 A 5/2006
(Continued)

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
(Continued)

*Primary Examiner* — Amber R Stiles
(74) *Attorney, Agent, or Firm* — Wilson Sonsini Goodrich & Rosati

(57) ABSTRACT

Systems, device and methods treat target tissue to provide a therapeutic benefit to the patient. A tissue treatment device comprises a tissue treatment element constructed and arranged to treat target tissue, such as duodenal mucosa tissue.

18 Claims, 16 Drawing Sheets

Related U.S. Application Data continuation of application No. PCT/US2015/040775, filed on Jul. 16, 2015.

(60) Provisional application No. 62/025,307, filed on Jul. 16, 2014.

(51) Int. Cl.
  *A61B 18/06* (2006.01)
  *A61M 29/02* (2006.01)
  *A61B 18/00* (2006.01)
  *A61M 25/00* (2006.01)
  *A61M 25/10* (2013.01)

(52) U.S. Cl.
  CPC ... *A61M 29/02* (2013.01); *A61B 2018/00029* (2013.01); *A61B 2018/00196* (2013.01); *A61B 2018/0022* (2013.01); *A61B 2018/00238* (2013.01); *A61B 2018/00404* (2013.01); *A61B 2018/0041* (2013.01); *A61B 2018/00494* (2013.01); *A61B 2018/00577* (2013.01); *A61B 2018/00779* (2013.01); *A61B 2018/00797* (2013.01); *A61B 2018/00839* (2013.01); *A61B 2018/00875* (2013.01); *A61B 2018/00994* (2013.01); *A61B 2018/044* (2013.01); *A61B 2018/1467* (2013.01); *A61M 2025/0087* (2013.01); *A61M 2025/1052* (2013.01)

(58) Field of Classification Search
  CPC .. A61B 2018/0022; A61B 2018/00238; A61B 2018/00404; A61B 2018/0041; A61B 2018/00494; A61B 2018/00577; A61B 2018/00779; A61B 2018/00797; A61B 2018/00839; A61B 2018/00875; A61B 2018/00994; A61B 2018/044; A61B 2018/1467; A61M 29/02; A61M 2025/0087; A61M 2025/1052
  See application file for complete search history.

(56) References Cited

U.S. PATENT DOCUMENTS

| | | | |
|---|---|---|---|
| 5,423,754 A | 6/1995 | Cornelius et al. |
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,869,037 A | 2/1999 | Crystal et al. |
| 5,871,525 A | 2/1999 | Edwards et al. |
| 5,879,347 A | 3/1999 | Saadat et al. |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards et al. |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | Mcguckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,486,005 B2 | 7/2013 | Yodfat et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,757,535 B2 | 9/2017 | Rajagopalan et al. |
| 9,844,641 B2 | 12/2017 | Rajagopalan et al. |
| 10,232,143 B2 | 3/2019 | Rajagopalan et al. |
| 10,299,857 B2 | 5/2019 | Rajagopalan et al. |
| 10,349,998 B2 | 7/2019 | Levin et al. |
| 10,610,663 B2 | 4/2020 | Rajagopalan et al. |
| 10,765,474 B2 | 9/2020 | Kadamus et al. |
| 10,864,352 B2 | 12/2020 | Rajagopalan et al. |
| 10,869,718 B2 | 12/2020 | Rajagopalan et al. |
| 11,185,367 B2 | 11/2021 | Rajagopalan et al. |
| 11,419,659 B2 | 8/2022 | Levin et al. |
| 11,439,457 B2 | 9/2022 | Caplan et al. |
| 2002/0013581 A1 | 1/2002 | Edwards et al. |
| 2002/0077594 A1 | 6/2002 | Chien et al. |
| 2002/0115992 A1 | 8/2002 | Utley et al. |
| 2002/0192162 A1 | 12/2002 | Green |
| 2003/0040804 A1 | 2/2003 | Stack et al. |
| 2003/0093072 A1 | 5/2003 | Friedman |
| 2003/0153905 A1 | 8/2003 | Edwards et al. |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1 | 7/2004 | Callister |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |

(56) References Cited

U.S. PATENT DOCUMENTS

| | | |
|---|---|---|
| 2004/0220559 A1 | 11/2004 | Kramer et al. |
| 2005/0096638 A1 | 5/2005 | Starkebaum et al. |
| 2005/0154386 A1 | 7/2005 | West et al. |
| 2005/0165437 A1 | 7/2005 | Takimoto |
| 2005/0171524 A1 | 8/2005 | Stern et al. |
| 2005/0192652 A1 | 9/2005 | Cioanta et al. |
| 2005/0203489 A1 | 9/2005 | Saadat et al. |
| 2005/0222558 A1 | 10/2005 | Baxter et al. |
| 2005/0245943 A1 | 11/2005 | Zvuloni et al. |
| 2005/0251116 A1 | 11/2005 | Steinke et al. |
| 2005/0273090 A1 | 12/2005 | Nieman et al. |
| 2006/0070631 A1 | 4/2006 | Scopton et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0247683 A1 | 11/2006 | Danek et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van Der Weide et al. |
| 2008/0207994 A1 | 8/2008 | Gonon |
| 2008/0243112 A1 | 10/2008 | De Neve |
| 2008/0275445 A1 | 11/2008 | Kelly et al. |
| 2008/0319504 A1 | 12/2008 | Loushin et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018604 A1 | 1/2009 | Mitelberg et al. |
| 2009/0048593 A1 | 2/2009 | Ganz et al. |
| 2009/0062836 A1* | 3/2009 | Kurrus ............ A61B 17/12186 606/195 |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0208175 A1 | 8/2011 | Sobotka et al. |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0238554 A1 | 9/2012 | Cowen |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0190675 A1 | 7/2013 | Sandoski |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0310200 A1 | 10/2016 | Wang |
| 2016/0354144 A1 | 12/2016 | Caplan et al. |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |
| 2018/0193078 A1 | 7/2018 | Rajagopalan et al. |
| 2018/0193590 A1 | 7/2018 | Rajagopalan et al. |
| 2018/0221622 A1 | 8/2018 | Rajagopalan et al. |
| 2020/0060758 A1 | 2/2020 | Rajagopalan et al. |
| 2020/0060942 A1 | 2/2020 | Rajagopalan et al. |
| 2020/0138505 A1 | 5/2020 | Levin et al. |
| 2020/0155217 A1 | 5/2020 | Morneau et al. |
| 2020/0261144 A1 | 8/2020 | Caplan et al. |
| 2020/0305972 A1 | 10/2020 | Kadamus et al. |
| 2020/0405388 A1 | 12/2020 | Rajagopalan et al. |
| 2021/0008336 A1 | 1/2021 | Rajagopalan et al. |
| 2021/0196341 A1 | 7/2021 | Rajagopalan et al. |
| 2022/0117658 A1 | 4/2022 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9418896 A1 | 9/1994 |
| WO | WO-9912489 A2 | 3/1999 |
| WO | WO-0207628 A2 | 1/2002 |
| WO | WO-02058577 A1 | 8/2002 |
| WO | WO-02096327 A2 | 12/2002 |
| WO | WO-02102453 A2 | 12/2002 |
| WO | WO-03033045 A2 | 4/2003 |
| WO | WO-03092609 A2 | 11/2003 |
| WO | WO-2004064600 A2 | 8/2004 |
| WO | WO-2006020370 A2 | 2/2006 |
| WO | WO-2007044244 A2 | 4/2007 |
| WO | WO-2007067919 A2 | 6/2007 |
| WO | WO-2008002654 A2 | 1/2008 |
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO-2014055997 A1 | 4/2014 |
| WO | WO-2014070136 A1 | 5/2014 |
| WO | WO-2014197632 A2 | 12/2014 |

(56) References Cited

FOREIGN PATENT DOCUMENTS

| WO | WO-2015038973 A1 | 3/2015 |
|---|---|---|
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |
| WO | WO-2019018362 A1 | 1/2019 |
| WO | WO-2019136240 A1 | 7/2019 |
| WO | WO-2020072506 A1 | 4/2020 |
| WO | WO-2020205844 A1 | 10/2020 |
| WO | WO-2021081072 A1 | 4/2021 |
| WO | WO-2021146190 A1 | 7/2021 |
| WO | WO-2021146535 A1 | 7/2021 |

OTHER PUBLICATIONS

Araki, et al. Oral glucose-stimulated serum C-peptide predicts successful switching from insulin therapy to liraglutide monotherapy in Japanese patients with type 2 diabetes and renal impairment. Journal of diabetes investigation 5.4 (2014): 435-441.
Bruinstroop, et al. Retrospective Analysis of an Insulin-to-Liraglutide Switch in Patients with Type 2 Diabetes Mellitus. Diabetes Therapy 9.3 (2018): 1369-1375.
Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Co-pending U.S. Appl. No. 16/905,274, inventors Rajagopalan; Harith et al., filed on Jun. 18, 2020.
Co-pending U.S. Appl. No. 17/095,108, inventors Rajagopalan; Harith et al., filed on Nov. 11, 2020.
Co-pending U.S. Appl. No. 17/110,720, inventors J.; Kadamus Christopher J. et al., filed on Dec. 3, 2020.
Co-pending U.S. Appl. No. 17/181,969, inventors Rajagopalan; Harith et al., filed on Feb. 22, 2021.
Co-pending U.S. Appl. No. 17/189,772, inventors Rajagopalan; Harith et al., filed on Mar. 2, 2021.
Davis, et al. Exploring the substitution of exenatide for insulin in patients with type 2 diabetes treated with insulin in combination with oral antidiabetes agents.Diabetes care 30.11 (2007): 2767-2772.
EP12736438.8 The Extended European Search Report dated Nov. 22, 2016.
EP14844285.8 The Extended European Search Report dated Apr. 25, 2017.
EP20150391.9 The Extended European Search Report dated Aug. 20, 2020.
EP20159816.6 The Extended European Search Report dated Aug. 17, 2020.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Grikscheit, et al. Tissue-engineered small intestine improves recovery after massive small bowel resection. Ann Surg., 2004, 240:748-754.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
"International search report and written opinion dated Oct. 23, 2015 for PCT/US2015/040775.".
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
International search report with written opinion dated Jan. 9, 2018 for PCT/US2017/061074.
Kawata, et al. Is a switch from insulin therapy to liraglutide possible in Japanese type 2 diabetes mellitus patients?Journal of clinical medicine research 6.2 (2014): 138-144.
Kozawa, et al. Liraglutide is effective in type 2 diabetic patients with sustained endogenous insulin-secreting capacity.Journal of diabetes investigation 3.3 (2012): 294-297.
Miyawaki, et al. Inhibition of gastric inhibitory polypeptide signaling prevents obesity. Nat Med. Jul. 2002;8(7):738-42. Epub Jun. 17, 2002.
Nambu, et al. Liraglutide administration in type 2 diabetic patients who either received no previous treatment or were treated with an oral hypoglycemic agent showed greater efficacy than that in patients switching from insulin.Journal of diabetes investigation 4.1 (2013): 69-77.
Notice of Allowance dated Jul. 7, 2017 for U.S. Appl. No. 15/274,764.
Notice of Allowance dated Sep. 14, 2017 for U.S. Appl. No. 15/274,809.
"Office Action date Jul. 11, 2018 for U.S. Appl. No. 14/917,243.".
"Office Action date Aug. 9, 2018 for U.S. Appl. No. 14/673,565.".
Office Action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office action dated Mar. 7, 2019 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 16, 2019 for U.S. Appl. No. 14/515,324.
Office action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.

(56) References Cited

OTHER PUBLICATIONS

Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
"Office action dated Sep. 7, 2018 for U.S. Appl. No. 14/609,332.".
Office Action dated Sep. 23, 2016 for U.S. Appl. No. 14/515,324.
"Office action dated Oct. 4, 2018 for U.S. Appl. No. 14/515,324.".
Office Action dated Oct. 7, 2016 for U.S. Appl. No. 13/945,138.
Office Action dated Nov. 2, 2017 for U.S. Appl. No. 15/156,585.
"Office action dated Nov. 2, 2018 for U.S. Appl. No. 14/609,334".
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
Office action dated Dec. 17, 2015 for U.S. Appl. No. 14/515,324.
Office action dated Dec. 18, 2017 for U.S. Appl. No. 14/515,324.
"Office action dated Dec. 18, 2018 for U.S. Appl. No. 14/470,503.".
Office action dated Dec. 19, 2017 for U.S. Appl. No. 13/945,138.
PCT/US14/66829 International Search Report dated Feb. 20, 2015.
PCT/US2018/042438 International Search Report dated Sep. 14, 2018.
PCT/US2019/012338 International Search Report dated Apr. 15, 2019.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.
Tomizawa, et al. Clinical Outcome of Endoscopic Mucosal Resection (EMR) of Sporadic, Non-Ampullary Duodenal Adenoma (SNADA): Predictor Analysis of Safety and Efficacy From a High vol. U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
U.S. Appl. No. 14/917,243 Office Action dated Jun. 5, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 17/110,720 Office Action dated Feb. 2, 2021.
U.S. Appl. No. 13/945,138 Office Action dated Dec. 10, 2019.
U.S. Appl. No. 14/470,503 Notice of Allowance dated Feb. 27, 2019.
U.S. Appl. No. 14/515,324 Office Action dated Mar. 31, 2020.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Usui, et al. Retrospective analysis of safety and efficacy of insulin-to-liraglutide switch in Japanese type 2 diabetes: a caution against inappropriate use in patients with reduced β-cell function.Journal of diabetes investigation 4.6 (2013): 585-594.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. April 2017vol. 152, Issue 5, Supplement 1, p. S825. DOI: http://dx.doi.org/10.1016/S0016-5085(17)32851-2.
U.S. Appl. No. 17/189,772 Office Action dated May 26, 2021.
Colagiuri et al., Are Lower Fasting Plasma Glucose Levels at Diagnosis of Type 2 Diabetes Associated With Improved Outcomes? Diabetes Care, vol. 25, No. 9, Aug. 2002; pp. 1410-1417.
RD White. Insulin Dosing: How High Can You Go? Accessible on the world wide web at https://www.patientcareonline.com/view/insulin-dosing-how-high-can-you-go Feb. 10, 2010. Accessed May 19, 2021.
U.S. Appl. No. 17/189,772 Notice of Allowance dated Aug. 4, 2021.
U.S. Appl. No. 17/516,503 Office Action dated Nov. 27, 2023.

* cited by examiner

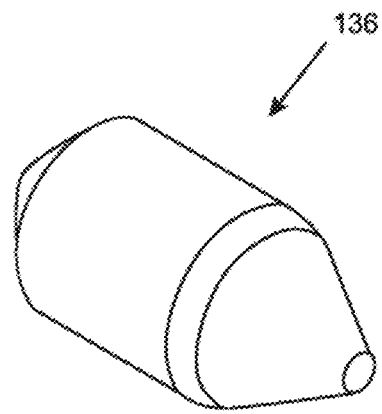
FIG 4A
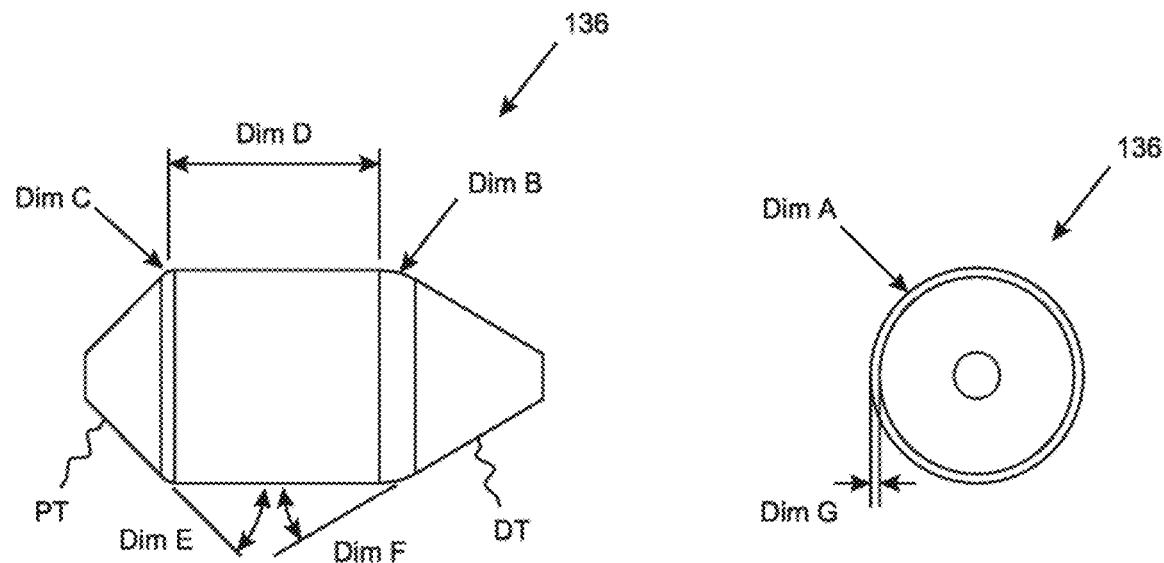
FIG 4B
FIG 4C

| Number of Duodenal Ablations | Number of Patients |
|---|---|
| 0 | 2 |
| 1 | 6 |
| 2 | 4 |
| 3 | 22 |
| 4 | 0 |
| 5 | 1 |

FIG. 7

| Characteristic | Value (N=32) | N in calc |
|---|---|---|
| Duration diabetes - yr | 5.1 +/- 2.9 | 27 |
| Age - yr | 52.9 +/- 7.6 | 26 |
| Female sex - N (%) | 12 (46.2) | 26 |
| Weight - kg | 86.7 +/- 13.2 | 26 |
| Height - cm | 165.7 +/- 10.2 | 26 |
| BMI - kg/m^2 | 31.6 +/- 4.0 | 26 |
| BP Systolic - mmHg | 122.5 +/- 16.2 | 26 |
| BP Diastolic - mmHg | 77.2 +/- 8.0 | 26 |
| Medications - N | 1.7 +/- 0.6 | 19 |

FIG. 8

| | | Baseline | | 1 month | | | 3 months | | |
|---|---|---|---|---|---|---|---|---|---|
| | | N | Value | N | Value | Delta | N | Value | Delta |
| HbA1c | All subjects | 26 | 9.22 | 23 | 8.25 | -0.97 | 14 | 7.99 | -1.23 |
| | >=3 ablations | 16 | 9.42 | 15 | 7.91 | -1.51 | 8 | 7.08 | -2.34 |
| | <3 ablations | 10 | 8.91 | 8 | 8.90 | -0.01 | 6 | 9.22 | 0.31 |
| FPG | All subjects | 26 | 187.6 | 23 | 141.7 | -45.8 | 14 | 160.1 | -27.4 |
| | >=3 ablations | 16 | 186.7 | 15 | 123.1 | -63.6 | 8 | 129.8 | -56.9 |
| | <3 ablations | 10 | 189.0 | 8 | 176.6 | -12.4 | 6 | 200.7 | 11.7 |
| 2hPG | All subjects | 26 | 263.1 | 20 | 199.3 | -63.9 | 14 | 207.1 | -56.0 |
| | >=3 ablations | 16 | 268.9 | 13 | 183.6 | -85.3 | 8 | 163.8 | -105.1 |
| | <3 ablations | 10 | 253.9 | 7 | 228.3 | -25.6 | 6 | 264.8 | 10.9 |

FIG. 9

1 MONTH

| Characteristic | 3 or more | less than 3 | p-value |
|---|---|---|---|
| Number subjects | 15 | 8 | |
| Baseline HbA1c - % | 9.39 +/- 1.42 | 9.08 +/- 1.03 | 0.58 |
| HbA1c Change - % | -1.49 +/- 0.92 | -0.18 +/- 1.00 | 0.0047 |
| Baseline FPG - mg/dL | 187 +/- 68 | 202 +/- 45 | 0.61 |
| FPG Change - mg/dL | -64 +/- 74 | -25 +/- 44 | 0.19 |

3 MONTHS

| Characteristic | 3 or more | less than 3 | p-value |
|---|---|---|---|
| Number subjects | 8 | 6 | |
| Baseline HbA1c - % | 9.36 +/- 1.48 | 9.30 +/- 1.11 | 0.93 |
| HbA1c Change - % | -2.29 +/- 1.24 | -0.08 +/- 1.61 | 0.013 |
| Baseline FPG - mg/dL | 187 +/- 55 | 218 +/- 33 | 0.25 |
| FPG Change - mg/dL | -57 +/- 46 | -18 +/- 64 | 0.20 |

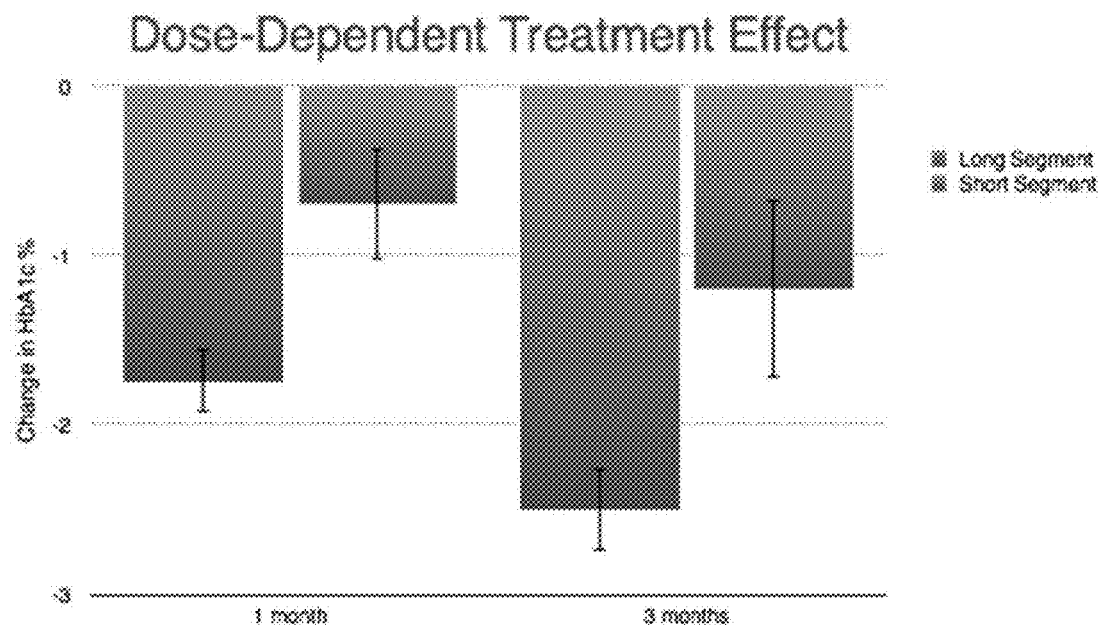
FIG. 25
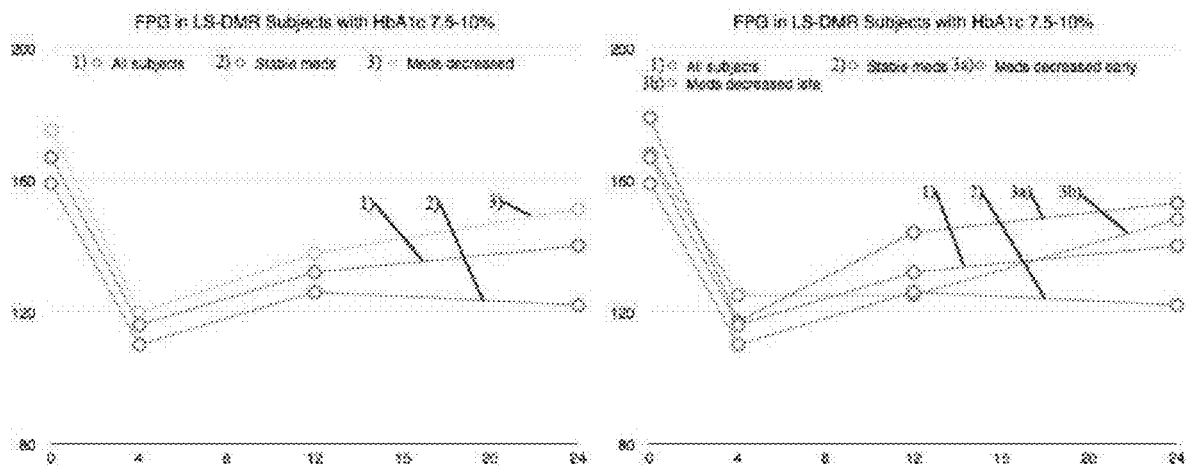
FIG. 26AFIG. 26B

METHODS AND SYSTEMS FOR TREATING DIABETES AND RELATED DISEASES AND DISORDERS

CROSS-REFERENCE TO RELATED APPLICATIONS

This application is a continuation of U.S. patent application Ser. No. 15/406,572, filed Jan. 13, 2017, which is a continuation of PCT Application No. PCT/US2015/040775, filed Jul. 16, 2015, which claims the benefit of U.S. Provisional Application No. 62/025,307, filed Jul. 16, 2014, the entire content of which are incorporated herein by reference.

This application is related to: U.S. patent application Ser. No. 13/945,138, entitled "Devices and Methods for the Treatment of Tissue", filed Jul. 18, 2013; U.S. patent application Ser. No. 14/470,503, entitled "Heat Ablation Systems, Devices and Methods for the Treatment of Tissue, filed Aug. 27, 2014; U.S. patent application Ser. No. 14/515,324, entitled "Tissue Expansion Devices, Systems and Methods", filed Oct. 15, 2014; U.S. patent application Ser. No. 14/609,332, entitled "Electrical Energy Ablation Systems, Devices and Methods for the Treatment of Tissue", filed Jan. 29, 2015; U.S. patent application Ser. No. 14/609,334, entitled "Ablation Systems, Devices and Methods for the Treatment of Tissue", filed Jan. 29, 2015; U.S. patent application Ser. No. 14/673,565, entitled "Methods, Systems and Devices for Performing Multiple Treatments on a Patient", filed Mar. 30, 2015; International Patent Application Serial Number PCT/US2014/040957, entitled "Methods, Systems and Devices for Reducing the Luminal Surface Area of the Gastrointestinal Tract", filed Jun. 4, 2014; International Patent Application Serial Number PCT/US2014/055514, entitled "Systems, Methods and Devices for Treatment of Target Tissue", filed Sep. 12, 2014; International Patent Application Serial Number PCT/US2014/066829, entitled "Systems, Devices and Methods for the Creation of a Therapeutic Restriction in the Gastrointestinal Tract", filed Nov. 21, 2014; International Patent Application Serial Number PCT/US2015/022293, entitled "Injectate Delivery Devices, Systems and Methods", filed Mar. 24, 2015; the entire contents of each are incorporated herein by reference in their entirety.

TECHNICAL FIELD

The embodiments disclosed herein relate generally to methods, systems, and devices for treating a patient, particularly for treating tissue of the gastrointestinal tract to provide a therapy.

BACKGROUND OF THE INVENTION

The current paradigm for medical therapy for type 2 diabetes begins with improvements in diet and exercise. The vast majority of patients do not achieve sustained good glycemic control with lifestyle changes alone. Several classes of pharmacologic therapy are available, including drugs that increase insulin secretion from the pancreas, drugs that enhance the body's sensitivity to insulin, and a variety of other drug classes. Despite these oral therapies, diabetes control will usually deteriorate over time and treatment with insulin will become necessary. All told, however, a large proportion of patients remain poorly controlled despite all of these measures.

There are many reasons for the limited effectiveness of current pharmacologic interventions in the general population. First, today's medicines may lower blood sugar but they do not address the fundamental pathogenesis of Type 2 Diabetes. Second, poor compliance to complicated pharmacologic regimens is well documented and a structural barrier to better glycemic control. Third, clinical inertia on the part of physicians prevents drug regimen escalation even in patients with access to excellent medical care. Fourth, psychological resistance to insulin prevents the use of this class of agents. Fifth, hypoglycemia (and the risk thereof) limits the degree of pharmacologic intervention with which physicians and patients feel comfort. Taken together, nearly 50% of patients remain poorly controlled throughout Europe and the United States.

Interestingly, certain forms of bariatric surgery have a profound anti-diabetic effect in ways that clinicians have only begun to appreciate and characterize. Though the mechanisms underlying this improvement in glucose homeostasis are not completely understood, certain compelling observations have been made. In particular, surgeries that divert the passage of nutrients around the duodenum (or first portion of the small intestine) appear to lead to nearly immediate, extremely durable, and weight-independent anti-diabetic effects. Because the GI tract is the largest endocrine organ in the body, the bypass of the proximal small bowel leads to hormonal changes that improve glucose homeostasis. This effect appears to occur without substantial changes in absorption from the intestine. Rather, these hormonal changes restore the ability of the liver and muscle to suppress endogenous glucose production in response to insulin, a physiologic process that is otherwise impaired in patients with diabetes.

There are two main theories as to why bypass of the proximal small bowel exert such a strong anti-diabetic effect, both of which are likely at least partial contributors. First, some believe that the delivery of excess nutrients to the distal small bowel leads to enhanced secretion of GLP-1 (and perhaps additional related insulin secreting hormones) from the GLP-1-rich entero-endocrine cells of the terminal ileum and colon. Enhanced GLP-1 release into the blood stream after an ingested meal has a number of beneficial effects on glucose homeostasis. A second theory is that patients with diabetes acquire mucosal alterations in their proximal small bowel that contribute to insulin resistance and glucose intolerance. Data from rats and humans suggest that prolonged exposure to a Western diet leads to an increase in enteroendocrine cell numbers and subsequent gastric inhibitory peptide (GIP) after a meal. Other studies have demonstrated hypertrophy of the mucosa of the small bowel in patients with diabetes. In this way, the body's insulin resistance arises from hormones produced by the proximal small bowel as a consequence of these mucosal alterations. Bypass of nutrients around the duodenum prevents the release of these hormones and therefore immediately leads to an improvement in glucose tolerance after surgery.

Unfortunately, as effective as these bariatric surgeries are, one cannot imagine that surgery can be offered to enough patients to adequately address the diabetes pandemic. There are several reasons for this limitation. The primary indication for bariatric surgery remains morbid obesity, yet most diabetics are not morbidly obese. Also, the risks (of major morbidity, mortality, and need for re-operation) from bypass surgeries are quite real and pose a significant barrier to its wholesale adoption as a treatment for type 2 diabetes. Finally, surgery is invasive, psychologically difficult, and physically demanding. For all these reasons, only a minority of patients with diabetes currently undergoes surgery as a treatment for their diabetes.

For these and other reasons, there is a need for improved systems, devices and method for the treatment of diabetes and similar patient diseases and disorders.

SUMMARY

According to one aspect of the present inventive concepts, a system for treating target tissue comprises a tissue treatment device comprising a tissue treatment element constructed and arranged to treat target tissue, the target tissue comprising duodenal mucosa. The system is constructed and arranged to provide a therapeutic benefit to the patient, such as to treat diabetes or another patient disease or disorder.

In some embodiments, the system is configured to counteract duodenal mucosal changes that cause an intestinal hormonal impairment leading to insulin resistance in patients.

In some embodiments, the system is configured to improve the body's ability to process sugar and/or to improve glycemic control in patients with insulin resistance and/or Type 2 diabetes.

In some embodiments, the system is configured to treat diabetes.

In some embodiments, the system is configured to treat hypercholesterolemia.

In some embodiments, the system is configured to treat at least one of a disease or disorder selected from the group consisting of: diabetes; pre-diabetes; impaired glucose tolerance; insulin resistance; obesity or otherwise being overweight; a metabolic disorder and/or disease; and combinations thereof.

In some embodiments, the system is configured to treat at least one of a disease or disorder selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease; stroke; TIA; cognitive decline; dementia; diabetic nephropathy; neuropathy; retinopathy; diabetic heart disease; diabetic heart failure; and combinations thereof.

In some embodiments, the system is configured to treat two or more of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease; stroke; TIA; cognitive decline; dementia; diabetic nephropathy; neuropathy; retinopathy; diabetic heart disease; and diabetic heart failure.

In some embodiments, the system is configured to avoid treatment of non-target tissue. The non-target tissue can comprise the ampulla of Vater. The non-target tissue can comprise tissue selected from the group consisting of: gastrointestinal adventitia; duodenal adventitia; the tunica serosa; the tunica muscularis; the outermost partial layer of the submucosa; ampulla of Vater; pancreas; bile duct; pylorus; and combinations thereof.

In some embodiments, the target tissue comprises at least two axial segments of duodenal mucosa, and the therapeutic benefit results from the treatment of the at least two axial segments by the tissue treatment element. Each axial segment can comprise a length between approximately 1.9 cm and 3.3 cm. Each axial segment can comprise a length of approximately 3 cm. The target tissue can comprise an approximately full circumferential portion of each axial segment (i.e. approximately 360° of the mucosal layer of each axial segment) or a partial circumferential portion of each axial segment (i.e. less than 360° of the mucosal layer of each axial segment).

In some embodiments, the target tissue comprises at least four (full or partial circumferential) axial segments of duodenal mucosa, and the therapeutic benefit results from the treatment of the at least four axial segments by the tissue treatment element. The target tissue can comprise at least six axial segments of duodenal mucosa, and the therapeutic benefit results from the treatment of the at least six axial segments by the tissue treatment element. Each axial segment can comprise a length between approximately 0.7 cm and 2.0 cm.

In some embodiments, the system is configured to cause a therapeutic benefit selected from the group consisting of: improvement in HbA1c, fasting glucose and/or post-prandial glucose; at least a 1% improvement in HbA1c; a resultant HbA1c of less than 7.5%, less than 7.0%, less than 6.5%, or less than 6.0%; improvement in one or more triglyceride levels; improvement in AST, ALT, liver fibrosis panel, liver fibrosis score, NAFLD assessment and/or or NASH assessment; improvement in risk of myocardial infarction, stroke, TIA and/or peripheral vascular disease or diabetic cardiomyopathy; improvement in microvascular disease risk such as nephropathy, retinopathy and/or neuropathy; reduced development of end-stage renal disease, blindness and/or amputation; reduced insulin requirement (e.g. in patients with insulin-dependent diabetes) or other injectable therapy requirement; reduced medication requirement (e.g. in patients with diabetes) either in number of medicines or dosage of medicines; improved fetal birth outcomes (e.g. in patients with gestational diabetes); improved fertility in patients with polycystic ovarian syndrome and/or reduced hirsutism; weight loss of at least 5% of excess body weight, or at least 10%, 20%, 30% or 40% of excess body weight; reduced blood pressure; reduced cardiovascular risk; improved diabetes control and/or reduced diabetic complications; reduced obesity and/or reduced weight; reduced cognitive decline or prevention of dementia; and combinations thereof. The therapeutic benefit can have a clinically significant durability of at least 3 months. The therapeutic benefit can have a clinically significant durability of at least 6 months, or at least 1 year.

In some embodiments, the system is configured to reduce the HbA1c level of the patient. The system can be configured to cause an HbA1c reduction of approximately 2.18%. The system can be configured to cause an HbA1c reduction of at least 0.7%. The system can be configured to cause an HbA1c reduction of at least 1.0%. The system can be configured to cause an HbA1c reduction of at least 1.5%. The system can be configured to cause an HbA1c reduction of at least 2.0%. The system can be configured to cause an HbA1c reduction of at least 2.5%. The system can be configured to reduce HbA1c to a target level less than or equal to 7.5%. The system can be configured to reduce HbA1c to a target level less than or equal to 7.0%. The system can be configured to reduce HbA1c to a target level less than or equal to 5.5%. The system can be configured to cause an HbA1c level below 7.5% at least 150 days after performance of the target tissue treatment.

In some embodiments, the system is configured to reduce FPG. The system can be configured to cause an FPG reduction of approximately 63.5 mg/dl. The system can be configured to reduce FPG to a target level less than or equal to 150 mg/dl. The system can be configured to reduce FPG to a target level less than or equal to 126 mg/dl. The system can be configured to reduce FPG to a target level less than or equal to 100 mg/dl.

In some embodiments, the system is configured to improve fasting glucose and/or HbA1c without causing a significant decline in fasting insulin and/or post-prandial insulin.

In some embodiments, the system is configured to improve beta cell insulin secretory capacity for at least 3 months. The system can be configured to improve beta cell insulin secretory capacity for at least 6 months, or at least 1 year.

In some embodiments, the system is configured to prevent the decline of beta cell insulin secretory capacity for at least 3 months.

In some embodiments, the system is configured to reduce 2hPG. The system can be configured to cause a 2hPH reduction of approximately 103.7 mg/dl. The system can be configured to reduce 2hPG to a target level less than or equal to 250 mg/dl. The system can be configured to reduce 2hPG to a target level less than or equal to 200 mg/dl. The system can be configured to reduce 2hPG to a target level less than or equal to 175 mg/dl.

In some embodiments, the system is configured to provide an improvement in a patient condition as measured by the SF-36 Health Survey. The improvement can comprise an improvement in the Mental Change score of the SF-36 Health Survey. The improvement can comprise a score change of at least 3 points, or at least 5 points. The improvement can comprise a score change of at least 10 points.

In some embodiments, the system is configured to provide a reduction in excess body weight of the patient. The reduction can comprise a reduction of at least 5% of excess body weight. The reduction can comprise a reduction of at least 10% of excess body weight. The reduction can comprise a reduction of at least 20% of excess body weight. The reduction can comprise a reduction of at least 30% of excess body weight. The reduction can comprise a reduction of at least 40% of excess body weight.

In some embodiments, the system is configured to treat a patient with a duration of diabetes less than 10 years.

In some embodiments, the system is configured to treat a patient with an age between 18 years and 75 years.

In some embodiments, the system is configured to treat a patient with an age between 5 years and 18 years.

In some embodiments, the system is configured to treat a patient with a BMI between 22 and 60.

In some embodiments, the system is configured to treat a patient with an HbA1c between 6.0% and 12.0%. The system can be configured to treat a patient with an HbA1c between 7.5% and 12.0%. The system can be configured to treat a patient with an HbA1c between 7.5% and 10.0%, such as between 7.5% and 9.0%.

In some embodiments, the target tissue further comprises non-duodenal mucosa tissue.

In some embodiments, the target tissue comprises duodenal mucosa located distal to the ampulla of Vater.

In some embodiments, the target tissue comprises at least 10% of the duodenal mucosa located distal to the ampulla of Vater.

In some embodiments, the target tissue comprises at least 15% of the duodenal mucosa located distal to the ampulla of Vater.

In some embodiments, the target tissue comprises at least 25% of the duodenal mucosa located distal to the ampulla of Vater.

In some embodiments, the target tissue comprises at least 15% of the duodenal mucosa located distal to the ampulla of Vater.

In some embodiments, the target tissue comprises at least 50% of the duodenal mucosa located distal to the ampulla of Vater.

In some embodiments, the target tissue comprises an axial length (e.g. a cumulative axial length) of duodenal mucosa of at least 6 cm, such as at least 7 cm, at least 8 cm, at least 9 cm or approximately 9.3 cm of duodenal mucosa. The cumulative axial length can be treated by treating (e.g. ablating) one or more (e.g. three) full or partial circumferential axial segments of the duodenum.

In some embodiments, the target tissue does not comprise any duodenal mucosa located proximal to the ampulla of Vater.

In some embodiments, the target tissue comprises no more than 70% of the duodenal mucosa located distal to the ampulla of Vater and the target tissue does not comprise any duodenal mucosa tissue located proximal to the ampulla of Vater.

In some embodiments, the target tissue comprises no more than 90% of the duodenal mucosa located distal to the ampulla of Vater and the target tissue does not comprise any duodenal mucosa tissue located proximal to the ampulla of Vater.

In some embodiments, the target tissue comprises tissue located at least 1 cm distal to the ampulla of Vater, such as when the target tissue does not include tissue within 1 cm of the ampulla of Vater.

In some embodiments, the system further comprises at least one deployable marker, and the target tissue comprises tissue selected based on the deployment location of the at least one marker.

In some embodiments, the system is configured to alter the intestinal mucosal hormone production from the region of treated target tissue.

In some embodiments, the system is configured to alter a hormonal secretion pattern that affects blood glucose levels in the fasting and post-prandial states.

In some embodiments, the system is configured to change the blood levels of GIP and/or GLP-1 to change glucose homeostasis in the fasting and/or post-prandial states.

In some embodiments, the system is configured to change insulin and/or glucagon secretion from the pancreas and/or insulin and/or glucagon levels in the bloodstream.

In some embodiments, the system is configured to change pancreatic beta cell function and/or health through direct hormonal consequences of the treated duodenal tissue and/or indirectly through improved blood glucose levels.

In some embodiments, the system is configured to cause a change in a patient secretion parameter. The system can be configured to cause the change in a patient secretion parameter by causing an effect selected from the group consisting of: modifying the target tissue; ablating, removing and/or causing the necrosis of the target tissue resulting in replacement of the target tissue with new tissue; reducing the surface area of the target tissue; and combinations thereof. The system can be configured to modify the target tissue to cause the change in a patient secretion parameter. The modified target tissue can comprise tissue with different secretion parameters than the pre-treated tissue. The modified target tissue can comprise tissue with reduced surface area than the pre-treated tissue. The system can be configured to ablate, cause the necrosis of and/or remove the target tissue, resulting in replacement of the target tissue with new tissue, to cause the change in a patient secretion parameter. The new tissue can comprise tissue with different secretion parameters than the pre-treated tissue. The new tissue can comprise tissue with reduced surface area than the pre-treated tissue. The patient secretion parameter can comprise a secretion parameter selected from the group consisting of: quantity of a patient secretion during a time period; average rate of a patient secretion during a time period; peak excursion of a patient secretion parameter; and combinations thereof. The system can be configured to cause a change in multiple patient secretion parameters. The change in a patient secretion parameter can be exhibited when the patient is in a state selected from the group consisting of: fasting state; post-prandial state; and combinations thereof. The change in a patient secretion parameter can comprise at least a 10% reduction in GIP secretions. The at least a 10% reduction in GIP secretions can comprise at least a 10% reduction in the amount of GIP secreted in a time period. The at least a 10% reduction in GIP secretions can comprise at least a 10% reduction in the average rate of GIP secretions during a time period. The at least a 10% reduction in GIP secretions can comprise at least a 25% reduction in GIP secretions. The at least a 10% reduction in GIP secretions can comprise at least a 50% reduction in GIP secretions. The change in a patient secretion parameter can result in a reduction in GIP serum concentration selected from the group consisting of: reduced 10%; reduced 25%; and/or reduced 50%. The change in a patient secretion parameter can comprise at least a 10% increase in GLP-1 secretions. The at least a 10% increase in GLP-1 secretions can comprise at least a 10% increase in the amount of GLP-1 secreted in a time period. The at least a 10% increase in GLP-1 secretions can comprise at least a 10% increase in the average rate of GLP-1 secretions during a time period. The at least a 10% increase in GLP-1 secretions can comprise at least a 25% increase in GLP-1 secretions. The at least a 10% increase in GLP-1 secretions can comprise at least a 50% increase in GLP-1 secretions. The change in a patient secretion parameter can result in an increase in GLP-1 serum concentration selected from the group consisting of: increased 10%; increased 25%; and/or increased 50%. The change in a patient secretion parameter can comprise at least a 10% reduction in glucagon secretions. The at least a 10% reduction in glucagon secretions can comprise at least a 10% reduction in the amount of glucagon secreted in a time period. The at least a 10% reduction in glucagon secretions can comprise at least a 10% reduction in the average rate of glucagon secretions during a time period. The at least a 10% reduction in glucagon secretions can comprise at least a 25% reduction in glucagon secretions. The at least a 10% reduction in glucagon secretions can comprise at least a 50% reduction in glucagon secretions. The change in a patient secretion parameter can result in a reduction in glucagon serum concentration selected from the group consisting of: reduced 10%; reduced 25%; and reduced 50%.

In some embodiments, the system is configured to cause a change in a patient absorption parameter. The system can be configured to cause the change in a patient absorption parameter by causing an effect selected from the group consisting of: modifying the target tissue; ablating, removing and/or causing the necrosis of target tissue resulting in replacement of the target tissue with new tissue; reducing the surface area of the target tissue; and combinations thereof. The system can be configured to modify the target tissue to cause the change in a patient absorption parameter. The modified target tissue can comprise tissue with different absorption parameters than the pre-treated tissue. The modified target tissue can comprise tissue with reduced surface area than the pre-treated tissue. The system can be configured to ablate, cause the necrosis of and/or remove the target tissue, resulting in replacement of the target tissue with new tissue, to cause the change in a patient absorption parameter. The new tissue can comprise tissue with different absorption parameters than the pre-treated tissue. The new tissue can comprise tissue with reduced surface area than the pre-treated tissue. The patient absorption parameter can comprise an absorption parameter selected from the group consisting of: quantity of a substance absorbed during a time period; average rate of a substance absorbed during a time period; and combinations thereof. The system can be configured to cause a change in multiple patient absorption parameters. The change in a patient absorption parameter can be exhibited when the patient is in a state selected from the group consisting of: fasting state; post-prandial state; and combinations thereof. The change in a patient absorption parameter can comprise at least a 10% decrease in glucose absorption. The at least a 10% decrease in glucose absorption can comprise at least a 10% decrease in the amount of glucose absorbed in a time period. The at least a 10% decrease in glucose absorption can comprise at least a 10% decrease in the average rate of glucose absorption during a time period. The at least a 10% decrease in glucose absorption can comprise at least a 25% decrease in glucose absorption. The at least a 10% decrease in glucose absorption can comprise at least a 50% decrease in glucose absorption.

In some embodiments, the system is configured to cause a decrease in GIP and an increase in GLP-1.

In some embodiments, a pre-treatment GIP/GLP-1 ratio comprises the ratio of GIP secretion levels prior to the treatment of the target tissue compared to the GLP-1 secretion levels prior to the treatment of the target tissue, and a post-treatment GIP/GLP-1 ratio comprises the ratio of GIP secretion levels after the treatment of the target tissue compared to the GLP-1 secretion levels after the treatment of the target tissue. A treatment effect comprises the ratio of the post-treatment GIP/GLP-1 ratio compared to the pre-treatment GIP/GLP-1 ratio and the system can be configured to cause a treatment effect of less than 1.0. The system can be configured to cause a treatment effect of less than 0.90. The system can be configured to cause a treatment effect of less than 0.75. The system can be configured to cause a treatment effect of less than 0.50.

In some embodiments, the tissue treatment device further comprises a tissue expanding element.

In some embodiments, the tissue treatment element comprises an element selected from the group consisting of: an ablative fluid delivered to a balloon or other expandable fluid reservoir; a tissue treatment element comprising an energy delivery element mounted to an expandable assembly such as an electrode or other energy delivery element configured to deliver radiofrequency (RF) energy and/or microwave energy; a light delivery element configured to deliver laser or other light energy; a fluid delivery element configured to deliver ablative fluid directly onto tissue; a sound delivery element such as a ultrasonic and/or subsonic sound delivery element; and combinations thereof.

In some embodiments, the tissue treatment element comprises a first tissue treatment element and a second tissue treatment element. The first tissue treatment element can be dissimilar to the second tissue treatment element.

In some embodiments, the tissue treatment device further comprises an expandable balloon, and the tissue treatment element comprises ablative fluid delivered to the expandable balloon. The ablative fluid can comprise fluid at sufficiently high temperature to cause tissue necrosis. The expandable balloon can comprise a material selected from the group consisting of: polyethylene terephthalate (PET); nylon; latex; polyurethane; Pebax; and combinations thereof. The expandable balloon can comprise a wall comprising a thickness between approximately 0.0002" and 0.0020". The expandable balloon can comprise a wall comprising a thickness of approximately 0.0005". The expandable balloon can comprise a wall comprising a thickness of approximately 0.0010". The expandable balloon can comprise a tissue contacting portion. The tissue contacting portion can comprise a diameter of between approximately 19.0 mm and 32.0 mm. The tissue contacting portion can comprise a length of between approximately 16.0 mm and 35.0 mm. The tissue contacting portion can comprise a length of between approximately 19.5 mm and 32.9 mm. The tissue contacting portion can comprise a surface area of between approximately 1750 $mm^2$ and 2150 $mm^2$. The tissue contacting portion can comprise a surface area of approximately 1950 $mm^2$. The expandable balloon can comprise a tapered distal end. The expandable balloon tapered distal end can comprise a taper between approximately 27° and 33°. The expandable balloon can comprise a tapered proximal end. The expandable balloon tapered proximal end can comprise a taper between approximately 42° and 48°. The expandable balloon can be constructed and arranged to be filled with approximately 10 ml to 35 ml of ablative fluid. The tissue treatment device can comprise a first tissue treatment device, and the system can further comprise a second tissue treatment device comprising a second tissue treatment element and a second expandable balloon. The first tissue treatment device expandable balloon can comprise a first tissue contacting surface area and the second expandable balloon can comprise a second tissue contacting surface area similar to the first tissue contacting surface area. The first tissue treatment device expandable balloon can comprise a different length and/or diameter than the second expandable balloon of the second tissue treatment device.

In some embodiments, the system is configured to both cool and heat the target tissue. The system can be configured to: in a first step, cool the target tissue with the tissue treatment element by supplying a first fluid to the treatment element for a first time period, and the first fluid is supplied within a first temperature range; in a second step, heat the target tissue with the tissue treatment element by supplying a second fluid to the treatment element for a second time period, and the second fluid is supplied within a second temperature range; and in a third step, cool the target tissue with the tissue treatment element by supplying a third fluid to the treatment element for a third time period, and the third fluid is supplied within a third temperature range. The heating of the target tissue in the second step can be configured to ablate the target tissue. The first time period can comprise a duration (e.g. a time duration) of between approximately 15 seconds and 30 seconds. The first temperature range can comprise one or more temperatures between approximately 5° C. and 25° C., such as between 15° C. and 25° C. The second time period can comprise a duration of between approximately 8 seconds and 15 seconds. The first temperature range can comprise one or more temperatures between approximately 85° C. and 95° C. The second time period can comprise a duration of between approximately 15 seconds and 30 seconds. The first temperature range can comprise one or more temperatures between approximately 5° C. and 25° C., such as between 15° C. and 25° C. The second time period can comprise a duration less than the first time period duration. The second time period can comprise a duration less than the third time period duration. The second time period can comprise a duration less than both the first time period duration and the third time period duration. The second temperature can comprise a temperature at least 18° above the first temperature and/or the third temperature. The second temperature can comprise a temperature at least 60° above the first temperature and/or the third temperature. The first temperature and the third temperature can comprise similar temperatures.

In some embodiments, the tissue treatment device comprises an expandable assembly comprising the tissue treatment element, and the system is configured to monitor the pressure and/or volume of the expandable assembly. The system can be configured to use the monitored pressure and/or volume to compensate for peristalsis and/or muscle contractions of the GI tract. The system can be configured to use the monitored pressure and/or volume to compensate for changes in GI tract lumen diameter.

In some embodiments, the system is configured expand tissue, and the system is further configured to only ablate target tissue comprising: the expanded tissue and/or tissue proximate the expanded tissue.

In some embodiments, the tissue treatment element comprises ablative fluid and the tissue treatment device comprises an expandable balloon constructed and arranged to receive the ablative fluid. The expandable balloon comprises a tissue contacting portion including a length, and the system is configured to translate the expandable balloon approximately the length of the tissue contacting portion after a first portion of target tissue is treated. The translation can comprise a manual translation (e.g. performed by a clinician). The system can further comprise a motion transfer assembly and the translation comprises at least a semi-automated translation.

In some embodiments, the system is configured to treat a first, second and third portion of target tissue and to perform an assessment of the distance between the most proximal tissue treated and non-target tissue. The second target tissue portion can be distal to the third target tissue portion, and the first target tissue portion can be distal to the second target tissue portion, and the system can be configured to treat the first target tissue portion, the second target tissue portion, and then the third target tissue portion sequentially. The non-target tissue can comprise the ampulla of Vater, and non-target tissue can include tissue within 1 cm of the ampulla of Vater (e.g. on either side). The system can be configured to treat a fourth portion of target tissue proximal to the most proximal tissue treated, if the distance between the most proximal tissue treated and the non-target tissue is above a threshold.

In some embodiments, the system is configured to prevent two ablations within a pre-determined time period. The pre-determined time period can be configured to prevent repetitive ablations in similar portions of the GI tract.

In some embodiments, the system is configured to prevent a tissue ablation and/or tissue treatment until a submucosal expansion step has been performed.

In some embodiments, the system is configured to expand tissue, and the treatment of the target tissue is completed within 120 minutes of initiating tissue expansion. The treatment of the target tissue can be completed within 60 minutes of initiating tissue expansion. The treatment of the target tissue can be completed within 45 minutes of initiating tissue expansion.

In some embodiments, the system is configured to select target tissue based on a patient condition. The amount of target tissue can be proportional to the severity of the patient condition. The amount of target tissue can be proportional to the disease burden of the patient condition. An elevated disease burden can comprise one or more of: relatively long duration since diagnosis; higher HbA1c level than a standard diabetic patient; and more mucosal hypertrophy than a standard diabetic patient. The amount of target tissue can be proportional to the HbA1c level of the patient.

In some embodiments, the system is configured to provide post-procedure management of the patient after the treatment of the target tissue. The post-procedure management can comprise a liquid diet for at least one day. The post-procedure management can comprise a low sugar diet and/or a low fat diet for at least one week. The post-procedure management can comprise a standardized diabetic diet for at least 1 week. The post-procedure management can comprise nutritional counseling for at least 1 week.

In some embodiments, the system further comprises a console configured to interface with at least the tissue treatment device. The console can comprise a controller. The console can comprise an energy delivery unit. The tissue treatment element can comprise ablative fluid and the energy delivery unit can be constructed and arranged to provide the ablative fluid to the tissue treatment device. The console can comprise a user interface. The console can comprise a safety-switch. The safety-switch can be configured to be activated without articulation of an operator digit of a hand. The tissue treatment device can comprise an expandable assembly, and the system can be configured to automatically contract the expandable assembly if the safety-switch is not activated. The tissue treatment device can comprise a balloon, the tissue treatment element can comprise ablative fluid, the system can comprise neutralizing fluid, and the system can be configured to automatically replace ablative fluid in the balloon with the neutralizing fluid if the safety switch is not activated. The tissue treatment device can comprise a balloon, the tissue treatment element can comprise ablative fluid, the system can comprise cooling fluid, and the system can be configured to deliver the ablative fluid to the balloon upon activation of the safety-switch, such as at a time after which cooling fluid has been delivered to the balloon and an operator has confirmed proper position of the balloon for treatment of target tissue. The safety-switch can be configured to allow hands-free activation and/or maintenance of a treatment step such that one or more operators can maintain their hands on one or more of: the tissue treatment device; an endoscope; a tissue expansion device; and a lumen diameter sizing device. The safety-switch can comprise a foot activated switch. The safety-switch can comprise a hand-detection sensor. The tissue treatment device can comprise a handle, and the safety switch can be constructed and arranged to detect the position of an operator hand on at least the tissue treatment device handle. The system can comprise an endoscope including a handle, and the safety switch can be constructed and arranged to detect the position of an operator hand on at least the endoscope handle. The console can comprise a pressure assembly. The console can comprise a fluid source. The console can comprise a functional element.

In some embodiments, the system further comprises a functional element. The tissue treatment device can comprise the functional element. The system can further comprise a console and the console can comprise the functional element. The system can further comprise a tissue expansion device, and the tissue expansion device can comprise the functional element. The system can further comprise a gastrointestinal lumen sizing device and the sizing device can comprise the function element. The functional element can comprise a sensor selected from the group consisting of: temperature sensor such as a thermocouple, thermistor, resistance temperature detector and optical temperature sensor; strain gauge; impedance sensor such as a tissue impedance sensor; pressure sensor; blood sensor; optical sensor such as a light sensor; sound sensor such as an ultrasound sensor; electromagnetic sensor such as an electromagnetic field sensor; visual sensor; and combinations thereof. The functional element can comprise a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; a fluid agitating element; and combinations thereof.

In some embodiments, the system further comprises a tissue expansion device including at least one fluid delivery element constructed and arranged to deliver injectate to expand one or more tissue layers. The system can further comprise an injectate, and the injectate is selected from the group consisting of: water; saline; a fluid with a dye such as a visible dye such as indigo carmine; methylene blue; India ink; SPOT™ dye; a gel; a hydrogel; a protein hydrogel; a fluid containing a visualizable media such as a media visualizable under X-ray, ultrasound imaging and/or magnetic resonance imaging; ethylene vinyl alcohol (EVOH); and combinations thereof. The tissue expansion device can comprise an expandable balloon and the at least one fluid delivery element can be attached to the balloon. The tissue expansion device can further comprise a tissue capture port surround the at least one fluid delivery element. The system can be configured to deliver a first fluid volume to the expandable balloon and measure a first pressure and to deliver a second fluid volume to the expandable balloon and measure a second pressure, such as when the second fluid of volume is less than the first fluid volume. The system can be further configured to apply a first vacuum while the expandable balloon is filled with the second volume of fluid, to cause tissue to enter the tissue capture port. The system can be configured to confirm the first pressure is less than the second pressure. The tissue expansion device can further comprise an expandable assembly comprising the at least one fluid delivery element. The expandable assembly can comprise an expandable balloon. The system can be configured to measure the pressure and/or volume and to determine if a proper volume of the injectate has been delivered to achieve adequate tissue expansion based on the measured pressure and/or volume. The system can be configured to expand tissue located at least 0.5 cm distal to the ampulla of Vater, such as when tissue within 0.5 cm distal to the ampulla of Vater is not expanded and/or is not subsequently ablated. The system can be configured to expand tissue located at least 1 cm distal to the ampulla of Vater, such as when tissue within 1 cm of the ampulla of Vater is not expanded and/or is not subsequently ablated. The system can be configured to expand tissue located at least 2 cm distal to the ampulla of Vater, such as when tissue within 2 cm of the ampulla of Vater is not expanded and/or is not subsequently ablated. The system can be configured to expand tissue located at least 3 cm distal to the ampulla of Vater, such as when tissue within 3 cm of the ampulla of Vater is not expanded and/or is not subsequently ablated. The system can be configured to expand tissue located within 5 cm distal to the ampulla of Vater. The system can be configured to expand tissue located within 10 cm distal to the ampulla of Vater. The at least one fluid delivery element can comprise at least three fluid delivery elements. The tissue expansion device can further comprise an expandable assembly, and the at least three fluid delivery elements can comprise three fluid delivery elements positioned with approximately 120° separation on the expandable assembly. The at least three fluid delivery elements can be constructed and arranged to create full circumferential expansion of a segment of submucosal tissue of the duodenum. The tissue expansion device can be constructed and arranged to deliver at least 1 ml of injectate per injection from the at least one fluid delivery element. The tissue expansion device can be constructed and arranged to deliver at least 2 ml of injectate per injection from the at least one fluid delivery element. The tissue expansion device can be constructed and arranged to deliver at least 5 ml of injectate per injection from the at least one fluid delivery element. The tissue expansion device can be constructed and arranged to deliver at least 8 ml of injectate per injection from the at least one fluid delivery element. The tissue expansion device can be configured to deliver multiple injections of injectate along a length of the GI tract, and the injections can be axially separated by at least 0.5 cm. The tissue expansion device can be configured to deliver the multiple injections of injectate with an axial separation of at least 1.0 cm. The tissue expansion device can be configured to deliver the multiple injections of injectate with an axial separation of at least 2.0 cm. The tissue expansion device can be configured to deliver the multiple injections of injectate with an axial separation of at least 3.0 cm. The tissue expansion device can be configured to deliver the multiple injections of injectate with an axial separation of at least 4.0 cm. The tissue expansion device can be configured to deliver the multiple injections of injectate with an axial separation of at least 6.0 cm. The at least one fluid delivery element can comprise at least two fluid delivery elements (e.g. multiple fluid delivery elements configured to simultaneously or sequentially deliver sets of injections), and the tissue expansion device can be configured to deliver at least 5 sets of injections at different axial locations along the length of the duodenum. The tissue expansion device can be configured to deliver at least 8 sets of injections at different axial locations along the length of the duodenum. The tissue expansion device can be configured to deliver between 8 and 12 sets of injections at different axial locations along the length of the duodenum. Each set of injections can comprise a first injection from a first fluid delivery element and a second injection from a second fluid delivery element, each set of injections delivered along a circumference of a GI tract axial location. Each set of injections can comprise a first injection from a first fluid delivery element, a second injection from a second fluid delivery element, and a third injection from a third fluid delivery element, each set of injections delivered along a circumference of a GI tract axial location. The sets of injections can be positioned with an axial separation of at least 0.5 cm. The sets of injections can be positioned with an axial separation of between 1.0 cm and 5.0 cm. The sets of injections can be positioned with an axial separation of between 1.0 cm and 2.0 cm. The tissue expansion device can comprise a balloon with a balloon length and the at least two fluid delivery element are mounted to the balloon, and the sets of injections can be positioned with an axial separation of approximately one-half the balloon length. The sets of injections can be delivered proximally to distally along the GI tract. The sets of injections can be delivered distally to proximally along the GI tract.

In some embodiments, the system further comprises a lumen diameter sizing device constructed and arranged to provide GI lumen diameter information. The lumen diameter sizing device can comprise an expandable balloon. The system can be configured to determine the volume delivered to the lumen diameter sizing device expandable balloon. The system can be configured to deliver fluid to the lumen diameter sizing device expandable balloon until a threshold pressure is achieved. The threshold pressure can comprise a threshold of at least 0.7 psi. The lumen diameter sizing device can be configured to determine the luminal diameter of at least two GI tract axial locations. The system can be configured to determine the size of the tissue treatment device to be used based on the GI lumen diameter information provided by the lumen diameter sizing device. The system can further comprise a tissue expansion device and the system can be configured to determine the size of the tissue expansion device to be used based on the GI lumen diameter information provided by the lumen diameter sizing device.

In some embodiments, the system further comprises an agent. The agent can be configured to be delivered to the GI tract. The agent can be configured to be delivered systemically to the patient. The agent can comprise an anti-peristaltic agent. The agent can comprise L-menthol. The agent can comprise an agent selected from the group consisting of: glucagon; buscopan; and combinations thereof.

In some embodiments, the system further comprises a marker constructed and arranged to be deployed within the patient. The marker can be constructed and arranged to identify a location relative to non-target tissue. The non-target tissue can comprise the ampulla of Vater, and it can include tissue proximate the ampulla of Vater, such as tissue within 1 cm, 2 cm or 3 cm of the ampulla of Vater. The marker can comprise an element selected from the group consisting of: a visible marker; a radiographic marker; an ultrasonically reflectable marker; ink; dye; and combinations thereof. The marker can comprise multiple markers. The system can further comprise an endoscope and the marker can be constructed and arranged to be deployed by the endoscope. The marker can be constructed and arranged to be deployed by the tissue treatment device.

In some embodiments, the system further comprises an endoscope and a scope attached sheath attachable to the endoscope. The tissue treatment device can be constructed and arranged to be inserted through the scope attached sheath.

According to another aspect of the present inventive concepts, a tissue treatment device for treating target tissue comprises a tissue treatment element constructed and arranged to apply a tissue modifying agent to target tissue and the system is constructed and arranged to provide a therapeutic benefit to the patient.

In some embodiments, the target tissue comprises duodenal mucosa.

In some embodiments, the tissue treatment element comprises an expandable element. The tissue treatment element can expand when contacted with fluid. The tissue treatment element can expand when contacted with the tissue modifying agent.

In some embodiments, the tissue treatment element comprises a sponge material. The sponge material can be selected from the group consisting of: a sponge material such as a natural sponge material or a synthetic sponge material; a foamed polyurethane; a polyvinyl alcohol (PVA) sponge; a hydrogel; a super-absorbent polymer; and combinations thereof.

In some embodiments, the tissue treatment element comprises a balloon. The balloon can comprise a permeable balloon.

In some embodiments, the tissue treatment device further comprises the tissue modifying agent.

In some embodiments, the tissue modifying agent is configured to cause necrosis of the target tissue. The tissue modifying agent can be selected from the group consisting of: a chemical peeling agent; a mild acid such as glycolic acid; trichloroacetic acid; a mild base; phenol; retinoic acid; and combinations thereof.

In some embodiments, the tissue treatment device further comprises a shaft with a proximal end and a distal portion, and the tissue treatment element is positioned on the distal portion of the shaft. The shaft can comprise a length sufficient to position the tissue treatment element proximate the distal end of the duodenum of the patient. The shaft can comprise a lumen constructed and arranged for over-the-wire insertion of the tissue treatment device. The tissue treatment device can further comprise a handle positioned on the proximal end of the shaft.

In some embodiments, the tissue treatment device further comprises at least one occluding element constructed and arranged to at least partially occlude a lumen of the GI tract. The at least one occluding element can be further configured to prevent migration of the tissue modifying agent to non-target tissue. The at least one occluding element can comprise a radially expandable element. The at least one occluding element can comprise an expandable balloon. The at least one occluding element can comprise an expandable sponge. The at least one occluding element can comprise multiple occluding elements. The at least one occluding element can be constructed and arranged to be evacuated from the patient by the patient's digestive system. The tissue treatment device can further comprise a grasping device, and the at least one occluding element can be constructed and arranged to be removed from the patient by the grasping device. The tissue treatment device can further comprise a shaft with a lumen, and the at least one occluding element can be constructed and arranged to be deployed into the patient via the shaft lumen. The tissue treatment device can further comprise a push rod translatable through the lumen and constructed and arranged to expel the occluding element from the shaft.

According to another aspect of the present inventive concepts, a tissue modifying agent delivery system comprises a tissue treatment device as described herein. The system further comprises a tissue modifying agent delivery unit configured to deliver a tissue modifying agent to the tissue treatment element.

In some embodiments, the tissue modifying agent delivery system comprises a system as described herein.

In some embodiments, the target tissue comprises duodenal mucosa located distal to the ampulla of Vater. The target tissue can comprise tissue at least 0.5 cm distal to the ampulla of Vater, such as when tissue within 0.5 cm of the ampulla of Vater is not ablated or otherwise treated. The target tissue can comprise tissue at least 1 cm distal to the ampulla of Vater, such as when tissue within 1 cm of the ampulla of Vater is not ablated or otherwise treated. The target tissue comprises tissue at least 2 cm distal to the ampulla of Vater, such as when tissue within 2 cm of the ampulla of Vater is not ablated or otherwise treated. The target tissue comprises tissue at least 3 cm distal to the ampulla of Vater, such as when tissue within 3 cm of the ampulla of Vater is not ablated or otherwise treated.

In some embodiments, the target tissue comprises at least 25% of the duodenal mucosa located distal to the ampulla of Vater.

In some embodiments, the target tissue comprises at least 50% of the duodenal mucosa located distal to the ampulla of Vater.

In some embodiments, the target tissue does not comprise any duodenal mucosa located proximal to the ampulla of Vater.

In some embodiments, the target tissue comprises no more than 75% of the duodenal mucosa located distal to the ampulla of Vater and the target tissue does not comprise any duodenal mucosa tissue located proximal to the ampulla of Vater.

In some embodiments, the target tissue comprises no more than 90% of the duodenal mucosa located distal to the ampulla of Vater and the target tissue does not comprise any duodenal mucosa tissue located proximal to the ampulla of Vater.

In some embodiments, the target tissue comprises tissue located at least 1 cm distal to the ampulla of Vater.

In some embodiments, the system further comprises at least one deployable marker, and the target tissue comprises tissue selected based on the deployment location of the at least one marker.

In some embodiments, the target tissue comprises an axial length of at least 6 cm. The target tissue can comprise an axial length of at least 9 cm.

In some embodiments, the target tissue comprises a single contiguous segment of duodenal mucosa.

In some embodiments, the target tissue comprises multiple discontiguous segments of duodenal mucosa.

In some embodiments, the target tissue comprises tissue at least 1 cm distal to the ampulla of Vater, such as when tissue within 1 cm of the ampulla of Vater is not ablated or otherwise treated. The target tissue can comprise tissue at least 2 cm distal to the ampulla of Vater, such as when tissue within 2 cm of the ampulla of Vater is not ablated or otherwise treated. The target tissue can comprise tissue at least 3 cm distal to the ampulla of Vater, such as when tissue within 3 cm of the ampulla of Vater is not ablated or otherwise treated.

In some embodiments, the system of the present inventive concepts comprises a first tissue treatment device and a second tissue treatment device, each tissue treatment device comprising a tissue treatment element constructed and arranged to treat (e.g. ablate, remove or otherwise modify) target tissue. The first tissue treatment device is constructed and arranged to treat duodenal mucosa in a first procedure, and the second tissue treatment device is constructed and arranged to treat duodenal mucosa in a second procedure, such as a second procedure performed at least one week after the first procedure. The target tissue can comprise at least duodenal mucosa tissue, such as to treat diabetes of a patient.

According to another aspect of the present inventive concepts, a method of treating tissue is performed using any of the systems and/or devices described herein.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 4A, 4B and 4C are perspective, side and end views, respectively, of an expandable element comprising a balloon, consistent with the present inventive concepts.

FIG. 7 is a chart showing the number of patients receiving numbers of treatments.

FIG. 8 is a table of cumulative demographic information.

FIG. 9 is a table showing results of applicant's studies.

FIG. 25 is a graph showing the average change in HbA1C from baseline in patients with LS-DMR and SS-DMR.

FIGS. 26A and 26B are graphs showing the average fasting plasma glucose in LS-DMR patients with a baseline HbA1C between 7.5% and 10%.

DETAILED DESCRIPTION OF THE DRAWINGS

Figure 1:
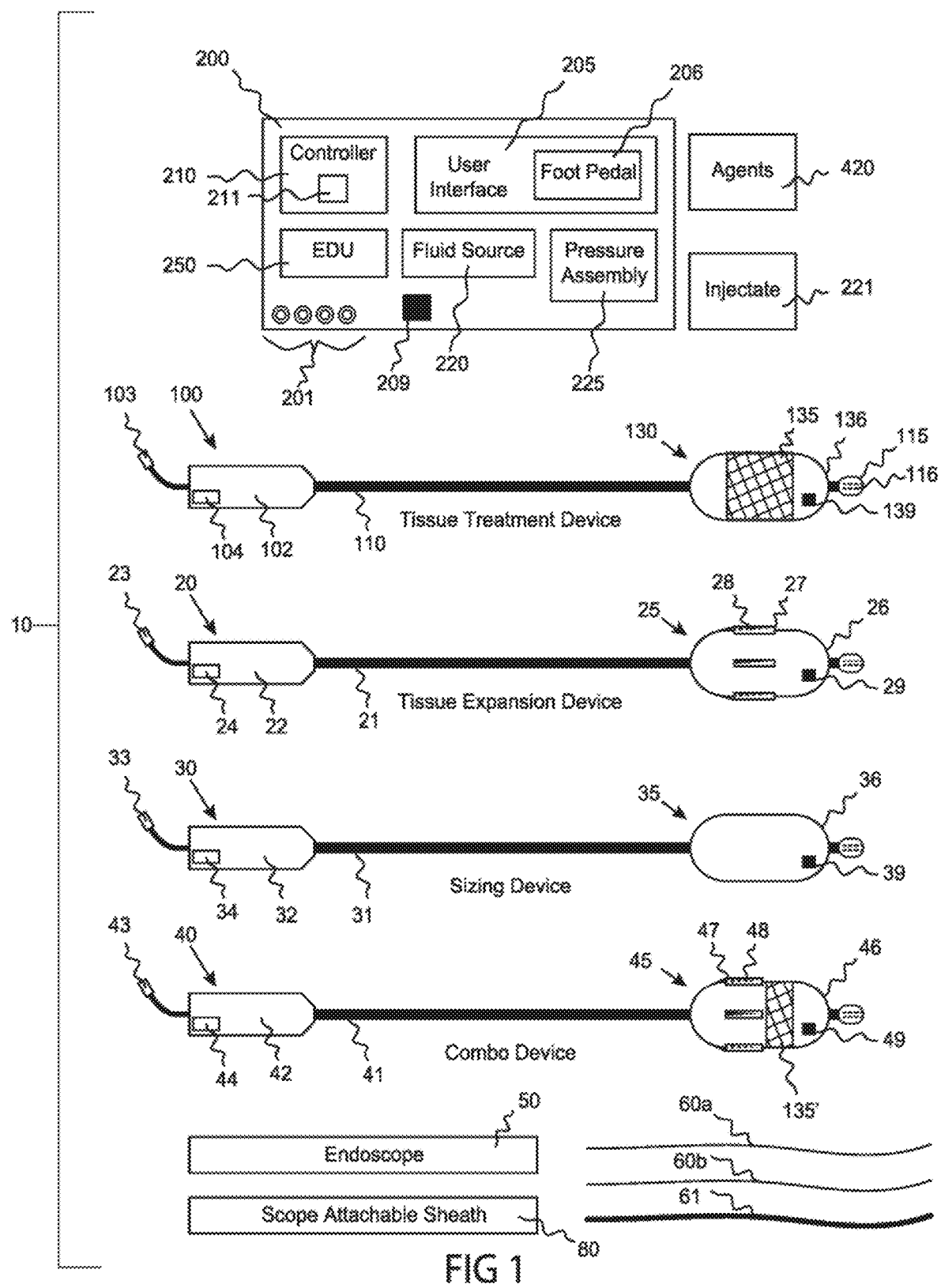
FIG. 1 is a schematic view of a system for treating target tissue of a patient, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove. As used herein, the term "vacuum level" refers to a measure of a vacuum wherein the lower the pressure, the greater the vacuum level.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

As used herein, the term "ablative fluid" refers to one or more liquids, gases, gels or other fluids whose thermal properties (at sufficiently high or low temperatures) cause tissue necrosis and/or another desired tissue modification. Alternatively or additionally, "ablative fluid" refers to one or more fluids whose chemical properties (at room temperature, body temperature or otherwise) cause tissue necrosis or another desired tissue treatment. The tissue treatment element of the present inventive concepts can comprise one or more ablative fluids.

It is an object of the present inventive concepts to provide systems, methods and devices for safely and effectively treating a volume of tissue (the "target tissue"), such as to treat a patient disease or disorder. Target tissue can comprise one or more target tissue segments or other target tissue portions. The target tissue can comprise one or more layers of a portion of tubular or non-tubular tissue, such as tissue of an organ or tissue of the gastrointestinal (GI) tract of a patient. The systems and devices of the present inventive concepts can include one or more treatment assemblies and/or treatment elements configured to treat target tissue, such as a treatment element comprising fluid at an ablative temperature delivered to a balloon (ablative temperature fluid and/or balloon filled with ablative fluid each referred to singly or collectively as a "treatment element" of the present inventive concepts). One or more treatment elements can be provided in, on and/or within an expandable treatment assembly or other radially deployable mechanism. The treatment assemblies and/or treatment elements are configured to treat target tissue (e.g. deliver energy to target tissue), such as to modify target tissue (e.g. to modify the secretions from the target tissue and/or absorption of the target tissue), ablate target tissue (e.g. to cause the replacement of the target tissue with "new tissue") and/or to cause a reduction in the surface area of target tissue (e.g. the luminal surface area of an inner wall of tubular tissue) at or proximate to one or more locations where the treatment was performed (e.g. proximate the location where energy was delivered). The luminal or other tissue treatment can occur acutely and/or it can take place over time such as days, weeks or months. A tissue surface area reduction can correspond to a reduction in mucosal surface area available to function in an absorptive and/or a secretory capacity. A target tissue treatment can result in the replacement of target tissue with new tissue with different absorptive and/or secretory capacity and/or other desirable effect related to replacement and/or modification of target tissue. The treatment of target tissue with the systems, devices and methods of the present inventive concepts can provide a therapeutic benefit to the patient, such as to treat one or more diseases or disorders of the patient, as described in detail herebelow.

Each treatment assembly can comprise at least one tissue treatment element such as a tissue treatment element selected from the group consisting of an ablative fluid delivered to a balloon or other expandable fluid reservoir; an energy delivery element mounted to an expandable assembly such as an electrode or other energy delivery element configured to deliver radiofrequency (RF) energy and/or microwave energy; a light delivery element configured to deliver laser or other light energy; a fluid delivery element configured to deliver ablative fluid directly onto tissue; a sound delivery element such as a ultrasonic and/or subsonic sound delivery element; and combinations of these. Numerous forms of treatment assemblies and/or treatment elements can be included. In some embodiments, the treatment assemblies and/or the one or more treatment elements contained therein are configured as described in: applicant's co-pending U.S. patent application Ser. No. 13/945,138, entitled "Devices and Methods for the Treatment of Tissue", filed Jul. 18, 2013; applicant's co-pending U.S. patent application Ser. No. 14/470,503, entitled "Heat Ablation Systems, Devices and Methods for the Treatment of Tissue", filed Aug. 27, 2014; applicant's co-pending U.S. patent application Ser. No. 14/609,332, entitled "Electrical Energy Ablation Systems, Devices and Methods for the Treatment of Tissue", filed Jan. 29, 2015; and/or applicant's co-pending U.S. patent application Ser. No. 14/609,334, entitled "Ablation Systems, Devices and Methods for the Treatment of Tissue", filed Jan. 29, 2015; the contents of each of which is incorporated herein by reference in its entirety.

The treatment assemblies and/or treatment elements of the present inventive concepts can deliver treatment (e.g. deliver energy, deliver a chemically ablative fluid, mechanically abrade and/or otherwise treat tissue) to a particular area of tissue, the "delivery zone". During a single delivery of treatment, a treatment element can be constructed and arranged to deliver treatment to a relatively continuous surface of tissue (e.g. a continuous surface of tissue in contact with a balloon filled with ablative fluid or a surface of tissue onto which a chemically ablative fluid is sprayed, coated or otherwise delivered). In these continuous-surface treatment delivery embodiments, the delivery zone comprises the continuous surface of tissue receiving the treatment directly. Alternatively, a treatment element can be constructed and arranged to deliver treatment to multiple discrete portions of a tissue surface, with one or more tissue surface portions in-between other surface portions that do not receive energy or other treatment from the treatment element. In these segmented-surface treatment delivery embodiments, the delivery zone is defined by a periphery of the multiple tissue surface area portions receiving treatment, similar to a "convex hull" or "convex envelope" used in mathematics to define an area including a number of discrete locations that define a periphery. A delivery zone can comprise two or more contiguous or non-contiguous delivery zones, and multiple delivery zones can be treated sequentially and/or simultaneously.

For example, in embodiments where the treatment element is hot fluid (e.g. ablative fluid at a sufficiently high temperature to cause tissue necrosis) positioned within a balloon, the delivery zone comprises all tissue surfaces contacted by the balloon that directly receive ablative thermal energy from the ablative fluid through the balloon. In embodiments, where the treatment element is a balloon filled with cold fluid (e.g. ablative fluid at a sufficiently low temperature to cause tissue necrosis), the delivery zone can comprise all tissue surfaces contacted by the balloon that have heat extracted from them by the cold fluid (e.g. at a sufficient cold temperature to treat the tissue). In embodiments where the treatment element is an array of electrodes configured to deliver electrical energy (e.g. RF energy) to tissue, the delivery zone can comprise an area defined by the electrodes on the periphery of the array (e.g. a convex hull as described above), such as when the electrodes are positioned and energy is delivered to treat relatively the entire surface of tissue within the periphery. In embodiments where the treatment element comprises one or more fluid delivery elements delivering ablative fluid directly to tissue (e.g. an ablative fluid whose chemical nature modifies tissue, at body temperature or otherwise), the delivery zone can comprise a surface defined by the periphery of tissue locations receiving the ablative fluid, such as when the ablative fluid is delivered (e.g. sprayed or otherwise applied, such as via a sponge) to relatively the entire surface within the periphery. In embodiments where the treatment element comprises one or more light delivery elements such as those that deliver laser energy to tissue, the delivery zone can comprise a surface area defined by the periphery of tissue locations receiving the light energy, such as when light is delivered at a set of locations and with a magnitude of energy configured to treat relatively the entire surface of tissue within the periphery. In these embodiments, light can be delivered to relatively the entire energy delivery zone, or to a large number (e.g. greater than 100) of tissue locations within the periphery of the delivery zone (e.g. making up less than 50%, less than 20% or less than 10% of the total surface area of the delivery zone). In embodiments where the treatment element comprises one or more sound delivery elements such as those that deliver sub-sonic and/or ultrasonic sound energy to tissue, the delivery zone can comprise a surface area defined by the periphery of tissue locations receiving the sound energy, such as when ablative sound energy is delivered at a set of locations and with a magnitude of energy configured to treat relatively the entire surface of tissue within the periphery. In embodiments in which the treatment element comprises a mechanical cutter or other abrasion element, the delivery zone can comprise a surface defined by all tissue dissected, cut, mechanically disrupted and/or otherwise modified during a single abrading step of the mechanical abrader.

A delivery zone can comprise a cumulative set of delivery zones that receive treatment simultaneously or sequentially, by one or more tissue treatment elements, such as those described immediately hereabove. A delivery zone can comprise a first delivery zone defined when a treatment element treats target tissue in a first treatment delivery, plus a second delivery zone defined when the treatment element treats target tissue in a second treatment delivery, and so on. In these embodiments, the treatment element can be translated, rotated and/or otherwise repositioned between treatment deliveries, where each delivery zone is associated with the position of the treatment element during each treatment delivery. Multiple delivery zones can receive treatment in a single procedure, such as within a period of less than twenty-four hours. A delivery zone can comprise a set of multiple delivery zones treated by two or more treatment elements.

Target tissue treated by each energy delivery and/or other treatment delivery comprises the tissue directly receiving treatment (i.e. the tissue defined by the delivery zone) plus "neighboring tissue" which is also modified by the associated treatment delivery. The neighboring tissue can comprise tissue alongside, below and/or otherwise proximate the delivery zone tissue. The neighboring tissue treatment can be due to one or more of: conduction or convection of heat or cold from the delivery zone; flow of ablative fluid from the delivery zone; flow of toxins or other agents that occur during cell degradation and/or death; radiation; luminescence, light dissipation; and other energy and/or chemical propagation mechanisms. In some embodiments, an area (i.e. the delivery zone) comprising an inner surface of mucosal tissue directly receives treatment from one or more treatment elements (e.g. an ablative fluid contained within a balloon), and the total volume of target tissue treated by that single treatment delivery includes: the delivery zone tissue (i.e. surface mucosal tissue directly receiving energy and/or other treatment from the treatment element); surface mucosal tissue in close proximity (e.g. adjacent) to the delivery zone tissue; and mucosal and potentially submucosal tissue layers beneath (deeper than) the delivery zone tissue and the treated adjacent surface mucosal tissue.

In some embodiments, a "treatment neutralizing" procedure is performed after one or more treatment deliveries, such as a treatment neutralizing cooling procedure performed after one or more treatment elements deliver or otherwise generate heat to treat target tissue, or a treatment neutralizing warming procedure performed after one or more treatment elements deliver cryogenic energy to treat target tissue. In these embodiments, the treatment neutralizing cooling or warming fluid can be delivered to the same expandable assembly (e.g. an expandable assembly comprising a balloon) delivering the heat or cryogenic treatment, respectively, and/or the neutralizing fluid can be delivered directly to tissue. In some embodiments, a treatment element delivers an ablating agent to target tissue (e.g. a chemical or other agent configured to cause target tissue necrosis or otherwise treat target tissue), and a treatment neutralizing procedure comprises delivery of a neutralizing agent to target and/or non-target tissue to reduce continued ablation due to the delivered caustic ablative fluid (e.g. a base to neutralize a delivered acid or an acid to neutralize a delivered base).

Each treatment assembly and/or treatment element of the present inventive concepts can be configured to treat target tissue in one or more locations of the patient, such as one or more contiguous or discontiguous tissue locations. The target tissue comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. "Non-target tissue" can be identified (e.g. prior to and/or during the medical procedure), wherein the non-target tissue comprises tissue whose treatment by the treatment assembly and/or treatment element should be reduced or avoided such as to reduce or prevent an undesired effect to the patient.

The target tissue treatment can cause one or more modifications of the target tissue such as a modification selected from the group consisting of: modification of cellular function; cell death; apoptosis; instant cell death; cell necrosis; denaturing of cells; removal of cells; and combinations of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit. The modified and/or replacement tissue can have different secretions and/or quantities of secretions than the pre-treated target tissue, such as to treat diabetes, hypercholesterolemia and/or another patient disease or disorder. The modified and/or replacement tissue can have different absorptive properties than the target tissue, such as to treat diabetes, insulin resistance, hypercholesterolemia and/or another patient disease or disorder. The modified and/or replacement tissue can have a different surface topography than the target tissue, such as a modification of the topography of the inner wall of the GI tract that includes a smoothing or flattening of its inner surface, such as a modification in which the luminal surface area of one or more segments of the GI tract (e.g. one or more duodenal segments) is reduced after treatment. The effect of the treatment can occur acutely, such as within twenty-four hours, or after longer periods of time such as greater than twenty-four hours or greater than one week.

Target tissue to be treated can comprise two or more discrete tissue segments, such as two or more axial segments of the GI tract. Each tissue segment can comprise a full or partial circumferential segment of the tissue segment. Multiple tissue segments can be treated with the same or different treatment elements, and they can be treated simultaneously or in sequential steps (e.g. sequential energy delivery steps that deliver energy to multiple delivery zones). Multiple tissue segments can be treated in the same or different clinical procedures (e.g. procedures performed on different days). In some embodiments, a series of tissue segments comprising a series of axial segments of the GI tract (e.g. a series of axial segments of the duodenum) are treated in a single clinical procedure. The first and second tissue segments can be directly adjacent, they can contain overlapping portions of tissue, and there can be gaps between the segments. Dissimilarities in treatment elements can include type and/or amount of energy to be delivered by an energy delivery based treatment element. Dissimilarities in target tissue treatments can include: target tissue area treated; target tissue volume treated; target tissue length treated; target tissue depth treated; target tissue circumferential portion treated; ablative fluid type, volume and/or temperature delivered to a treatment element comprising a reservoir such as a balloon; ablative fluid type, volume and/or temperature delivered directly to tissue; energy delivery type; energy delivery rate and/or amount; peak energy delivered; average temperature of target tissue achieved during target tissue treatment; maximum temperature achieved during target tissue treatment; temperature profile of target tissue treatment; duration of target tissue treatment; surface area reduction achieved by target tissue treatment; and combinations of these.

Target tissue can include tissue of the duodenum, such as tissue including substantially all or a portion of the mucosal layer of one or more axial segments of the duodenum (e.g. including all or a portion of the plicae circulares), such as to treat diabetes, hypercholesterolemia and/or another patient disease or disorder, such as while leaving the duodenum anatomically connected after treatment. Target tissue can include one or more portions of a tissue layer selected from the group consisting of: mucosa; mucosa through superficial submucosa; mucosa through mid-submucosa; mucosa through deep-submucosa; and combinations of these. Replacement tissue can comprise cells that have migrated from one or more of: gastric mucosa; jejunal mucosa; an untreated portion of the duodenum whose mucosal tissue functions differently than the treated mucosal tissue functions prior to treatment; and combinations of these. Replacement tissue can include one or more tissue types selected from the group consisting of: scar tissue; normal intestinal mucosa; gastric mucosa; and combinations of these. In some embodiments, target tissue includes a treatment portion comprising the mucosal layer of the duodenum, and a safety-margin portion comprising a near-full-depth or partial-depth layer of the submucosal layer of the duodenum. In some embodiments, the target tissue comprises nearly the entire mucosal layer of the duodenum, and can include a portion of the pylorus contiguous with the duodenal mucosa and/or a portion of the jejunum contiguous with the duodenal mucosa. In some embodiments, the target tissue comprises all or a portion of the duodenal mucosa distal to the ampulla of Vater, such as when tissue within 0.5 cm or within 1 cm of the ampulla of Vater is not ablated or otherwise treated. In these embodiments, the target tissue can comprise at least 10%, at least 15%, at least 25%, at least 30% or at least 50% of the duodenal mucosa distal to the ampulla of Vater. Alternatively or additionally, the target tissue can comprise no more than 70% or no more than 90% of the duodenal mucosa distal to the ampulla of Vater. In these embodiments, tissue proximal to and/or proximate the ampulla of Vater can comprise non-target tissue (i.e. tissue whose treatment is avoided or at least reduced).

In some embodiments, the target tissue comprises at least a portion of duodenal mucosal tissue, and the systems, methods and devices of the present inventive concepts are configured to counteract duodenal mucosal changes that cause an intestinal hormonal impairment leading to insulin resistance in patients. In these embodiments, the therapy provided can improve the body's ability to process sugar and dramatically improve glycemic control for patients with insulin resistance and/or Type 2 diabetes.

Hormones released from the intestinal mucosa play an important role in modulating glucose homeostasis, and different axial segments of the intestinal mucosa release different hormones in the fasting and post-prandial state in order to modulate blood glucose in the fasting and post-prandial states, respectively. After a meal, the proximal intestinal mucosa senses the intestine for ingested glucose and release a collection of hormones in response to this signal. These hormones initiate the process of insulin release into the bloodstream after a meal, but they also induce some insulin resistance to prevent the released insulin from causing hypoglycemia before the body has a chance to absorb the ingested glucose. One such hormone that plays a role in this is GIP. The net effect of distal gut hormones released in response to a meal, on the contrary, is to both allow the release of more insulin but also play a role in helping the body now become sensitive to its circulating insulin. Teleologically, the explanation for this difference is that enough glucose will have been absorbed by the time nutrients reach the distal intestine to allow the insulin to begin to function to reduce blood glucose levels (e.g. without significantly risking hypoglycemia).

In patients with Type 2 Diabetes, a lifetime of exposure to fat and sugar can have led to intestinal changes predominantly in the proximal intestine. These changes are characterized by an excess proximal intestinal hormonal contribution to the fasting and post-prandial glucose homeostasis. The net result of these intestinal changes is to create a condition of insulin resistance and impaired glucose tolerance. Treatment of duodenal mucosal tissue with the systems, devices and methods of the present inventive concepts can be performed to alter the intestinal mucosal hormone production from the region of treated tissue. The treated tissue can then have an altered hormonal secretion pattern that affects blood glucose levels in the fasting and post-prandial states. The tissue treatment of the present inventive concepts can be performed to effect duodenal mucosal tissue secretion of GIP and/or GLP-1. The tissue treatment can lead to changes in the blood levels of GIP and/or GLP-1 (and other gut hormones) that can lead to changes in glucose homeostasis in the fasting and/or post-prandial states. The treatment can lead to changes in insulin and/or glucagon secretion from the pancreas and/or insulin and/or glucagon levels in the bloodstream. The treatment can lead to changes in pancreatic beta cell function and/or health through direct hormonal consequences of the treated duodenal tissue and/or indirectly through improved blood glucose levels.

Treatment of duodenal mucosal tissue can be performed to treat a disease and/or disorder selected from the group consisting of: diabetes; pre-diabetes; impaired glucose tolerance; insulin resistance; obesity or otherwise being overweight; a metabolic disorder and/or disease; and combinations of these. In some embodiments, treatment of duodenal mucosal tissue can be performed to treat a disease and/or disorder selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease (e.g. as a secondary prevention); stroke/TIA; cognitive decline or dementia (e.g. Alzheimer's); diabetic nephropathy; neuropathy; retinopathy; diabetic heart disease and/or heart failure. A near full circumferential portion (e.g. approximately 360°, hereinafter "full circumferential") of the mucosal layer of one or more axial segments of GI tissue can be treated. In some embodiments, less than 360° of one or more axial segments of tubular tissue is treated, such as one or more circumferential portions less than 350°, or between 300° and 350°, such as to prevent a full circumferential scar from being created at the one or more axial segment locations.

Target tissue can be selected to treat two or more patient diseases or disorders, such as two or more patient diseases or disorders as described herein.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise tissue selected from the group consisting of: large and/or flat colonic polyps; margin tissue remaining after a polypectomy; and combinations of these. These tissue locations can be treated to treat residual cancer cells.

Target tissue can comprise esophageal tissue and/or gastric tissue. In some embodiments, target tissue comprises cancerous or precancerous tissue treated with a single or multiple energy deliveries, in single or multiple clinical procedures. In some embodiments, target tissue is treated as a treatment of Barrett's esophagus.

Target tissue can comprise at least a portion of the intestinal tract afflicted with inflammatory bowel disease, such that Crohn's disease and/or ulcerative colitis can be treated.

Target tissue can comprise GI tissue selected to treat Celiac disease and/or to improve intestinal barrier function.

The treatment assemblies, treatment elements, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater (also known as the papilla); pancreas; bile duct; pylorus; and combinations of these.

In some embodiments, two or more clinical procedures are performed in which one or more volumes of target tissue are treated in each clinical procedure, such as is described in applicant's co-pending U.S. patent application Ser. No. 14/673,565, entitled "Methods, Systems and Devices for Performing Multiple Treatments on a Patient", filed Mar. 30, 2015. For example, a second clinical procedure can be performed at least twenty-four hours after the first clinical procedure, such as a second clinical procedure performed within 6 months of a first clinical procedure or a clinical procedure performed after at least 6 months after the first clinical procedure. The first and second clinical procedures can be performed using similar or dissimilar methods, and they can be performed using similar or dissimilar systems and/or devices (e.g. performed with similar or dissimilar treatment elements). The first and second clinical procedures can treat similar or dissimilar volumes of target tissue (e.g. similar or dissimilar amounts of tissue treated and/or locations of tissue treated), and they can deliver energy to similar or dissimilar sets of multiple delivery zones. In some embodiments, the first and second clinical procedures can include treating and/or delivering energy to contiguous and/or overlapping regions of the GI tract either in the circumferential and/or axial dimensions. In other embodiments, the first and second clinical procedures can include the treatment of disparate regions of the GI tract (such as disparate regions of the duodenum, ileum, and/or stomach). The first and second clinical procedures can be performed using similar or dissimilar treatment devices. The first and second clinical procedures can comprise similar or dissimilar deliveries of energy to treat the target tissue. The first and second clinical procedures can be performed at similar or dissimilar temperatures. The second clinical procedure can be performed based on diagnostic results collected after the first clinical procedure has been performed.

The treatment assemblies, treatment elements and other functional elements of the present inventive concepts can be configured to automatically and/or manually expand or traverse in at least one radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of these. In some embodiments, the expandable elements can comprise a radially expandable tube, such as a sheet of material resiliently biased in a radially expanded condition that can be compacted through a furling operation, or a sheet of material resiliently biased in a radially compact condition that can be expanded through an unfurling operation. The expandable elements can comprise a foldable sheet, such as a sheet configured to be folded to be radially compacted and/or to be unfolded to radially expand. In some embodiments, the expandable elements expand to contact tissue, such as to expand to a diameter similar to the diameter of the luminal wall tissue into which the expandable element has been placed. In some embodiments, the expandable elements expand to be closer to wall tissue, but remain at a distance (e.g. a fixed or pre-determined distance) from the tissue surface, such as when the tissue is subsequently brought into contact with all or a portion of the expanded assembly (e.g. using insufflation fluid withdrawal techniques). In some embodiments, the expandable elements expand to be larger than the diameter of the luminal wall tissue into which the expandable element has been placed, such as to improve the quality of the apposition of the expandable element against the uneven surface of the tissue. In these embodiments, the fully expanded diameter of the expandable elements would be configured to avoid a diameter large enough to cause lasting mechanical damage to the apposed tissue and/or to tissue proximate the apposed tissue. In some embodiments, the expansion of an expandable assembly is monitored and/or varied (e.g. decreased and/or increased), such as to accommodate or otherwise compensate for peristalsis or other muscle contractions that occur in the GI tract (e.g. contractions that occur when a foreign body is present in the GI tract) and/or varied to accommodate changes in GI lumen diameter imposed by aspects of the procedure itself.

Any device of the present inventive concepts can include one or more treatment elements configured to deliver energy to one or more delivery zones, to treat at least a portion of target tissue. Any device can include one or more fluid delivery elements, such as one or more nozzles or needles configured to deliver fluid toward and/or into tissue. The fluid delivery elements can be constructed and arranged to deliver fluid to perform a function selected from the group consisting of: expanding one or more tissue layers; warming or cooling tissue; removing debris or other substance from a tissue surface; delivering energy to a delivery zone comprising a continuous or segmented surface; treating target tissue; and combinations of these. Any of the expandable assemblies of the present inventive concepts can include one or more other functional elements, such as are described in reference to the figures herebelow. The treatment elements, fluid delivery elements, and/or other functional elements can be mounted on, within (e.g. within the wall) and/or inside of an expandable element such as a balloon or expandable cage. In some embodiments, one or more functional elements is not mounted to an expandable element, such as those attached to a shaft or other non-expandable treatment device component.

In some embodiments, the treatment device comprises at least one treatment element configured to deliver energy to a delivery zone such as to ablate target tissue. Examples of ablation elements include but are not limited to: ablative fluids, such as hot or cold ablative fluids delivered to a balloon and/or directly to target tissue; one or more fluid delivery elements configured to deliver ablative fluid directly to target tissue; an RF and/or microwave energy delivery element such as one or more electrodes; an ultrasonic and/or subsonic transducer such as one or more piezo crystals configured to ablate tissue with ultrasonic or subsonic, respectively, sound waves; a laser energy delivery element such as one or more optical fibers, laser diodes, prisms and/or lenses; a rotating ablation element; a circumferential array of ablation elements; and combinations of these.

The expandable elements comprising balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation (i.e. the balloon becomes inflated only after a minimum fluidic pressure is applied to the interior of the balloon); and a second sub-category, wherein the balloon expands elastically until an elastic limit is reached which effectively restricts the balloon diameter to a maximum value. The individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment (e.g. during operation a desired balloon diameter can be achieved by adjustment of a combination of fluid temperature and pressure); a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or device are configured to circulate a flow of fluid through the balloon (e.g. an elastic balloon or an inelastic balloon) at a sufficiently low enough pressure to prevent apposition of the balloon or other device component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i.e. minimal heat loss to the fluid path components due to the pre-heating or pre-cooling). These configurations provide a method of delivering energy to tissue with an ablative fluid filled balloon. A "thermal priming" procedure can be performed prior to one or more target tissue treatments, such as to improve thermal response time of one or more portions of the treatment device. Ablative fluid filled balloon treatment devices as well as thermal priming devices and methods can be configured as is described in applicant's co-pending U.S. application Ser. No. 14/470,503, entitled "Heat Ablation Systems, Devices and Methods for the Treatment of Tissue", filed Aug. 27, 2014, the contents of which is incorporated herein by reference in its entirety.

A fluid evacuation procedure can be performed on one or more internal locations of the treatment devices and/or treatment elements of the present inventive concepts, such as when a negative pressure is applied to purge or otherwise evacuate fluid from one or more locations. A fluid evacuation procedure can be performed prior to a thermal priming procedure and/or prior to delivering ablative fluid to a treatment element.

At times during target tissue treatment when it is desirable to initiate, increase and/or otherwise modify the treatment of tissue by one or more tissue treatment elements (e.g. a fluid delivery element delivering ablative fluid, a mechanically abrasive element, a hot or cold fluid balloon delivering a thermal energy to tissue and/or an electrode delivering RF energy), the diameter of the treatment assembly and/or treatment element (e.g. the diameter of a balloon, deployable cage, expandable tube or other expandable assembly) can be increased in situ to move a treatment element closer to target tissue and/or to change the contact force between the treatment element and the target tissue. At times during treatment when it is desirable to stop or otherwise decrease the amount of tissue treatment, the diameter of the treatment assembly and/or treatment element can be reduced in situ, such as to prevent or at least reduce delivery of energy or other treatment to the target tissue by eliminating or reducing tissue contact of one or more treatment elements (e.g. electrodes, abrasive surfaces or ablative fluid-filled balloons). For those cases where the native diameter of the target tissue varies substantially within a delivery zone, a highly elastic or compliant balloon or other expandable element can be employed, such as a balloon or deployable cage which can be adjusted to achieve a wide range of operating diameters.

Alternatively or additionally, to initiate, increase and/or otherwise modify the treatment of tissue by one or more treatment elements (e.g. a fluid delivery element delivering ablative fluid, a mechanically abrasive element, a hot or cold fluid balloon delivering thermal energy to or from tissue and/or an electrode delivering RF energy), the diameter of the target tissue can be decreased in situ to move target tissue closer to a treatment element and/or to change the contact force between the target tissue and the treatment element. To stop or otherwise decrease ablation of tissue, the diameter of tissue neighboring a treatment element can be increased in situ, such as to prevent or reduce delivery of energy or other treatment to the target tissue by eliminating or reducing tissue contact of one or more treatment elements (e.g. electrodes, abrasive surfaces or ablative fluid filled balloons). The diameter of the tissue proximate a treatment element can be increased or decreased, independent of the treatment assembly diameter, by means of delivering and/or withdrawing a fluid, to and/or from a lumen surrounded by target tissue, such as by using standard GI insufflation techniques. Typical insufflation fluids include but are not limited to: gases such as carbon dioxide or air; liquids such as water or saline solution; and combinations of these. The insufflation fluids can be introduced through a treatment device, through an endoscope such as an endoscope through which the treatment device is inserted, and/or via another device placed proximate the target tissue. Delivery of insufflation fluids can be performed to move target tissue away from one or more treatment elements, such as to stop transfer of energy to target tissue at the end of a treatment of target tissue as described hereabove. Alternatively or additionally, delivery of insufflation fluids can be performed to manipulate tissue, such as to distend and/or elongate tissue. Removal of these insufflation fluids and/or the application of a vacuum or other negative pressure can be used to decrease the diameter of the target tissue, such as to bring the target tissue in closer proximity to one or more treatment elements and/or to increase the contact force between target tissue and one or more treatment elements, also as described hereabove. In this tissue diameter controlled approach, a treatment assembly including a balloon that can be maintained at a substantially constant diameter can be desirable, such as a substantially inelastic balloon such as a balloon with an elastic-limit.

The systems of the present inventive concepts can include one or more tissue expansion devices that comprise one or more fluid delivery elements, such as one or more needles and/or fluid jets configured to deliver one or more fluids or other injectates to tissue, such as to expand target tissue and/or tissue proximate the target tissue (e.g. safety margin tissue) prior to treatment of target tissue by a tissue treatment element. The expanded tissue layer acts as a safety volume of tissue, reducing the specificity of the treatment (e.g. ablation) required and/or the need to protect the underlying non-target tissue from damage. In some embodiments, a vacuum pressure can be used to manipulate tissue and/or to maintain proximity between a portion of a tissue expansion device and tissue. The vacuum can be provided by one or more vacuum sources, such as via one or more operator adjustable vacuum sources.

Referring now to FIG. 1, a schematic view of a system for treating a patient is illustrated, consistent with the present inventive concepts. System 10 can be constructed and arranged to perform the method described in FIG. 2 herebelow, such as to treat one or more patient diseases or disorders, also as described herebelow. System 10 comprises tissue treatment device 100 and console 200. Tissue treatment device 100 is constructed and arranged to treat target tissue, such as via the delivery of energy and/or an ablating agent to target tissue. Tissue treatment device 100 includes connector 103 which operably attaches to console 200 at one or more of ports 201 of console 200. In some embodiments, system 10 further comprises tissue expansion device 20 which is constructed and arranged to expand one or more layers of tissue, such as one or more layers of target tissue and/or one or more layers of tissue proximate target tissue (e.g. one or more layers of safety-margin tissue). In some embodiments, system 10 further comprises lumen diameter sizing device 30 which is constructed and arranged to collect information correlated to the diameter of a portion of tubular tissue (e.g. the one, two or more diameters of a GI lumen proximate target tissue). In some embodiments, system 10 comprises multi-function device 40, which is constructed and arranged to perform two or more functions selected from the group consisting of: tissue treatment (e.g. tissue ablation); tissue expansion; luminal diameter sizing; and combinations of these. In some embodiments, system 10 comprises multi-function device 40, and does not include one or more of: tissue treatment device 100, tissue expansion device 20 and/or sizing device 30.

System 10 can further comprise a body introduction device, such as a vascular introducer, laparoscopic port, and/or endoscope 50. System 10 can further comprise one or more guidewires, such as guidewires 60a and 60b (singly or collectively guidewire 60). In some embodiments, one or more guidewires 60 comprise a guidewire selected from the group consisting of: a Savary-Gilliard® 400 cm guidewire, a Dreamwire™ guidewire; a super stiff Jagwire™ guidewire; and/or a similar guidewire. In some embodiments, system 10 includes scope attached sheath 80. Sheath 80 can comprise an elongate hollow tube which attaches (e.g. in a side-by-side manner) at one or more points along endoscope 50. In some embodiments, sheath 80 comprises the Reach® overtube manufactured by U.S. Endoscopy, or similar.

Tissue treatment device 100, tissue expansion device 20, lumen diameter sizing device 30 and multi-function device 40 comprise handles 102, 22, 32 and 42, respectively. Handles 102, 22, 32 and 42 each comprise one or more controls, controls 104, 24, 34 and 44, respectively. Controls 104, 24, 34 and 44 are configured to allow an operator to control one or more functions of the associated device, such as a function selected from the group consisting of: inflate or otherwise expand an expandable assembly; deliver energy; modify energy delivery; deliver an insufflation fluid; insufflate a portion of the GI tract; desufflate a portion of the GI tract; deliver an injectate (e.g. into tissue and/or onto the surface of tissue); deliver a tissue expanding fluid (e.g. into tissue); steer the distal portion of a shaft; translate a control cable or control rod (hereinafter "control rod"); activate a sensor (e.g. record a signal); activate a transducer; activate a functional element; and combinations of these. In some embodiments, handles 102, 22, 32 and/or 42 can comprise a user interface configured to control one or more components of system 10, such as controls 104, 24, 34 and/or 44, respectively, each of which can be constructed and arranged to control operation of one or more of: device 100, device 20, device 30, device 40 and/or console 200. In some embodiments, controls 104, 24, 34 and/or 44 can comprise one or more user input and/or user output components, such as a component selected from the group consisting of: screen; touchscreen; light; audible transducer such as a beeper or speaker; tactical transducer such as a vibratory motor assembly; a keyboard; a membrane keypad; a switch; a safety-switch 206 such as a foot-activated switch; a mouse; a microphone; and combinations of these.

Handles 102, 22, 32 and 42 each attach to the proximal end of shafts 110, 21, 31 and 41, respectively. Shafts 110, 21, 31 and 41 each typically comprise a relatively flexible shaft comprising one or more internal lumens or other passageways. Shafts 110, 21, 31 and/or 41 can comprise a lumen, such as lumen 116 of shaft 110 shown, that are sized and configured to perform a function selected from the group consisting of: provide for the delivery or removal of one or more fluids such as ablation fluids, cooling fluids, insufflation fluids, pneumatic fluids, hydraulic fluids and/or balloon expanding fluids; allow over the guidewire delivery of the associated device; surround an electrical wire providing electrical energy and/or signals; surround an optical fiber; surround a fluid transport tube; slidingly receive a control shaft or other control filament such as a control filament used to expand or contract an expandable assembly or otherwise modify the shape of a portion of the device; and combinations of these. Shafts 110, 21, 31 and/or 41 can comprise a braided or otherwise reinforced shaft or can include one or more portions which are reinforced. Shafts 110, 21, 31 and/or 41 can comprise a multi-layer construction, such as a construction including a braid, a friction-reduced (e.g. PTFE) liner, a thermally insulating layer and/or an electrically insulating layer. Shafts 110, 21, 31 and/or 41 can include a bulbous distal end, such as bulbous tip 115 of shaft 110, a circular or oval shaped enlarged end configured to improve traversing the innermost tissue of the duodenum or other luminal tissue of the GI tract (e.g. to smoothly advance within a lumen whose walls include villi and/or one or more folds). As described hereabove, shafts 110, 21, 31 and/or 41 can include a guidewire lumen, such as lumen 116 of shaft 110.

Positioned on the distal end and/or on a distal portion of shafts 110, 21, 31 and 41 is an expandable tissue treatment assembly, expandable assemblies 130, 25, 35 and 45, respectively. Expandable assemblies 130, 25, 35 and 45 are each constructed and arranged to be radially expanded and subsequently radially compacted (each shown in their radially expanded state in FIG. 1), one or more times during use. Each of expandable assemblies 130, 25, 35 and 45 can include an expandable balloon, expandable cage, radially deployable arms and/or other expandable component.

In some embodiments, tissue treatment device 100, tissue expansion device 20, lumen diameter sizing device 30 and/or multi-function device 40, with their expandable assemblies 130, 25, 35 and 45 (respectively) in their radially compacted state, are sized and configured to be inserted through a working channel of endoscope 50 and/or sheath 80, after endoscope 50 and/or sheath 80 have been inserted into a patient (e.g. through the mouth and advanced such that their distal end resides in the duodenum or other GI tract location). In some embodiments, tissue treatment device 100, tissue expansion device 20, sizing device 30 and/or multi-function device 40 are sized and configured to be inserted through the mouth and into a patient's GI tract alongside endoscope 50. In some embodiments, tissue treatment device 100, tissue expansion device 20, lumen diameter sizing device 30 and/or multi-function device 40 are sized and configured to be inserted into a patient over one or more guidewires 60. For insertion over a guidewire, the shafts 110, 21, 31 and/or 41 and the distal portions of the associated device 100, 20, 30 and/or 40 can comprise sufficient flexibility to traverse the pylorus and enter the duodenum, while having sufficient column and torsional strength to be advanced through the duodenum. In some embodiments, one or more portions of the shafts 110, 21, 31 and 41 have variable stiffness (e.g. stiffer in a proximal portion of the shaft) and/or include a lumen configured to accept a stiffening wire, such as stiffening wire 61. Alternatively or additionally, stiffening wire 61 can be inserted into endoscope 50 and/or sheath 80, such as to facilitate their advancement through the stomach and into the duodenum.

Figure 6:
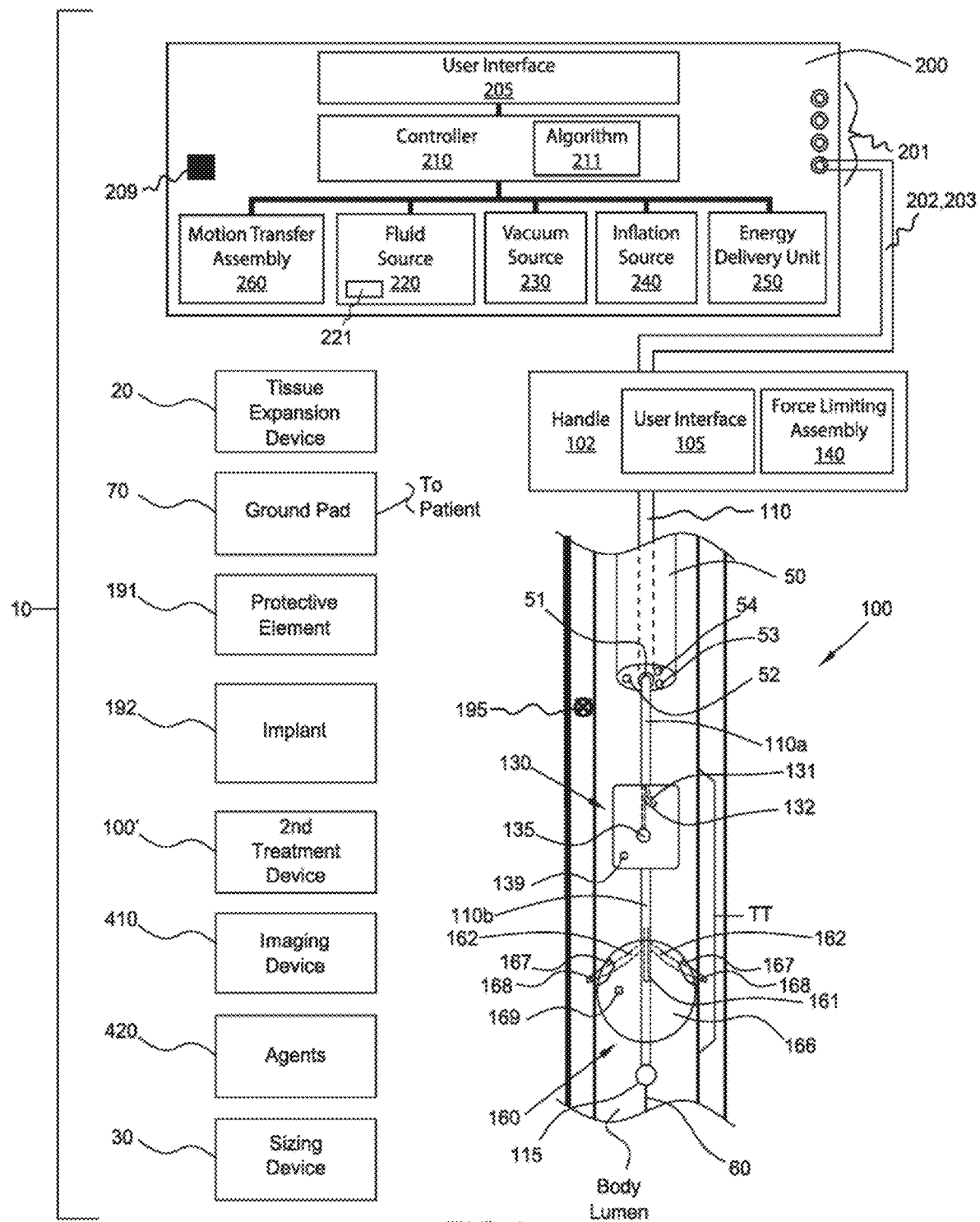
FIG. 6 is a schematic view of a system for treating target tissue of a patient, consistent with the present inventive concepts.

Console 200 can be constructed and arranged in a similar fashion to console 200 of FIG. 6 described herebelow. Console 200 can comprise an operator (e.g. clinician) accessible user interface 205. User interface 205 can comprise one or more user output and/or user input components, such as a component selected from the group consisting of: screen; touchscreen; light; audible transducer such as a beeper or speaker; tactical transducer such as a vibratory motor assembly; a keyboard; a membrane keypad; a switch; safety-switch 206 such as a foot-activated switch; a mouse; a microphone; and combinations of these.

Console 200 can comprise a controller, such as controller 210. Controller 210 can comprise one or more components or assemblies selected from the group consisting of: an electronics module; a power supply; memory; a microcontroller; a microprocessor; a signal analyzer; an analog to digital converter; a digital to analog converter; a sensor interface; transducer drive circuitry; software; and combinations of these. Controller 210 can comprise one or more algorithms 211, which can be constructed and arranged to automatically and/or manually control and/or monitor one or more devices, assemblies and/or components of system 10. Algorithm 211 of controller 210 can be configured to determine one or more tissue expansion and/or tissue treatment parameters. In some embodiments, algorithm 211 processes one or more sensor signals (e.g. signals from functional elements 139, 29, 39 and/or 49 described herebelow) to modify one or more of: volume of tissue expansion fluid delivered; rate of tissue expansion fluid delivery; temperature of tissue expansion fluid delivery; amount of ablative fluid delivered; rate of ablative fluid delivery; energy delivered; power of energy delivered; voltage of energy delivered; current of energy delivered; temperature of ablative fluid or energy delivered; device and/or treatment element location within the GI tract; expandable assembly pressure (e.g. balloon pressure); and combinations of these. Treatment element 135 can deliver energy to a surface of tissue, a delivery zone as described hereabove, which is a subset of the target tissue treated by that energy delivery (e.g. tissue beyond the delivery zone is also treated due to the conduction of heat or other energy to neighboring tissue). Algorithm 211 can comprise an algorithm configured to determine a delivery zone parameter such as a delivery zone parameter selected from the group consisting of: anatomical location of a delivery zone; size of a delivery zone; percentage of a delivery zone to receive energy; type of energy to be delivered to a delivery zone; amount of energy to be delivered to a delivery zone; and combinations of these. Information regarding a delivery zone parameter can be provided to an operator of system 10 (e.g. a clinician), such as via user interface 205. This information can be employed to set a delivery zone parameter, assist the operator in determining the completion status of the procedure (e.g. determining when the procedure is sufficiently complete) and/or to advise the operator to continue to treat a pre-specified area or volume of target tissue. The total area of treatment, number of delivery zones, and/or number of treatments during a particular procedure (any of which can be determined or otherwise assessed via algorithm 211) can be defined by clinical and/or demographic data of the patient.

Console 200 can comprise one or more reservoirs or other sources of fluid, such as fluid source 220. Fluid source 220 can be configured to provide fluid at an ablative temperature (e.g. sufficiently hot or cold to ablate tissue), a treatment neutralizing (e.g. warming or cooling) fluid configured to reduce ablative effects, an insufflation fluid, and/or other fluid. Console 200 can comprise an energy delivery unit, such as EDU 250, configured to deliver energy to treatment element 135 and/or one or more other components of system 10, such as one or more components of devices 100, 20, 30 and/or 40. Controller 210, fluid source 220 and/or EDU 250 can be constructed and arranged similar to controller 210, fluid source 220 and/or EDU 250, respectively, of FIG. 6 described herebelow.

Console 200 can comprise a pressure assembly, such as pressure assembly 225 constructed and arranged to deliver positive pressure or vacuum pressure (e.g. any pressure below another pressure as described hereabove) to one or more fluid delivery elements or fluid pathways (e.g. lumens) of system 10. Pressure assembly 225 can be constructed and arranged to provide and/or remove fluid to radially expand and/or radially compact, respectively, one or more expandable assemblies, such as expandable assemblies 130, 25, 35 and/or 45. Pressure assembly 225 can comprise one or more pumps or other fluid delivery mechanisms, and/or other pressure or vacuum generators. In some embodiments, pressure assembly 225 is constructed and arranged to provide a recirculating ablative fluid (e.g. hot or cold) to device 100 and/or device 40. In these embodiments, pressure assembly 225 can be constructed and arranged to further provide a recirculating "neutralizing fluid" (e.g. a cooling or warming fluid, respectively, to counteract the ablative effects of the previously circulated ablative fluid) to balloon 36 and/or 46, respectively. Pressure assembly 225 can be constructed and arranged similar to vacuum source 230 and/or inflation source 240 of FIG. 6 described herebelow.

Console 200 includes ports 201, which are operably attached to one or more of: user interface 205 (e.g. safety-switch 206 or another component of user interface 205), controller 210, fluid source 220 and/or pressure assembly 225. Ports 201 are constructed and arranged to operably attach (e.g. fluidly, electrically, optically, acoustically, mechanically and/or otherwise operably attach) to one or more of connectors 103, 23, 33 and 43 of devices 100, 20, 30 and 40, respectively. Console 200 can be constructed and arranged to deliver fluids and/or energy via ports 201 to one or more of devices 100, 20, 30 and 40. In some embodiments, an inflation fluid and/or a fluid at an ablative temperature is provided and/or recovered by console 200, such as a fluid at an ablative temperature delivered to expandable assembly 130 of tissue treatment device 100 and/or expandable assembly 45 of device 40. In some embodiments, insufflation, pneumatic and/or hydraulic fluids are delivered and/or recovered by console 200 via ports 201. In some embodiments, an injectate 221 is delivered by console 200, such as is described herebelow in reference to tissue expansion device 20 and multi-function device 40. In some embodiments, one or more control rods (not shown) are translated (e.g. advanced and/or retracted) within one or more lumens or other openings of device 100, 20, 30 and/or 40, such as to expand a cage, deploy a radially deployable arm, change the shape of an assembly, translate an assembly, rotate an assembly and/or otherwise control the position, shape and/or configuration of an assembly of system 10.

Console 200 can provide energy to, send information to and/or record a signal from one or more other elements of device 100, such as functional elements 139, 29, 39 and/or 49 described herebelow.

Tissue treatment device 100 is constructed and arranged to treat target tissue of a patient. In some embodiments, tissue treatment device 100 is constructed and arranged similar to tissue treatment device 100 or 100' of FIG. 6 described herebelow. Tissue treatment device 100 comprises handle 102 which attaches to a proximal end of shaft 110 and includes connector 103 for operable attachment to console 200 (e.g. at a port 201). Positioned on the distal end or on a distal portion of shaft 110 is expandable assembly 130. Expandable assembly 130 can comprise an energy delivery element or other treatment element 135, such as an energy delivery element configured to deliver thermal, electrical, light, sound and/or ablative chemical energy to target tissue.

In some embodiments, treatment element 135 comprises a mechanical abrader configured to treat tissue through abrasion. In some embodiments, expandable assembly 130 comprises a balloon 136 which can be configured to receive one or more expansion and/or ablative fluids. Balloon 136 can comprise a compliant balloon, a non-compliant balloon and/or a pressure-thresholded balloon, and/or balloon 136 can otherwise be constructed and arranged as described in detail hereabove. In some embodiments, balloon 136 is constructed and arranged similar to balloon 136 of FIGS. 4A-C, described herebelow.

Via connector 103, console 200 can provide and/or remove one or more fluids to and/or from one or more lumens or other flow pathways of device 100, such as fluid provided by fluid source 220 and/or propelled by (i.e. delivered and/or removed by) pressure assembly 225. Console 200, via EDU 250, can be configured to provide energy to one or more treatment elements of device 100, such as energy contained in fluid at an ablative temperature (hot and/or cold), electrical energy (e.g. RF or microwave energy), light energy (e.g. laser light energy), or sound energy (e.g. subsonic or ultrasonic sound energy). In some embodiments, console 200 provides a fluid configured to treat target tissue with direct contact, such as an ablating agent (e.g. a sclerosant or other chemically ablative agent) and/or a fluid at an ablative temperature, either or both delivered directly to a target tissue surface.

In some embodiments, treatment element 135 comprises a fluid at an ablative temperature provided by console 200. In these embodiments, treatment element 135 can comprise a sufficiently hot fluid that is introduced into balloon 136 for a first time period to ablate target tissue, after which cold fluid is introduced into balloon 136, for a second time period, to remove heat from tissue (e.g. remove heat from target tissue and/or non-target tissue to reduce the ablation effect). Alternatively treatment element 135 can comprise a sufficiently cold fluid that is introduced into balloon 136 for a first time period to ablate target tissue, after which a higher temperature fluid is introduced into balloon 136, for a second time period, to warm tissue (e.g. warm target tissue and/or non-target tissue to reduce the ablation effect). Both the ablative and ablation-reducing fluids can be provided by console 200. Alternatively or additionally, a cooling or warming fluid can be introduced prior to the delivery of the ablative fluid into balloon 136, as described herebelow. These fluids can be provided in a recirculating manner as described in applicant's co-pending application U.S. patent application Ser. No. 14/470,503, entitled "Heat Ablation Systems, Devices and Methods for the Treatment of Tissue", filed Aug. 27, 2014, the content of which is incorporated herein by reference in its entirety. Alternatively or additionally, these fluids can be provided in a single bolus manner as described in applicant's co-pending application International Patent Application Serial Number PCT/US2014/055514, entitled "Systems, Method and Devices for Treatment of Target Tissue", filed Sep. 12, 2014, the content of which is incorporated herein by reference in its entirety. In some embodiments, thermal ablation is performed using system 10 as described herebelow in reference to the method of FIG. 2, or the system 10 of FIG. 6.

In some embodiments, target tissue and/or tissue proximate the target tissue is cooled, heated and subsequently cooled again. In these embodiments, target tissue and/or tissue proximate the target tissue can be cooled during at least a portion of a first step, such as a first step including supplying a first fluid (e.g. a recirculating fluid) to expandable assembly 130 for a first time period (e.g. a duration of approximately 15-30 seconds), wherein the first fluid is supplied at a cooling temperature (e.g. continuously supplied by fluid source 220 at a temperature of approximately 5° C. to 25° C., such as between 10° C. and 25° C. or between 15° C. and 25° C.). In a subsequent second step, target tissue and/or tissue proximate the target tissue can be heated (e.g. ablated) during at least a portion of the second step, such as a second step including supplying a second fluid (e.g. a recirculating fluid) to expandable assembly 130 for a second time period (e.g. a duration of approximately 8-15 seconds), wherein the second fluid is supplied at a heat ablating temperature (e.g. continuously supplied by fluid source 220 at a temperature of approximately 85° C.-95° C.). In a subsequent third step, target tissue and/or tissue proximate the target tissue can be cooled during at least a portion of the third step, such as a third step including supplying a third fluid (e.g. a recirculating fluid) to expandable assembly 130 for a third time period (e.g. a duration of approximately 15-30 seconds), wherein the second fluid is supplied at a cooling temperature (e.g. continuously supplied by fluid source 220 at a temperature of approximately 5° C. and 25° C., such as between 10° C. and 25° C. or between 15° C. and 25° C.). In some embodiments, other temperatures and/or durations for each heating or cooling cycle are used. In some embodiments, the second time period in which a hot fluid is supplied to expandable assembly 130 comprises a time less than the first time period and/or the third time period. In some embodiments, the temperature of the fluid supplied to expandable assembly 130 during the first time period and/or the third time period is at least 18° C. less and/or least 60° less than the temperature of the fluid supplied to expandable assembly 130 during the second time period. In some embodiments, the first temperature and the third temperature comprise a similar temperature.

In some embodiments, treatment element 135 comprises one or more energy or other treatment delivery elements positioned in, on and/or within expandable assembly 130. Treatment element 135 can comprise one or more energy delivery elements configured to deliver energy to target tissue, such as an energy delivery element selected from the group consisting of: a fixed or recirculating volume of fluid at a high enough temperature to ablate tissue; a fixed or recirculating volume of fluid at a low enough temperature to ablate tissue; one or more thermal energy delivery elements such as one or more elements configured to deliver heat energy or cryogenic energy; an array of electrodes such as an array of electrodes configured to deliver radiofrequency (RF) energy; one or more electromagnetic energy delivery elements such as one or more elements configured to deliver microwave energy; one or more optical elements configured to deliver light energy such as laser light energy to tissue; one or more sound energy delivery elements such as one or more elements configured to deliver subsonic and/or ultrasonic sound energy; one or more chemical or other agent delivery elements; and combinations of these. In some embodiments, tissue treatment device 100 is constructed and arranged to deliver RF energy, such as is described in applicant's co-pending U.S. patent application Ser. No. 14/609,332, entitled "Electrical Energy Ablation Systems, Devices and Methods for the Treatment of Tissue", filed Jan. 29, 2015; and/or to deliver ablative fluid directly to tissue, such as is described in applicant's co-pending application U.S. patent application Ser. No. 14/609,334, entitled "Ablation Systems, Devices and Methods for the Treatment of Tissue", filed Jan. 29, 2015; the contents of which are each incorporated herein by reference in their entirety.

In some embodiments, tissue treatment device 100 is further constructed and arranged to provide geometric information (e.g. diameter information) of a luminal structure such as the duodenum. In these embodiments, device 100 and expandable assembly 130 can be constructed and arranged similar to expandable assembly 35 and lumen diameter sizing device 30 described herebelow.

In some embodiments, system 10 comprises one or more devices for expanding target tissue or tissue proximate target tissue, such as tissue expansion device 20. In some embodiments, target tissue to be treated comprises mucosal tissue and the tissue to be expanded comprises submucosal tissue proximate the mucosal tissue to be treated. In some embodiments, tissue expansion device 20 is constructed and arranged similar to device 20 or device 100 described herebelow in reference to FIG. 6. In some embodiments, tissue expansion device 20 is constructed and arranged similar to a tissue expansion device described in applicant's co-pending International Patent Application Serial Number PCT/US2015/022293, entitled "Injectate Delivery Devices, Systems and Methods", filed Mar. 24, 2015, the content of which is incorporated herein by reference in its entirety. Tissue expansion device 20 can be configured to expand a full or partial circumferential segment of luminal wall tissue, such as to expand one or more layers of submucosal tissue in the duodenum or other luminal portion of the GI tract. Tissue expansion device 20 can be configured to expand multiple segments of GI tract tissue, such as multiple relatively contiguous segments of submucosal tissue expanded as is described in detail herebelow in reference to FIG. 2.

Tissue expansion device 20 comprises handle 22 which attaches to a proximal end of shaft 21 and includes connector 23 for operable attachment to console 200. Positioned on the distal end or on a distal portion of shaft 21 is expandable assembly 25. Expandable assembly 25 can comprise an expandable cage, radially deployable arms and/or an expandable balloon such as balloon 26 shown. Balloon 26 can comprise a compliant balloon, a non-compliant balloon and/or a pressure-thresholded balloon, and/or balloon 26 can otherwise be constructed and arranged as described in detail hereabove. Balloon 26 can comprise a tissue-contacting length of between 20 mm and 26 mm, such as a tissue-contacting length of approximately 23 mm. Balloon 26 can comprise a wall thickness of between 0.0002" and 0.0010", such as a wall thickness of approximately 0.0005". Expandable assembly 26 can be configured to expand to a diameter between 27.5 mm and 37.5 mm, such as a diameter of approximately 32.5 mm. Expandable assembly 25 can be configured to be expanded via control 24 and/or via user interface 205 of console 200 (e.g. inflated and deflated by delivery and removal, respectively, of air, water and/or other fluids by console 200).

Expandable assembly 25 comprises one or more fluid delivery elements 28. The one or more fluid delivery elements 28 can each comprise an element selected from the group consisting of: needle such as a straight needle or a curved needle; waterjet (also referred to as fluid jet); iontophoretic fluid delivery element; and combinations of these. The one or more fluid delivery elements 28 are configured to deliver injectate 221 and/or another fluid to tissue when expandable assembly 25 is expanded (e.g. at least partially expanded with inflation fluid provided by console 200), positioning the fluid delivery elements 28 proximate (e.g. in contact with or close to) tissue to be expanded, such as luminal wall tissue of the GI tract.

The one or more fluid delivery elements 28 can be configured to be advanced (e.g. advanced into tissue) and retracted via control 24 of device 20. The one or more fluid delivery elements 28 can be positioned in one or more ports 27, as shown in FIG. 1. In some embodiments, a vacuum provided by console 200 causes tissue to enter each port 27, such that each fluid delivery element 28 can inject fluid (e.g. injectate 221) into the captured tissue (e.g. tissue positioned on and/or within port 27, and/or frictionally engaged by port 27). In some embodiments, tissue is captured within port 27 such that fluid delivery element 28 can inject fluid (e.g. injectate 221) into the captured tissue without fluid delivery element 28 having to extend radially beyond the associated port 27. By fluid delivery element 28 remaining within port 27, risk of fluid delivery element 28 and/or injectate 221 penetrating through the outer surface of the GI tract is prevented or at least significantly reduced. In these embodiments, fluid can be delivered into tissue by fluid delivery element 28 with or without advancement of fluid delivery element 28 into the captured tissue. In some embodiments, fluid delivery elements 28, ports 27 and/or other portions of tissue expansion device 20 are constructed and arranged similar to the tissue expansion devices described in applicant's co-pending International Patent Application Serial Number PCT/US2015/022293, entitled "Injectate Delivery Devices, Systems and Methods", filed Mar. 24, 2015, the content of which is incorporated herein by reference in its entirety.

In some embodiments, expandable assembly 25 comprises 3 or more fluid delivery elements 28 arranged in a circumferential pattern, such as 3 fluid delivery elements 28 arranged along a circumference and separated by approximately 120°. The multiple fluid delivery elements 28 can be configured to be advanced individually (e.g. via multiple controls 24), or simultaneously (e.g. via a single control 24). In some embodiments, two fluid delivery elements 28 are separated by approximately 180°. In some embodiments, four fluid delivery elements 28 are separated by approximately 90°.

In some embodiments, system 10 includes injectate 221 which can be provided by console 200 to device 20, and delivered into tissue by the one or more fluid delivery elements 28. Injectate 221 can comprise a material selected from the group consisting of: water; saline; a fluid with a dye such as a visible dye such as indigo carmine; methylene blue; India ink; SPOT™ dye; a gel; a hydrogel; a protein hydrogel; a fluid containing a visualizable media such as a media visualizable under X-ray such as a radiopaque powder (e.g. tantalum powder), ultrasound imaging and/or magnetic resonance imaging; and combinations of these.

In some embodiments, device 20 and/or console 200 are configured to reduce the fluid (e.g. liquid or gas) in balloon 26 as injectate 221 is delivered into tissue such as submucosal tissue, such as to prevent excessive force being applied to tissue proximate the expanding tissue (i.e. due to the decreasing luminal diameter proximate the expanding tissue in contact with balloon 26). In some embodiments, system 10 is constructed and arranged to inflate balloon 26 to a first target pressure, such as a pressure of approximately 0.7 psi. Injectate 221 is delivered via fluid delivery elements 28 to submucosal tissue (e.g. simultaneously or sequentially). Fluid contained within balloon 26 can be removed or added to maintain the pressure at or below a second target pressure, for example a pressure higher than the first target pressure such as a pressure between 0.8 psi and 0.9 psi. Fluid of up to 10 ml can be injected while maintaining the second target pressure (e.g. no more than the second target pressure) in the balloon (e.g. by decreasing the amount of fluid in the balloon to cause approximately 1 mm steps of diameter decrease of balloon 26).

In some embodiments, tissue expansion device 20 is further constructed and arranged to provide geometric information (e.g. diameter information) of one or more axial segments of a luminal structure such as the duodenum. In these embodiments, device 20 and expandable assembly 25 can be constructed and arranged similar to lumen diameter sizing device 30 and expandable assembly 35, respectively, described herebelow.

In some embodiments, system 10 comprises one or more separate devices for estimating or otherwise measuring (e.g. "sizing") the diameter of luminal tissue, such as lumen diameter sizing device 30. Sizing device 30 is constructed and arranged to be placed into one or more locations of the GI tract or other internal location of the patient and measure the diameter or other geometric parameter of tissue. In some embodiments, sizing device 30 is constructed and arranged similar to device 30 or device 100 described herebelow in reference to FIG. 6. Sizing device 30 can be configured to measure the diameter of multiple locations of GI tract tissue, such as multiple diameters along the length of one or more axial segments of the duodenum or other intestinal location.

Device 30 comprises handle 32 which attaches to a proximal end of shaft 31 and includes connector 33 for operable attachment to console 200. Positioned on the distal end or on a distal portion of shaft 31 is expandable assembly 35. Expandable assembly 35 can comprise an expandable cage, balloon 36, or other expandable sizing element constructed and arranged to measure the inner surface diameter of tubular tissue, such as a diameter of the duodenum or jejunum. Balloon 36 can comprise a compliant balloon, a non-compliant balloon and/or a pressure-thresholded balloon, and/or balloon 36 can otherwise be constructed and arranged as described in detail hereabove. Expandable assembly 35 can be configured to be expanded via control 34 and/or via user interface 205 of console 200 (e.g. inflated and deflated by delivery and removal, respectively, of fluids by console 200).

Fluids delivered by console 200 to balloon 36 (e.g. fluids supplied by fluid source 200) can be provided at one or more predetermined pressures, or pressure profiles. Diameter measurements can be accomplished by performing a visualization procedure (manual or automated) that assesses balloon 36 diameter. Alternatively or additionally, balloon 36 can be controllably filled with a fluid, and controller 210 can include an algorithm that correlates the fluid volume and/or fluid pressure to the diameter of tubular tissue in contact with the balloon. In some embodiments, subsequent selection (e.g. device model or size selection) and/or expansion diameter (e.g. inflated diameter chosen for sufficient apposition) of expandable assemblies 130, 25 and/or 45 of devices 100, 20 and/or 40, respectively, can be determined using the information provided by sizing device 30 and/or console 200. In some embodiments, device 30 performs a sizing procedure as described herebelow in reference to FIG. 2.

In some embodiments, expandable assembly 35 comprise a balloon or expandable cage including two or more electrodes configured to provide a tissue impedance measurement whose value can be correlated to a level of apposition of expandable assembly 35, and whose expanded diameter (e.g. visually or otherwise measured) correlates to a diameter of tubular tissue in contact with the expandable element. Alternatively or additionally, expandable assembly 130 of device 100, expandable assembly 25 of device 20 and/or expandable assembly 45 of device 40 can be used to measure a diameter of the inner surface of tubular tissue, such as has been described hereabove in reference to expandable assembly 35 and device 30.

In some embodiments, system 10 comprises one or more devices, such as multi-function device 40 shown, that are constructed and arranged to perform two or more functions selected from the group consisting of: treat target tissue such as to deliver energy or otherwise ablate target tissue; expand tissue such as to expand one or more layers of submucosal tissue; and determine or estimate a diameter of a lumen of tubular tissue; and combinations of these. Multi-function device 40 is constructed and arranged to be placed into one or more locations of the GI tract or other internal location of the patient and perform two or more of the functions listed above. In some embodiments, multi-function device 40 is constructed and arranged similar to device 100 described herebelow in reference to FIG. 6. Multi-function device 40 can be configured to perform the multiple functions at multiple axial segments of the GI tract, such as multiple relatively contiguous axial segments of the duodenum as is described herebelow in reference to FIG. 2.

Device 40 comprises handle 42 which attaches to a proximal end of shaft 41 and includes connector 43 for operable attachment to console 200. Positioned on the distal end or on a distal portion of shaft 41 is expandable assembly 45. Expandable assembly 45 can comprise an expandable cage, balloon 46, or other expandable element constructed and arranged to be position in apposition with and/or in close proximity to the inner wall of tubular tissue, such as tissue of the duodenum or jejunum. Balloon 46 can comprise a compliant balloon, a non-compliant balloon and/or a pressure-thresholded balloon, and/or balloon 46 can otherwise be constructed and arranged as described in detail hereabove. Expandable assembly 45 can be configured to be expanded via control 44 and/or via user interface 205 of console 200 (e.g. inflated and deflated by delivery and removal, respectively, of fluids by console 200).

Expandable assembly 45 can comprise treatment element 135', which can comprise a fluid at an ablative temperature delivered into to expandable assembly 45 by console 200 and/or an energy delivery element permanently positioned on, in and/or within expandable assembly 45 (e.g. an energy delivery element configured to deliver thermal energy, electrical energy, light energy, sound energy and/or chemical energy as described herein). In some embodiments, treatment element 135' comprises a mechanical abrader configured to treat tissue through abrasion. In some embodiments, treatment element 135' is constructed and arranged similar to treatment element 135 of device 100 of FIG. 1.

Expandable assembly 45 can comprise one or more elements configured to expand tissue, such as fluid delivery elements 48. Fluid delivery elements 48 can each be positioned within one or more ports 47 as shown. Fluid delivery elements 48 and ports 47 can be constructed and arranged as described hereabove in reference to fluid delivery elements 28 and ports 27, respectively, of device 20 of FIG. 1.

Devices 100, 20, 30 and/or 40 can comprise one or more functional elements, such as functional elements 139, 29, 39, 49, respectively, shown positioned in, on and/or within in expandable assemblies 130, 25, 35 and 45, respectively. Alternatively, functional elements 139, 29, 39 and/or 49 can be located at a different location of the associated device, such as in, on and/or within the associated shaft and/or handle of the device. In some embodiments, one or more functional elements 139, 29, 39 and/or 49 comprise a sensor, such as a sensor selected from the group consisting of:

temperature sensor such as a thermocouple, thermistor, resistance temperature detector and optical temperature sensor; strain gauge; impedance sensor such as a tissue impedance sensor; pressure sensor; blood sensor; optical sensor such as a light sensor; sound sensor such as an ultrasound sensor; electromagnetic sensor such as an electromagnetic field sensor; visual sensor; and combinations of these. Alternatively or additionally, one or more functional elements 139, 29, 39 and/or 49 comprise a transducer, such as a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; a fluid agitating element; and combinations of these. Functional elements 139, 29, 39 and/or 49 can be electrically connected to EDU 250 (e.g. to receive power, send signals and/or receive signals), such as via an electrical connection provided by ports 201. Functional elements 139, 29, 39 and/or 49 can send or receive signals from controller 210 of console 200, such as one or more sensor signals used to control ablation energy provided by console 200. Functional elements 139, 29, 39 and/or 49 can be activated and/or otherwise controlled via controls 104, 24, 34 and/or 44, respectively. Alternatively or additionally, user interface 205 of console 200 can be configured to control functional elements 139, 29, 39 and/or 49.

In some embodiments, console 200 comprises one or more functional elements 209, comprising a sensor or transducer as described hereabove. Functional element 209 can comprise one or more pressure sensors, such as one or more pressure sensors configured to provide a signal used to regulate fluid delivery provided to one or more of devices 100, 20, 30 and/or 40, and/or fluid extraction from one or more of devices 100, 20, 30 and/or 40. Functional element 209 can comprise one or more temperature sensors, such as one or more temperature sensors that provide a signal used to regulate temperature of one or more fluids of console 200.

In some embodiments, system 10 comprises one or more agents configured to be delivered to the patient, such as agent 420. Agent 420 can be delivered by one or more of devices 100, 20, 30, 40 and/or 50, or by a separate device such as a syringe or other medication delivery device. In some embodiments, agent 420 comprises an anti-peristaltic agent, such as L-menthol (i.e. oil of peppermint). Alternatively or additionally, agent 420 can comprise glucagon and/or buscopan. Alternatively, agent 420 can comprise an ablative agent, such as an ablative agent delivered to a tissue surface, such as a mucosal surface. Agent 420 can be delivered into the GI tract, such as via endoscope 50, sheath 80 and/or devices 100, 20, 30 and/or 40. Agent 420 can be delivered systemically, such as via an intravenous or intra-arterial access line, or injected directly into tissue.

As described above, user interface 205 can comprise safety-switch 206 such as a foot-activated switch. Safety-switch 206 can be configured to allow a clinician to activate, modify and/or maintain (e.g. maintain in an "on" state) one or more processes of system 10 without having to use his or her hands (e.g. without having to use a digit of the hand). In some embodiments, system 10 is constructed and arranged to perform a function selected from the group consisting of: automatic contraction (e.g. deflation) of expandable assembly 130 if safety-switch 206 is not activated (e.g. depressed); automatic replacement of ablative fluid (e.g. hot fluid) with neutralizing fluid (e.g. cold fluid) if safety-switch 206 is not activated; initiate introduction of ablative fluid (e.g. hot fluid) into expandable assembly 130 by activation of safety-switch 206 (e.g. after expandable assembly has been pre-expanded with cold fluid and user has confirmed proper position for treatment); allow hands-free activation (e.g. initiation) of a treatment step such that one or more operators can maintain their hands one or more of endoscope 50 and/or devices 100, 20, 30 and/or 40; allow hands-free activation (e.g. initiation) of a treatment step such that the required number of operators is reduced; cause a function to cease if safety-switch 206 is not activated (e.g. depressed); and combinations of these.

Each of devices 100, 20, 30 and/or 40 can be provided in one or more sizes, such as one or more lengths of the associated shaft 110, 21, 31 and/or 41, respectively, and/or one or more diameters (e.g. expanded diameter) of the associated expandable assembly 130, 25, 35 and/or 45, respectively. Luminal sizing as described herein or other anatomical information can be used to select the appropriately sized device to treat the patient.

Figure 2:
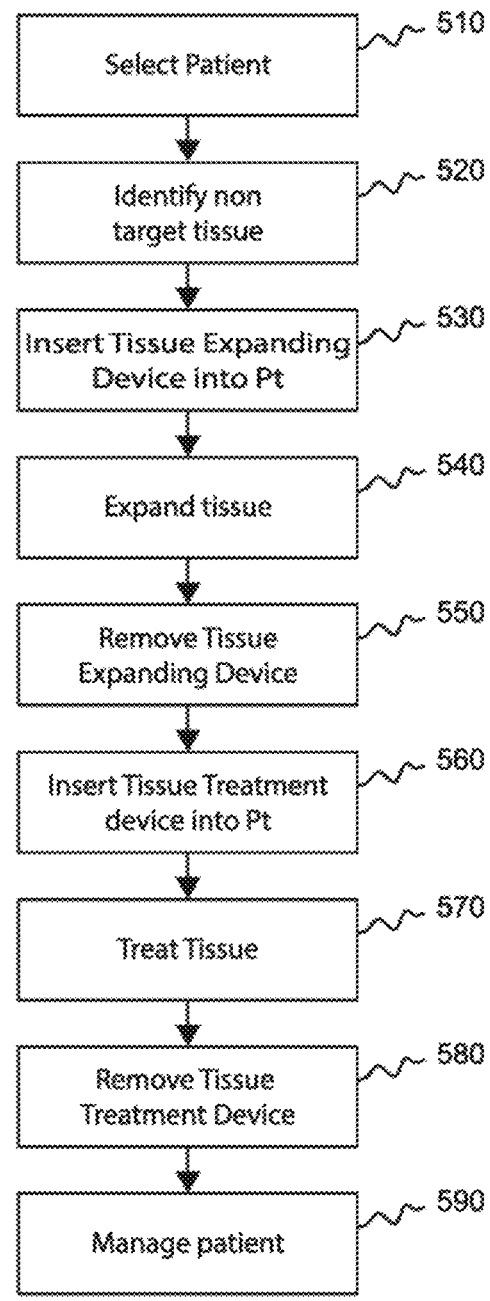
FIG. 2 is a flow chart of a method for treating target tissue of a patient, consistent with the present inventive concepts.

Referring now to FIG. 2, a flow chart of a method of treating target tissue of a patient is illustrated, consistent with the present inventive concepts. In some embodiments, the method of FIG. 2 is accomplished using system 10 of FIG. 1 described hereabove, or system 10 of FIG. 6 described herebelow. In Step 510, a patient is selected for treatment. The patient can be selected to treat a patient disease or disorder selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease (e.g. as a secondary prevention); stroke/TIA; cognitive decline or dementia (e.g. Alzheimer's); diabetic nephropathy; neuropathy; retinopathy; diabetic heart disease and/or heart failure; and combinations of these. In some embodiments, the patient is selected to treat two or more of the above diseases or disorders, such as a patient selected to treat both a form of diabetes and hypercholesterolemia.

The patient selected can be taking one or more medicines to treat their diabetes. The patient selected can have an HbA1c level between 7.5% and 12.0%, between 7.5% and 10%, or between 7.5% and 9.0%. In some embodiments, the patient selected can have an HbA1c level between 6.0% and 12.0%. Patients with higher HbA1c levels and/or other higher disease burden can receive more aggressive treatments (e.g. more tissue treated and/or higher number of repeated treatments over time) as described herebelow in reference to Step 570.

Patient selection can be based on the current level of one or more parameters representing one or more various biomarkers or other representative values of physiologic conditions (e.g. as compared to an average among diabetic and/or non-diabetic patients), such as a level of a parameter selected from the group consisting of: body mass index (BMI) level; waist circumference; HbA1c level; fasting glucose; insulin resistance; liver fibrosis; cholesterol or triglyceride level; duration of years exhibiting type 2 diabetes; fasting C-peptide or C-Peptide stimulation in response to a meal; age; and combinations of these.

Prior to placing any device in the patient, or at any time thereafter (e.g. during or after the procedure), one or more agents can be introduced into the patient, such as an agent introduced into the GI tract directly, such as agent 420 described hereabove in reference to FIG. 1. In some embodiments, agent 420 comprises L-menthol (i.e. oil of peppermint) or other agent configured to provide an anti-peristalsis effect. In these embodiments, a few drops of agent 420 can be placed in an irrigation lumen of an endoscope or other body inserted device with a fluid delivery channel. In some embodiments, approximately 8 mL of L-menthol is mixed with approximately 0.2 mL of Tween 80 (polysorbate 80) in approximately 500 mL of distilled water (i.e. to create an approximately 1.6% solution). Approximately 20 mL of this mixture can be sprayed through a working channel of endoscope 50, or more as required to dampen peristalsis. In some embodiments, the solution can vary between approximately 1.6% and 3.2%. Tween and/or sorbitan monostearate can be used as an emulsifier.

One or more agents can be delivered once the endoscope or other agent delivery device enters the duodenum. In other embodiments, agent 420 is delivered intravenously, and can comprise glucagon and/or buscopan.

In some embodiments, an endoscope is inserted into the patient (e.g. endoscope 50 of FIG. 1). In these embodiments, subsequently inserted devices can be placed through a working channel of the endoscope and/or alongside the endoscope. In some embodiments, an endoscope and an attachable sheath (e.g. scope attachable sheath 80 of FIG. 1) are both inserted into the patient, and subsequently inserted devices can be placed through a working channel of the endoscope, through the attachable sheath and/or alongside the endoscope and the attached sheath. Each patient inserted device can be inserted over a guidewire. In some embodiments, an endoscope stiffening device is used, such as an endoscope stiffening system provided by Zutron Medical of Lenexa, Kansas, USA.

In Step 520, non-target tissue can be identified. Non-target tissue can be identified with a visualization device, such as endoscope 50 of system 10 of FIG. 1. The non-target tissue can comprise the ampulla of Vater, also known as the papilla, the pancreas, or other tissue to which treatment may adversely affect the patient. Step 520 and/or another step of the method of FIG. 2 can include marking the non-target tissue (or tissue proximate the non-target tissue), such as with a tattoo, ink or other visualizable substance, such as a visual agent placed in the mucosa and/or submucosa in or proximate the ampulla of Vater. In some embodiments, one or more markers similar to marker 195 described herebelow in reference to FIG. 3 or 5A-E are deployed in the patient to provide a reference location relative to non-target tissue. Tissue expansion and/or tissue treatment performed in subsequent steps can avoid the non-target tissue identified and potentially marked (e.g. with one or more markers 195) in step 520.

In Step 530, a tissue expansion device is inserted into the patient. Step 530 can include selecting a particular model of tissue expansion device, such as a particular size or other configuration of a tissue expansion device. In some embodiments, the tissue expansion device is constructed and arranged similar to device 20 and/or device 40 of FIG. 1 described hereabove, or device 100 or device 20 described herebelow in reference to FIG. 6. The tissue expansion device can be inserted over a guidewire, such as a Savary-Gilliard® guidewire or other relatively stiff guidewire. The guidewire can be advanced such that its distal end is in the jejunum. During advancement of the tissue expansion device, the guidewire can be held taut in order to prevent the tissue expansion device from forming a loop in the stomach. In some embodiments, the tissue expansion device is inserted through a working channel of an endoscope, such as endoscope 50 of FIG. 1. In other embodiments, the tissue expansion device is inserted alongside an endoscope.

The tissue expansion device is advanced into the duodenum (e.g. over a guidewire). One or more fluid delivery elements of the tissue expansion device can be positioned at least 1 cm, but not more than 5 cm or 10 cm from the ampulla of Vater, to perform a first tissue expansion or otherwise a most-proximal tissue expansion (i.e. closest to the ampulla of Vater). In some embodiments, one or more fluid delivery elements of the tissue expansion device are positioned based on the location of a previously placed marker, such as marker 195 described hereabove in STEP 520. Prior to and/or during insertion, a stiffening wire can be inserted within the tissue expansion device. An endoscope can be positioned adjacent the tissue expansion device, such that both distal ends are beyond the ampulla of Vater (e.g. beyond a tattoo or other marker or marking identifying the ampulla of Vater, as described herein).

In some embodiments, prior to insertion of the tissue expansion device, a lumen diameter sizing device is inserted to the patient, such as device 30 of FIG. 1. Luminal diameter or other information provided by the sizing device can be used to select and/or control the tissue expansion device. The sizing device can be placed over a guidewire as described hereabove or it may be delivered through the working channel of an endoscope. Prior to and/or during insertion, a stiffening wire can be inserted within the sizing device.

The sizing device expandable element (e.g. balloon) is positioned in the post-papillary duodenum and inflated at a particular location within the duodenum with a fluid (such as air or saline) and the pressure of the fluid within the balloon is determined by a pressure sensor attached to the proximal end of the device. The volume of delivered fluid can be detected by the system. The fluid can be delivered slowly, such as until a stable pressure reading of approximately 0.7 psi (or approximately 0.9 psi or 2.0 psi) is determined by the pressure sensor (i.e. a threshold pressure is achieved). The volume of fluid within the balloon at a given pressure is used to ascertain the lumen diameter by reference-checking against a calibration step performed before the sizing procedure (e.g. via one or more algorithms of system 10 of FIG. 1 or 6). Measurements can be taken in at least two locations within the duodenum. An algorithm selects an appropriate ablation balloon size for the individual patient.

In Step 540, tissue is expanded. In some embodiments, saline or other fluid is injected by multiple fluid delivery elements of the tissue expansion device, such as three needles or other fluid delivery elements, positioned in a tissue port and spaced approximately 120° apart along a circumference that deliver injectate (e.g. injectate 221 of FIG. 1) into tissue. Each injection can comprise at least 1 ml, such as at least 2 ml, at least 5 ml or at least 8 ml per fluid delivery element. Volumes injected by the multiple fluid delivery elements can be selected to achieve near full circumferential expansion of submucosal tissue (e.g. without gaps, full 360° expansion).

Subsequent injections of fluid into tissue can be delivered, such as at an axial separation distance of between 1 cm and 2 cm apart from a previous injection (e.g. 1 cm to 2 cm distally in the duodenum). In some embodiments, multiple injections are positioned at least 0.5 cm apart along the axis of the duodenum, such as between 1.0 cm and 5.0 cm apart, such as approximately 1.0 cm, 2.0 cm, 3.0 cm, 4.0 cm and/or 5.0 cm apart from one another along the axis of the duodenum. In some embodiments, axial separation of injection sites (i.e. translation distance of the tissue expansion device between injections) can approximate half the length of a balloon onto which the fluid delivery elements are mounted, such as half the length of balloon 26 of FIG. 1. In some embodiments, a series of 5-15 sets (e.g. 8-12 sets) of injections (e.g. each set comprising injections from 2, 3 or more fluid delivery elements) can be performed by delivering injectate (e.g. a fluid containing a visualizable dye) to the tissue to be expanding and subsequently translating the tissue expansion device to a new axial location (e.g. after proper expansion of tissue is confirmed visually or otherwise). Each advancement and/or retraction of the tissue expansion device can be made in unison with advancement and/or retraction of an endoscope positioned alongside the tissue expansion device.

Tissue expansion can begin at a location proximate but distal to the ampulla of Vater, such as at a location at least 1 cm distal to but not more than 5 cm or 10 cm from the ampulla of Vater. A series of relatively contiguous, full circumferential submucosal tissue expansions can be performed (e.g. moving distally), for example up to the Ligament of Treitz. In alternate embodiments, multiple full circumferential tissue expansions are performed by moving the tissue expansion device from distal to proximal locations, or in a discontinuous manner.

Volumes of injections and/or axial separation of injection can be chosen to avoid axial gaps. After injections, gaps identified circumferentially and/or axially (e.g. via endoscope camera, fluoroscope or ultrasound imaging device), can be filled in as deemed necessary via additional injection (e.g. with or without rotation and/or translation of the tissue expansion device)

In some embodiments, the amount of fluid (e.g. liquid such as water or gas such as air) in an expandable assembly supporting the fluid delivery elements is reduced as the injectate is delivered into tissue, such as to prevent excessive force being applied to tissue proximate the expanding tissue (i.e. due to the decreasing lumen proximate the expanding tissue in contact with expandable assembly), such as is described in detail hereabove in reference to FIG. 1.

In some embodiments, a first volume of fluid (e.g. air) is determined that causes a balloon of the tissue expansion device to get sufficient apposition with a lumen of the GI tract (e.g. a lumen of the duodenum), such as by measuring pressure achieved within the balloon. The balloon is subsequently compacted (i.e. fluid removed), and filled with a second volume that is less than the first volume, and a confirmation of a lower pressure can be performed. Vacuum is applied within the GI lumen (e.g. via an insufflation port of an endoscope or other inserted device), causing the lumen to collapse onto the balloon without compressing the luminal wall. A second vacuum is applied to one or more tissue ports on the balloon (e.g. tissue ports 27 of FIG. 1), causing tissue to be drawn into the tissue ports. One or more needles (e.g. fluid delivery elements 28 of FIG. 1) can be advanced into the tissue contained in the tissue ports, while avoiding the potential of the needles penetrating an outer layer and/or outside of the GI wall tissue, as has been described in detail hereabove. In some embodiments, tissue is penetrated by the fluid delivery elements at the time of the application of the vacuum, without the advancement of the fluid delivery element, also as described hereabove.

Multiple injections (e.g. three injections from three equally separated fluid delivery elements) can be performed simultaneously or sequentially. A vacuum can be applied prior to delivery of fluid, such as to draw tissue toward the fluid delivery element (e.g. into three associated ports as described in reference to FIG. 1). After fluid delivery, the vacuum can be removed and the tissue expansion device advanced (or retracted).

The injectate delivered can include an agent that is directly visualizable by an operator (e.g. via an endoscope camera or other camera), radiographically visualizable (e.g. via a fluoroscope or other X-ray imaging device) and/or ultrasonically reflectable or otherwise visualizable (e.g. via an ultrasound imaging device), such as an injectate 221 comprising visualizable material, as described hereabove in reference to FIG. 1. Visualization of the expanded tissue can be used to determine proper volume of injectate delivered as well as sufficient tissue expansion (e.g. sufficient thickness, axial length and/or circumferentiality of tissue expansion). The pressure of the expandable assembly (e.g. balloon) or the volume of fluid within the expandable assembly can also be monitored to determine if a proper volume of injectate has been delivered to achieve adequate tissue expansion.

In Step 550, the tissue expansion device is removed, for example using an over-the wire exchange leaving the guidewire in place. An endoscope and/or sheath can also be removed during this step. In some embodiments, the tissue expansion device is also configured to ablate or otherwise treat tissue (e.g. in addition to tissue expansion), and the tissue expansion device remains in place to perform Step 570.

In Step 560, a tissue treatment device is inserted into the patient (e.g. if not already in place to perform the tissue expansion step described above, such as when the tissue treatment device is of similar construction and arrangement to multi-function device 40 described hereabove in reference to FIG. 1). Step 560 can include selecting a particular model of a tissue treatment device, such as a particular size or other configuration of a tissue treatment device. In some embodiments, the tissue treatment device is constructed and arranged similar to device 100 and/or device 40 of FIG. 1 described hereabove, and/or device 100 of FIG. 6 described herebelow. In some embodiments, prior to selection of the tissue treatment device, a lumen diameter sizing device, such as device 30 of FIG. 1, is inserted and used to determine the size of a tissue treatment device to be used (e.g. to select a particular diameter of an expandable treatment assembly of the treatment device).

The tissue treatment device can be placed through an endoscope, such as endoscope 50 of FIG. 1, or through a scope attached sheath, such as sheath 80 of FIG. 1. Alternatively or additionally, the tissue treatment device can be placed over a guidewire, such as guidewire 60 of FIG. 1. In some embodiments, the tissue treatment device is placed over the same guidewire used to introduce the tissue expansion device of Steps 530-550. The tissue treatment device can be advanced to the duodenum. In some embodiments, the tissue treatment device can be advanced to the duodenum over a guidewire without an endoscope in place, subsequent to which an endoscope can be advanced to a similar location in the duodenum. In some embodiments, prior to and/or during insertion, a stiffening wire can be inserted within the tissue treatment device.

In Step 570, target tissue is treated (e.g. ablated) by one or more treatment elements of the tissue treatment device, such as treatment element 135 positioned on expandable assembly 130 of device 100 of FIG. 1. The target tissue can comprise one or more portions of the mucosal layer of the duodenum. Treated tissue can further comprise at least an inner layer of neighboring submucosal tissue. One or more circumferential ablations or other treatments can be performed along a length of the GI tract (e.g. along one or more axial segments of the GI tract), such as along a length of the duodenum at least 1 cm distal to the ampulla of Vater, such as at a location at least 1 cm distal to but within 3 cm, 5 cm or 10 cm of the ampulla of Vater. In some embodiments, all ablations are performed at least 2 cm or at least 3 cm distal to the ampulla of Vater (e.g. tissue within 1 cm, 2 cm or 3 cm of the ampulla of Vater is not ablated). In some embodiments, one or more circumferential ablations (e.g. a most-proximal duodenal axial segment ablated) is performed based on the position of a previously placed marker, such as marker 195 described hereabove in STEP 520. In some embodiments, tissue treatments are only performed at locations that have had submucosal tissue expansion performed and/or confirmed (e.g. visually). In other embodiments, tissue treatments are performed without any tissue expansion, avoiding the need for Steps 530-550.

In some embodiments, a thermal treatment is provided by sufficiently hot or cold fluid introduced into a balloon of the tissue treatment device to ablate tissue. In other embodiments, different forms of energy delivery or other tissue treatments are performed, as described in detail in reference to system 10 of FIG. 1 or system 10 of FIG. 6.

The tissue treatment device can treat a series of axial segments of GI tract tissue comprising lengths between 1 cm and 5 cm each, such as approximately 3 cm in length each. The tissue treatment device can treat a cumulative axial length of GI tract tissue (e.g. an axial length of duodenal mucosa tissue) of less than or equal to 3 cm, 6 cm, 9 cm, 15 cm, or 20 cm. The tissue treatment device can be constructed and arranged to treat more than 3 cm of axial length of duodenal mucosa, such as more than 3.4 cm, more than 6 cm, more than 7 cm, more than 8 cm or more than 9 cm (e.g. approximately 9.3 cm), such as to achieve a clinical benefit for a diabetes or other patient as described herebelow in reference to applicant's clinical study (including the results presented in FIGS. 7-28). In some embodiments, at least 10%, 15%, 25%, 30% and/or 50% of the duodenal mucosa distal to the ampulla of Vater is treated. The axial length and/or overall volume of tissue treated can correspond to a patient parameter, such as the longevity of the disease or other disease parameter as described in detail herebelow (e.g. higher disease burden correlating to larger volumes of tissue treated).

In some embodiments, at least 3 axial segments of duodenal mucosal tissue are treated (e.g. sequentially treated), such as with a treatment element configured to deliver energy to a delivery zone with a length between 1.0 cm and 4.0 cm (e.g. tissue contacting length of a balloon filled with ablative fluid), such as a delivery zone length between 1.9 cm and 3.3 cm, or approximately 3 cm in length. In some embodiments, at least 4 axial segments of duodenal mucosal tissue are treated, such as at least 6 axial segments of duodenal mucosal tissue are treated. In these embodiments, the treatment element can be configured to deliver energy to a delivery zone with a length between 0.7 cm and 2.0 cm (e.g. tissue contacting length of a balloon filled with ablative fluid). In some embodiments, the treatment element comprises ablative fluid delivered into a balloon, such as the balloon 136 described herein. Multiple tissue treatments are performed by repositioning the treatment element (e.g. treatment element 135 of FIG. 1), which can further include expanding an expandable assembly (e.g. expandable assembly 130 of FIG. 1) onto and/or into which the treatment element treating the tissue can be positioned. Contact between the target tissue and the treatment element can be accomplished using desufflation techniques to bring the tissue toward the treatment element, as described in detail hereabove. Tissue treatment is performed, such as by filling the expandable assembly with ablative temperature fluid and/or delivering any form of energy to the target tissue such as is described herein. In embodiments where the tissue treatment device is delivered over a guidewire, the guidewire can be retracted (e.g. at least retracted to a location proximal to the treatment element) prior to any tissue treatments.

Multiple treatments can be performed by advancing or retracting the tissue treatment element and/or tissue treatment device. In some embodiments, the tissue treatment element is positioned at a distal location and a series of tissue treatments are performed, such as at least 3 tissue treatments performed in which the tissue treatment device is retracted approximately the length of the tissue contacting portion of the treatment element such as to treat relatively contiguous, non-overlapping, full circumferential axial segments of the duodenum. After each tissue treatment, confirmation of being away from (e.g. distal to) any non-target tissue marked and/or otherwise identified (e.g. in Step 520) can be performed (e.g. be visualizing a previously placed marker 195). In some embodiments, a marker 195 is placed to avoid any damage to the ampulla of Vater. In some embodiments, after three axial segments of duodenal mucosa are treated (e.g. treated distally to proximally), an assessment of the linear distance between the most proximal treatment segment and the ampulla of Vater is performed (e.g. one or more components of system 10 is used to determine the distance). If sufficient length is determined (e.g. the determined distance is above a threshold), additional (more proximal) axial tissue segments can be treated. During translation of the tissue treatment device over a guidewire, undesired movement of the guidewire is prevented or otherwise reduced by the operator.

In some embodiments, the system of the present inventive concepts (e.g. system 10 of FIG. 1 or 6) is configured to allow only one ablation per (pre-determined) time period, such as to prevent two ablations within the time period such as to prevent repetitive ablation in the same or at least similar (e.g. overlapping) portions of the GI tract (e.g. rapid treatment of similar treatment zones).

In some embodiments, the tissue treatment of Step 570 should be completed within approximately 120 minutes or within approximately 60 minutes of the initiation of tissue expansion performed in Step 540, such as within approximately 45 minutes, 30 minutes and/or 20 minutes. Performance of tissue treatment within this time window prevents an unacceptable amount of injectate dissipation from the expanded tissue (e.g. submucosal tissue) space. In some embodiments, the system of the present inventive concepts (e.g. system 10 of FIG. 1 or 6) is configured to prevent a tissue treatment (e.g. ablation) until a submucosal expansion step has been performed.

The amount of target tissue treated and/or the number of treatments performed can correlate to (e.g. be proportional to) one or more patient conditions (e.g. more severe correlates to more tissue treated and/or more treatments performed over time). This increased treatment can comprise an increased axial length of tissue treated (e.g. an increased cumulative axial length of duodenum ablated or otherwise treated), a deeper depth of treatment and/or a larger number of treatments performed over time in order to achieve a sustained treatment response. Increased treatments can correlate to a higher burden of the patient's disease (e.g. relatively long duration since diagnosis, higher HbA1c level than a standard diabetic patient and/or more mucosal hypertrophy than a standard diabetic patient). In some embodiments, the volume of target tissue treated and/or the number of treatments performed is proportional to the patient's HbA1c level.

In some embodiments, the tissue treatment is modified to avoid creation of a duodenal stenosis or stricture, such as to limit one or more of: amount of energy delivered; peak energy delivered; duration of energy delivered; length of tissue treated; depth of tissue treated; and combinations of these. In some embodiments, a duodenal stenosis or stricture is treated with balloon dilatation.

In some embodiments, tissue expansion is not performed prior to tissue treatment. In some embodiments, lumen diameter sizing is not performed, or is performed with a tissue expansion device and/or a tissue treatment device. In some embodiments, a single device is inserted into the patient to perform two or more of: lumen diameter sizing; tissue expansion; and tissue treatment; such as a device similar to device 40 of FIG. 1.

In Step 580, the tissue treatment device is removed. In addition, any guidewires, endoscopes, scope attached sheaths, or other inserted devices are removed.

In Step 590, a step of managing the patient post-procedurally can be performed. Post-procedure patient management can comprise one or more of: a liquid diet for at least 1 day, 4 days, 5 days, 7 days or 14 days; a soft diet for at least 1 day, 4 days, 5 days, 7 days, or 14 days; a low sugar and/or low fat diet for at least 1 week, 1 month or 1 year; a standardized diabetic (e.g. ADA) diet for at least 1 week, 1 month or 1 year; and nutritional counseling for at least 1 week, 1 month or 1 year.

The therapy provided by the systems, methods and devices of the present invention can lead to numerous therapeutic benefit outcomes to the patient receiving the treatment. In some embodiments, the patient has an outcome selected from the group consisting of: improvement in HbA1c, fasting glucose and/or post-prandial glucose; at least a 1% improvement in HbA1c; d a resultant HbA1c of less than 7.5%, less than 7%, less than 6.5%, or less than 6% (e.g. at a time period after a tissue treatment procedure of at least 1 month, 3 months, 6 months or 12 months); improvement in one or more triglyceride levels; improvement in AST, ALT, liver fibrosis panel, liver fibrosis score, NAFLD assessment and/or or NASH assessment; improvement in risk of myocardial infarction, stroke, TIA and/or peripheral vascular disease or diabetic cardiomyopathy; improvement in microvascular disease risk such as nephropathy, retinopathy and/or neuropathy; reduced development of end-stage renal disease, blindness and/or amputation; reduced insulin requirement (e.g. in patients with insulin-dependent diabetes) or other injectable therapy requirement; reduced medication requirement (e.g. in patients with diabetes) either in number of medicines or dosage of medicines; improved fetal birth outcomes (e.g. in patients with gestational diabetes); improved fertility in patients with polycystic ovarian syndrome and/or reduced hirsutism; weight loss of at least 5% of excess body weight, or at least 10%, 20%, 30% or 40% of excess body weight; reduced blood pressure; reduced cardiovascular risk; improved diabetes control and/or reduced diabetic complications; reduced obesity and/or reduced weight; reduced cognitive decline or prevention of dementia; and combinations of these.

The therapy provided by the systems, methods and devices of the present invention can have a clinically significant durability that lasts for at least 3 months, at least 6 months, at least 1 year or at least 2 years. The durability of the treatment can be enhanced by treating more volumes of tissue, such as by treating deeper and/or longer lengths of duodenal mucosa, or by treating the patient multiple times in the same or different regions of the duodenum, small intestine and/or stomach. The durability can be improved by selecting patients with a prior history of dietary compliance and medication compliance and/or a duration of the disease within a particular time window such as less than 2 year or 5 years, or less than 7 years or 10 years.

The systems, methods and devices of the present invention can be constructed and arranged to avoid or reduce the likelihood of one or more adverse events. In some embodiments, pancreatitis is avoided by excluding the ampulla of Vater while performing tissue expansion (e.g. submucosal tissue expansion) and/or tissue treatment (e.g. hot fluid and/or other tissue ablation). In some embodiments, duodenal stenosis and/or stricture can be avoided by performing one or more of the following: ablating only mucosal tissue proximate expanded submucosal tissue layers; ablating only mucosal tissue proximate submucosal tissue layers expanded within 15 minutes, 30 minutes or 45 minutes of ablation; avoiding a second ablation to a tissue segment ablated within 24 hours; and treating tissue (e.g. ablating) only when the operator has direct visualization (e.g. endoscopic visualization) and/or other visualization (e.g. via X-ray or ultrasonic visualization devices) of the tissue treatment element and the tissue being treated.

Applicant has conducted human studies with the systems, methods and devices of the present inventive concepts.

Included below are results of early studies and associated data collected through Jul. 18, 2014.

Some patients received treatment of approximately 9 cm of relatively full-circumferential axial length of duodenal mucosa (via three approximately 3 cm hot fluid balloon-based ablations), and some patients received treatment of less than or equal to 6 cm of relatively full-circumferential axial length of duodenal mucosa (via two or less approximately 3 cm hot fluid balloon-based ablations).

Early results showed: baseline HbA1c was 9.2% and FPG was 187 mg/dl. 1 month post-procedure, HbA1c was reduced by 1.1% in LS-DMR patients (patients receiving duodenal mucosa treatments of approximately 9 cm (e.g. 9.3 cm) of duodenal tissue) but only 0.1% in SS-DMR patients (patients receiving duodenal mucosa treatment of approximately 3 cm (e.g. 3.4 cm) of duodenal tissue, the data representing 12 LS-DMR patients vs 7 SS-DMR patients, each group at 1 month (p=0.058). By 3 months, HbA1c was reduced by approximately 2% in LS-DMR patients but was unchanged in SS-DMR patients (N=5 in each group at 3 months). FPG reductions in LS-DMR patients were −64 mg/dl and −67 mg/dl at 1 and 3 months.

FIG. 7 shows a breakdown of a number of patients who received various quantities of duodenal axial segment treatments comprising delivery of heat from an ablative fluid delivered to a balloon-based treatment assembly. Thirty five patients were treated in a dosimetric evaluation of the systems, methods and devices described herein. In the study, an ablation is defined as an axial length of circumferentially ablated tissue, ablated with a single positioning of the balloon and subsequent hot fluid delivery to the balloon. Ablation dose is defined as the total length of circumferentially ablated tissue on a single procedural day. A single patient received 5 ablations (the highest dose administered), and duodenal stenosis presented as food intolerance and epigastric discomfort. After endoscopic balloon dilation, the patient recovered without further issue. This patient with the duodenal stenosis lost a substantial amount of weight in the 2 weeks after the development of stenosis (nearly 10 kilograms). Controlled duodenal stenosis may be an effective means of achieving substantial weight loss with its attendant benefits on metabolic or obesity-related ailments. Creation of a therapeutic restriction can be performed as described in co-pending International Patent Application Serial Number PCT/US2014/066829, titled "Systems, Devices and Methods for the Creation of a Therapeutic Restriction in the Gastrointestinal Tract", filed Nov. 21, 2014, the content of which is incorporated herein by reference in its entirety.

In some embodiments, the systems, devices and methods of the present inventive concepts can be configured to deliver at least two ablations to target tissue (e.g. at least two sequential deliveries of energy or other treatments to different axial segments of GI mucosa), such as to deliver at least three ablations to target tissue. In some embodiments, a minimum and/or maximum amount of duodenal mucosa is treated, such as has been described hereabove.

FIG. 8 is a table of cumulative demographic information for the first 21 patients of the applicant's studies. These baseline characteristics are generalizable and relevant to the Type 2 diabetes population.

In some embodiments, the systems, devices and methods of the present inventive concepts can be configured to treat patients with a characteristic selected from the group consisting of: duration of diabetes less than 10 years; age between 18 yrs and 75 yrs; BMI between 20 and 60, such as a BMI between 24 and 40; and combinations thereof.

FIG. 9 is a table of results of applicant's studies, detailing recorded dose dependent improvements in glycemic control. Applicant measured three validated measures of glycemic control, Hemoglobin A1c (HbA1c), fasting plasma glucose (FPG), and two hour post-prandial glucose (2hPG).

In some embodiments, the systems, devices and methods of the present inventive concepts can be configured to provide a therapeutic benefit selected from the group consisting of: a reduction in HbA1c of at least 0.7%, 1.0% or 1.5% at three months, such as a reduction of approximately 2.18 at three months; an FPG of no more than 150 mg/dl, 126 mg/dl or 100 mg/dl, such as an FPG that can result with a reduction of approximately 63.5 mg/dl; a 2hPG of no more than 250, 200 or 175, such as an 2hPG that can result with a reduction of approximately 103.7; and combinations thereof.

In some embodiments, an absolute change of at least 0.7%, 1.0%, 1.5% and/or 2.0% in HbA1c is expected. In some embodiments, a relative change above an HbA1c target is expected, such as a relative change of at least 50%, 75% or 100%, such as when the target HbA1c is an HbA1c of approximately 6.5%, 7.0% or 7.5%. It has been reported that a 1% absolute change in HbA1c correlates to a 40% reduction in risk of microvascular complication due to diabetes.

Figure 10:
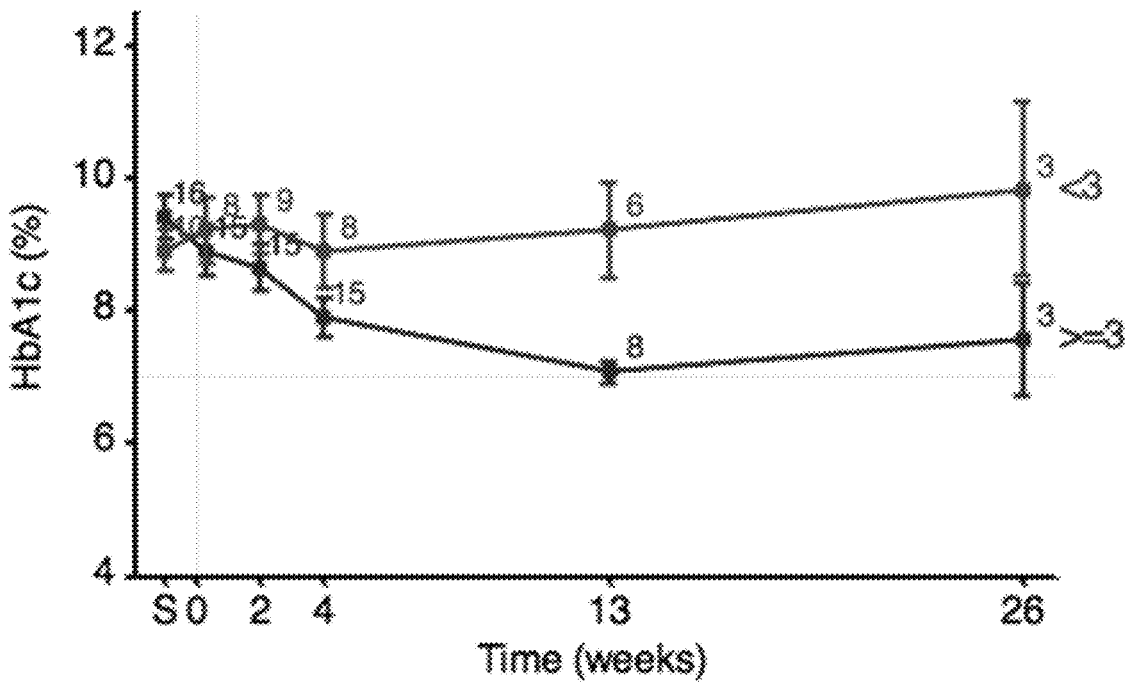
FIG. 10 is a graph illustrating HbA1c reductions in patients receiving three or more ablations.

FIG. 10 is a graph illustrating an approximately 2% HbA1c reduction in patients receiving three or more ablations compared with no change in those receiving fewer than 3 ablations.

In some embodiments, the systems, devices and methods of the present inventive concepts can be configured to achieve an HbA1c level at or below 7.5%, or 7.0% or 6.5%, such as at a time period of 3 months or more, such as by ablating a cumulative length of duodenal mucosa greater than 6 cm, greater than 7 cm, greater than 8 cm or greater than 9 cm (e.g. via 2, 3 or more ablations as described herein).

Figure 11:
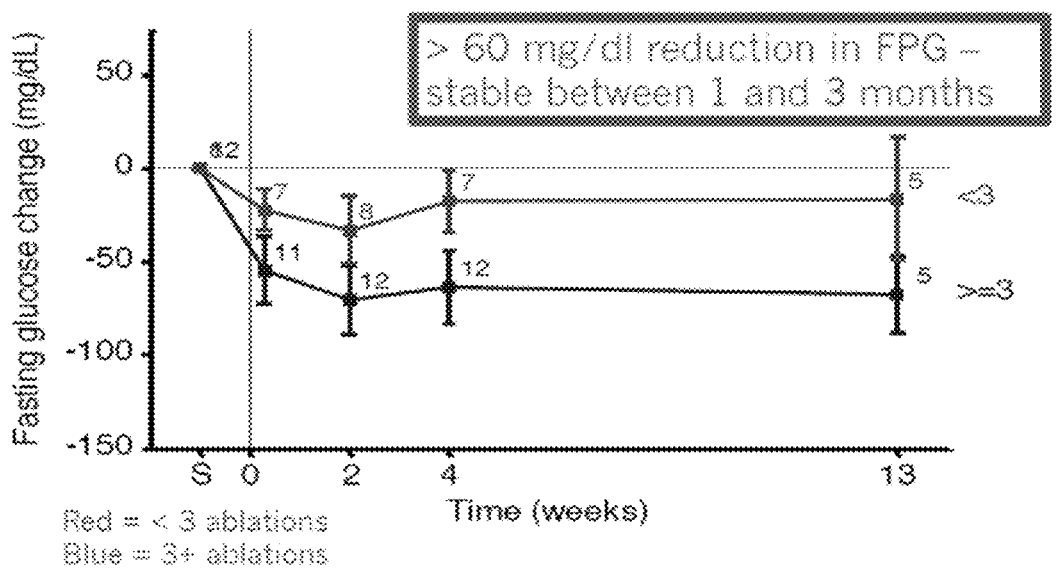
FIG. 11 is a graph illustrating reduction in FPG levels.

FIG. 11 is a graph illustrating a similar reduction in FPG levels, which remain stable between one and three month post procedure.

Figure 12:
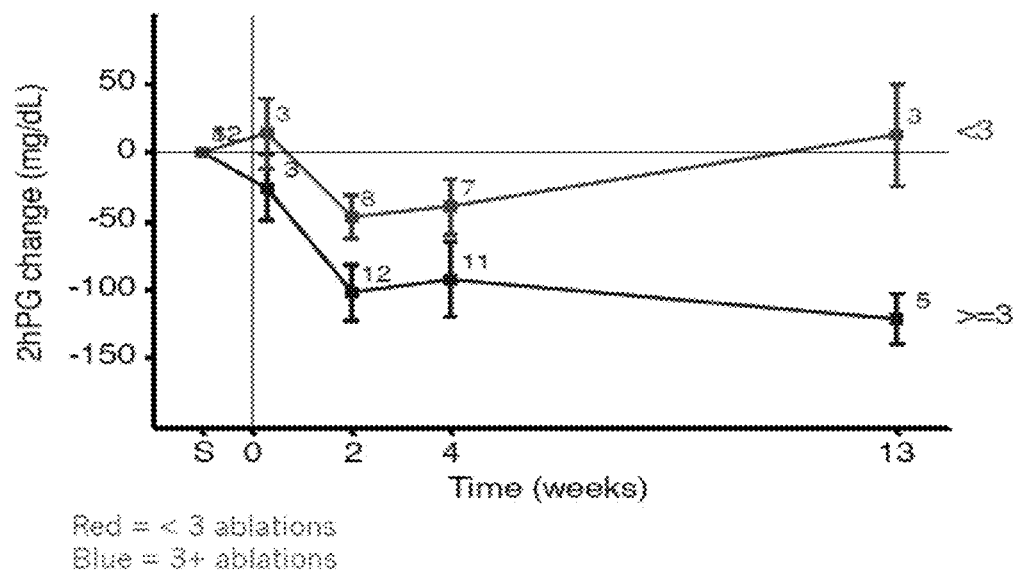
FIG. 12 is a graph illustrating improvement in 2hPG measurements.

FIG. 12 is a graphs illustrating similar improvement in 2hPG measurements.

Figure 13:
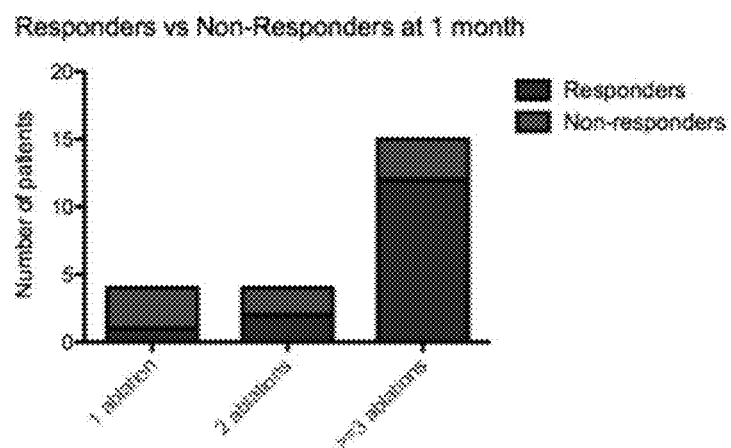
FIG. 13 is a graph showing treatment response rates.

FIG. 13 is a graph of treatment response rates, showing that more ablations correlate to a higher percentage of positive patient outcomes. Responders, or patients with positive clinical results, are defined as having an HbA1c reduction of at least 0.7% at 1 month.

Figure 14:
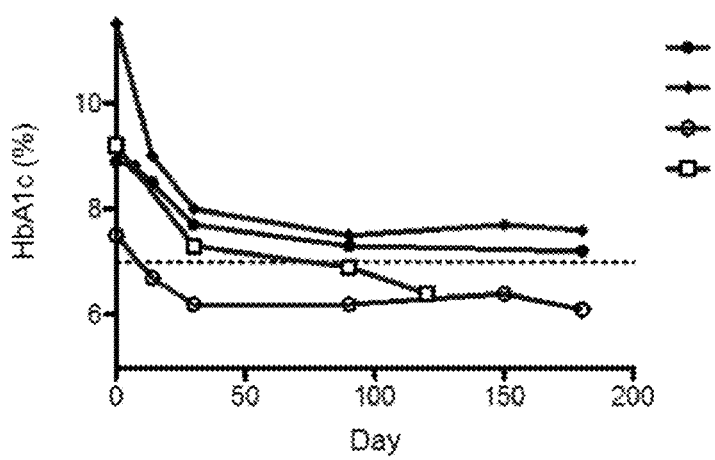
FIG. 14 is a graph of HbA1c percentages measured for at least 120 days post treatment.

FIG. 14 is a graph of HbA1c percentages, measured for at least 120 days post treatment, showing a durable treatment effect in four out of five patients.

In some embodiments, the systems, devices and methods of the present inventive concepts can be configured to maintain HbA1c below 7.5% at 150 days. Note that 3 out of 4 patients are also on lower levels of medications than were being administered prior to the tissue treatment procedure.

Figure 15:
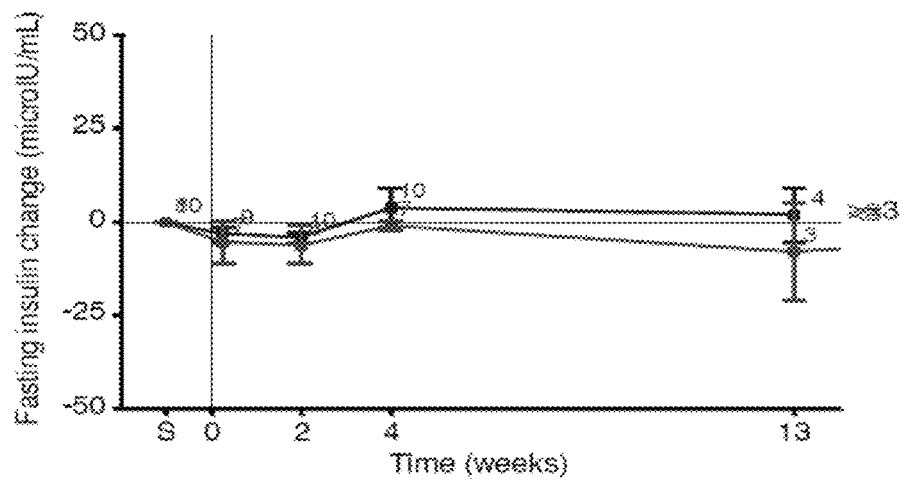
FIG. 15 is a graph of fasting insulin change data over a 3 month period.

FIG. 15 is a graph of fasting insulin change data, over 3 months, showing an improvement in the health of the beta cell.

Figure 16:
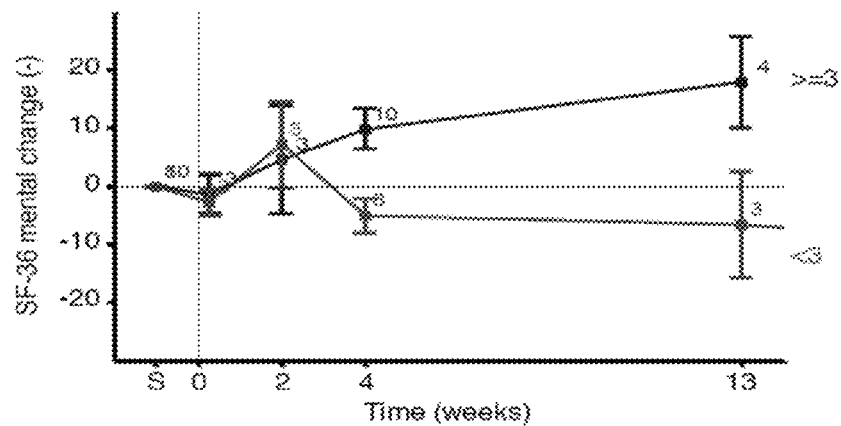
FIG. 16 is a graph of SF-36 mental value changes.

FIG. 16 is a graph of SF-36 Mental value changes, showing improved patient satisfaction through better glycemic control.

In some embodiments, the systems, devices and methods of the present inventive concepts can be configured to cause an improvement in a patient condition as measured by the clinical standard SF-36 Health Survey, such as an improvement in the SF-36 Mental Change score of at least 3 points, at least 5 points or at least 10 points.

Figure 17:
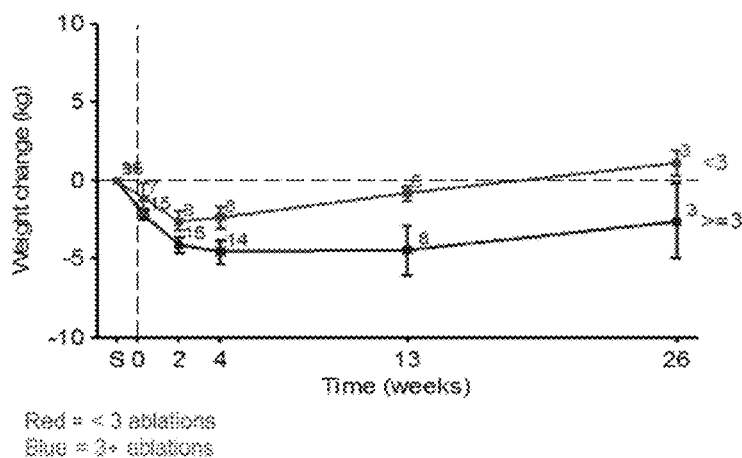
FIG. 17 is a graph of weight change in study patients.

FIG. 17 is a graph of weight change in study patients, showing that weight loss was also noticed in a dose dependent manner.

In some embodiments, the systems, devices and methods of the present inventive concepts can be configured to achieve at least 3 kg or at least 4 kg of weight loss.

Figure 18:
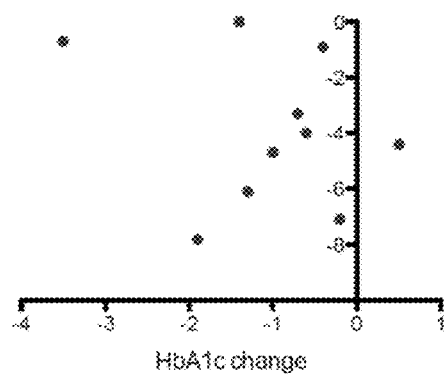
FIG. 18 is a graph regarding weight loss and HbA1c.

FIG. 18 is a graph suggesting that weight loss and HbA1c are not well correlated based on 30 day post treatment data.

Figure 19:
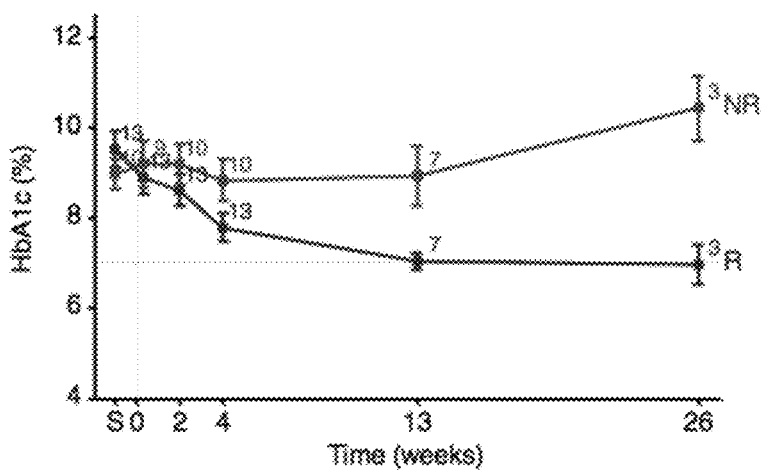
FIG. 19 is a graph of HbA1c percentages over a six week period comparing responders and non-responders.

FIG. 19 is a graph of HbA1c percentage over a twenty six week period, comparing responders R and non-responders NR.

Figure 20:
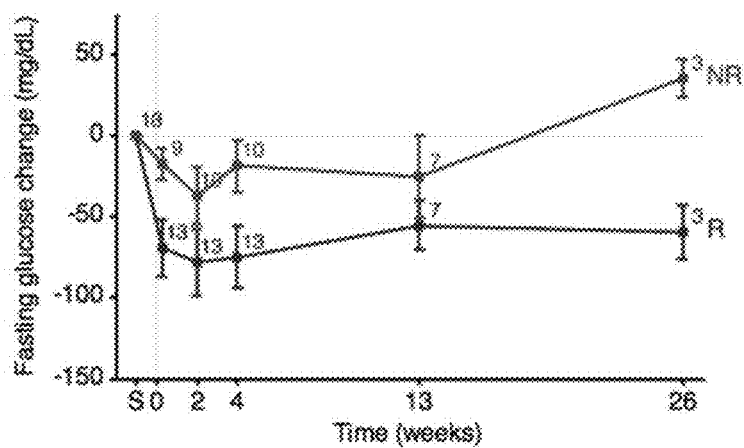
FIG. 20 is a graph of fasting glucose change over a twenty-six week period comparing responders and non-responders.

FIG. 20 is a graph of Fasting glucose change (mg/dL) over a twenty six week period, comparing responders R and non-responders NR.

Figure 21:
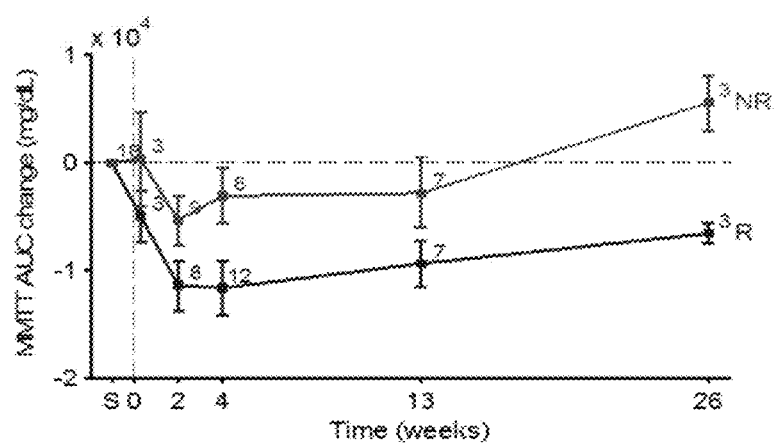
FIG. 21 is a graph of change under the curve of a mixed meal tolerance test.

FIG. 21 is a graph of the change in the area under the curve of a mixed meal tolerance test.

Figure 22:
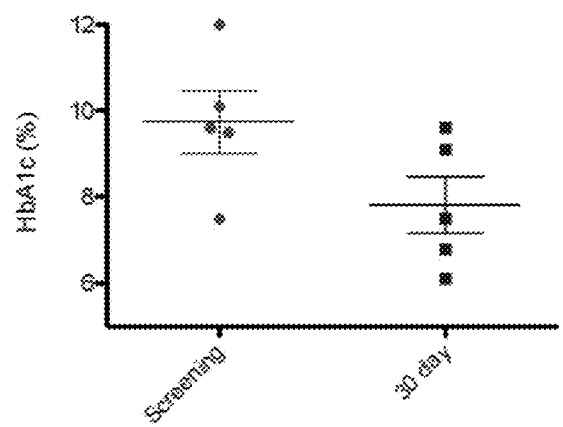
FIG. 22 is a graph of three patients exhibiting a large treatment effect.

FIG. 22 is a graph of three patients exhibiting a large treatment effect, a 1.9% HbA1c improvement at 30 days.

Figures 23, 24:
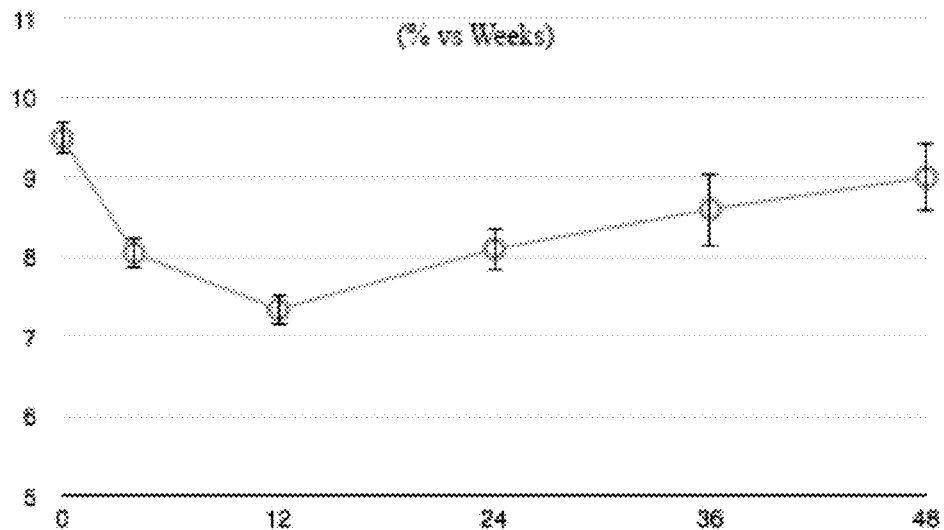
FIG. 23 is a table presenting the large effect size of high dose cohort.
FIG. 24 is a graph showing the average HbA1c in all available subjects treated by the systems, devices and methods of the present inventive concepts.

FIG. 23 is a table presenting the large effect size of high dose cohort being statistically significantly better than low dose cohort.

Human studies using the systems, devices and methods of the present inventive concepts have demonstrated significant effectiveness, such as at least a 2% HbA1c reduction in numerous patients at 3 months, a strong indication of clinical value for patients with poorly controlled glucose levels. The studies demonstrated excellent concordance between HbA1c and other surrogate markers such as fasting glucose and post-prandial glucose. The studies also demonstrated clinically meaningful weight loss. In some embodiments, the systems, devices and methods of the present inventive concepts can be used to treat naïve patients with an HbA1c of more than 6%, 6.5%, or 7%. The treatment could further include the administration of metformin. The treatment of the present inventive concepts (with or without the administration of metformin or other single drug) could provide a therapeutic benefit to the patient better than a treatment comprising drug therapy alone (e.g. metformin and/or another single drug therapy). In some embodiments, metformin and a second-line drug can be included in the treatment of the present inventive concepts. Treatment outcomes would include improvement in HbA1c, such as patients who achieve an improvement (i.e. reduction) of at least 1% in HbA1c and/or patients who achieve a target HbA1c of less than or equal to 6.0%, 6.5%, 7.0%, or 7.5%. Treatment can also include reduction in hypoglycemic events, improved quality of life, weight loss, and combinations of the above.

Included below are results of continued studies and associated data collected through Jul. 8, 2015.

Applicant's continued studies included the recording of various patient parameters affected by the treatment of the present inventive concepts, these parameters including but not limited to: HbA1c, fasting blood glucose and post prandial glucose. Patients received between one and five ablations (e.g. two to five sequential ablations performed along two to five axial segments of the duodenum distal to the ampulla of Vater) on a single procedural day. The ablations were delivered by an expandable balloon filled with hot fluid at an ablative temperature, as described in detail herein. The below data were collected from 39 patients with the following patient demographics:

| Characteristic | Value (N = 39) |
| --- | --- |
| Duration diabetes - yr | 5.9+/−2.2 |
| Age - yr | 53.7+/−7.3 |
| Female sex - N (%) | 14 (35.9) |
| Weight - kg | 85.1+/−12.0 |
| Height - cm | 165.5+/−8.8 |
| BMI - kg/m$^2$ | 31.0+/−3.4 |

Procedures were completed using general anesthesia. All patients were discharged on either the day of procedure (19/39) or after an overnight stay (20/39). The number of patients available (included) for each followup study described in FIGS. 24-28, has the following distribution:

| Elapsed Time since Procedure | 2 Day | 14 Day | 1 Month | 3 Months | 6 Months | 9 Months | 12 Months |
| --- | --- | --- | --- | --- | --- | --- | --- |
| # of Pts at Followup | 39 | 39 | 39 | 38 | 34 | 21 | 21 |

The average baseline HbA1c was 9.5% (SD 1.3%) in 39 patients treated between August 2013 and December 2014. HbA1c was 8.1% (SD 1.3%) 1 month post-procedure, 7.3% (SD 1.2%) 3 months post-procedure, and 8.1% (SD 1.6%) 6 months post-procedure. These HbA1c improvements in the entire cohort are seen despite substantial masking of treatment effect due to medication reductions in highly responsive patients in the months immediately after the procedure. The average HbA1c improvement in 21 patients at a 1 year followup is 0.5% (despite the fact that 9 out of these 21 patients were on reduced glycemic medicines compared to before their procedure).

FIG. 24 represents the average HbA1c (%) in all available (at the time of followup) subjects treated by the systems, devices and methods of the present inventive concepts.

The magnitude of the treatment effect was analyzed as a function of treated dose (i.e. a dosimetric analysis was performed). Patients who had approximately 9 cm (e.g. 9.3 cm) of duodenal tissue treated (e.g. in at least three applications of thermal energy to duodenal tissue) were labeled to have received a "Long Segment DMR" ("LS-DMR"). Patients who had approximately 3 cm (e.g. 3.4 cm) of duodenal tissue treated (e.g. in two or less applications of thermal energy to duodenal tissue) were labeled as "Short Segment DMR" ("SS-DMR"). At 1 month follow up, HbA1c was reduced by an average of 1.7% (SD 1.0%) in LS-DMR and by 0.7% (SD 1.2%) in the SS-DMR (n=28 vs 11 at 1 months). At 3 months follow up, HbA1c was reduced by an average of 2.5% (SD 1.3%) in LS-DMR and by 1.2% (SD 1.8%) in SS-DMR (n=28 vs 10 at 3 months, p<0.05 for LS vs SS).

FIG. 25 represents the average change in HbA1c (%) from baseline in patients with LS-DMR and SS-DMR (p<0.05 for the difference at 3 months).

These clinical studies did not specify a medication treatment algorithm for the treating diabetologist to prescribe. Note that the treating diabetologist was not made aware of the patients' treatment allocation when determining the appropriate post-procedure management strategy. As such, clinical decisions with respect to medication adjustments in individual patients were made but these adjustments were not well controlled with respect to a rigorous efficacy evaluation. By the time of the six month post-procedure follow up visit, several patients experienced changes to their glycemic medications that would be expected to confound efficacy analysis at later time points (see the chart further below). In particular, 13 out of 26 LS-DMR patients experienced reductions in medications and 1 patient experienced an increase in medication prescription, compared to 4 with reductions and 3 with increases among the SS-DMR patients.

The chart below represents the number of patients in each treatment arm with medication changes preceding the six month post-procedure followup visit.

| Treatment Received | Patients with reduction in glycemic meds | Patients with no med changes | Patients with increases in glycemic meds |
| --- | --- | --- | --- |
| LS-DMR | 13 | 12 | 1 |
| SS-DMR | 4 | 3 | 3 |

At 6 months, LS-DMR patients experienced a decline in HbA1c of 1.6% (SD 1.6%) on average (n=26) despite the fact that 13 of 26 patients had reductions in glycemic medicines that would be expected to mask the magnitude of the procedure's treatment effect. The impact of medication reductions is evident in the analysis of fasting plasma glucose (FPG) in LS-DMR patients whose baseline HbA1c was between 7.5% and 10%. Patients whose meds were unchanged after the procedure ("stable meds" group in left graph below) retain stable FPG between week 12 and week 24. Patients, whose medicines were reduced, however, experienced a decay in treatment effect, the timing of which is coincident with the timing of prescribed medication reductions.

FIGS. 26A and 26B represents the average fasting plasma glucose in LS-DMR patients with baseline HbA1c between 7.5% and 10%. The graph on the left shows FPG in all patients ("all patients"), the subset who experienced medication reductions ("meds decreased") and those whose medications were held constant through 24 week follow up ("stable meds"). The graph on the right shows the effect of medication reductions within the first 12 weeks ("meds decreased early") compared to those with medication reductions between week 12 and week 24 ("meds decreased late"). The timing of medication reductions corresponds to the timing of worsening FPG measurements.

Analysis of patients on consistent medications with a baseline HbA1c of between 7.5% and 10% revealed a mean HbA1c of 8.6 (SD 0.9; n=7) at baseline, 6.6 (SD 0.8; n=7) at 3 months, 7.2 (SD 0.6; n=6) at 6 months, and 7.3 (SD 0.3; n=4) at 12 months post procedure. These patients also experienced a reduction of fasting plasma glucose of 32 mg/dl (SD 21) at 3 months, 36 mg/dl (SD 24) at 6 months, and 20 mg/dl (SD 15) at 12 months.

Figure 27:
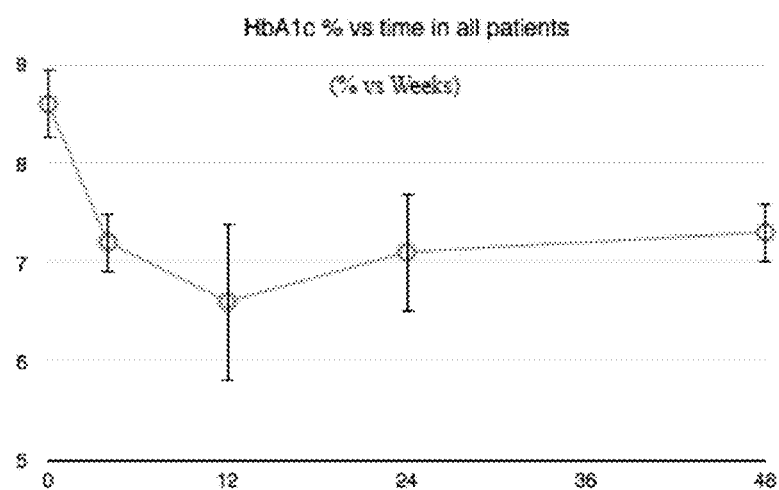
FIG. 27 is a graph showing mean HbA1C in LS-DMR patients with baseline HbA1c between 7.5% and 10% and consistent antidiabetic medications.

FIG. 27 represents mean HbA1c in LS-DMR patients with baseline HbA1c between 7.5% and 10% and consistent antidiabetic medications. Taken together, HbA1c measurements and fasting plasma glucose levels in LS-DMR patients with a baseline HbA1c level between 7.5% and 10% suggest durability of treatment response through 12 months of follow up.

Patient quality of life was assessed using the SF-36 standardized questionnaire. At screening, LS-DMR patients had a physical composite score (PCS) of 47 (SD 9) and a mental composite score of 46 (SD 11). At 6 months, patients in the LS-DMR group saw an increase in PCS of 3.1 points (SD 10; n=22) and MCS of 3.4 points (SD 14; n=22; p<0.05). The data suggest an improvement in the mental quality of life for poorly controlled diabetic patients who received LS-DMR.

Patients received a follow-up endoscopy at 1 month and/or 3 months post-procedure per protocol. Of the 19 patients who have received a follow-up endoscopy at 1 month, 4 patients had a reduction in height and/or width of plicae in the duodenum near the treatment area but otherwise the mucosa appeared to be healing normally with no scarring. No luminal narrowing indicative of stenosis was present in any of the 1 month endoscopies. Of the 37 patients who have received a follow-up endoscopy at 3 months, two patients had an endoscopically apparent reduction in height and/or width of plicae in the duodenum near the treatment area. All other patients had normal endoscopies with the mucosa fully healed and no evidence of scarring. No luminal narrowing was observed in any of the 3 month endoscopies. These results indicate that the treatment can effectively ablate the mucosa without damage to the duodenal structure and that the mucosa regrows quickly within the ablated region. The reduction in height and width of the plicae may be indicative of a reduction in the mucosal redundancy as part of the normal healing process.

A second procedure of the present inventive concepts was performed in 3 previously treated patients. There were no particular procedural challenges or significant adverse events associated with the second procedure in these three patients. Two patients had been non-responders to initial procedure, and their second procedure did not successfully improve glycemic control. A third patient had an improvement in glycemic control through 3 months after the first procedure, but this benefit was not fully sustained through the 6 month follow up visit. A repeat procedure was performed in month 8, and the patient has since been followed for six months after the second procedure. 14 months after the first procedure, therefore, the patient has an HbA1c of 7.3% (reduction of at least 2%) and a FPG of 100 mg/dl.

Figure 28:
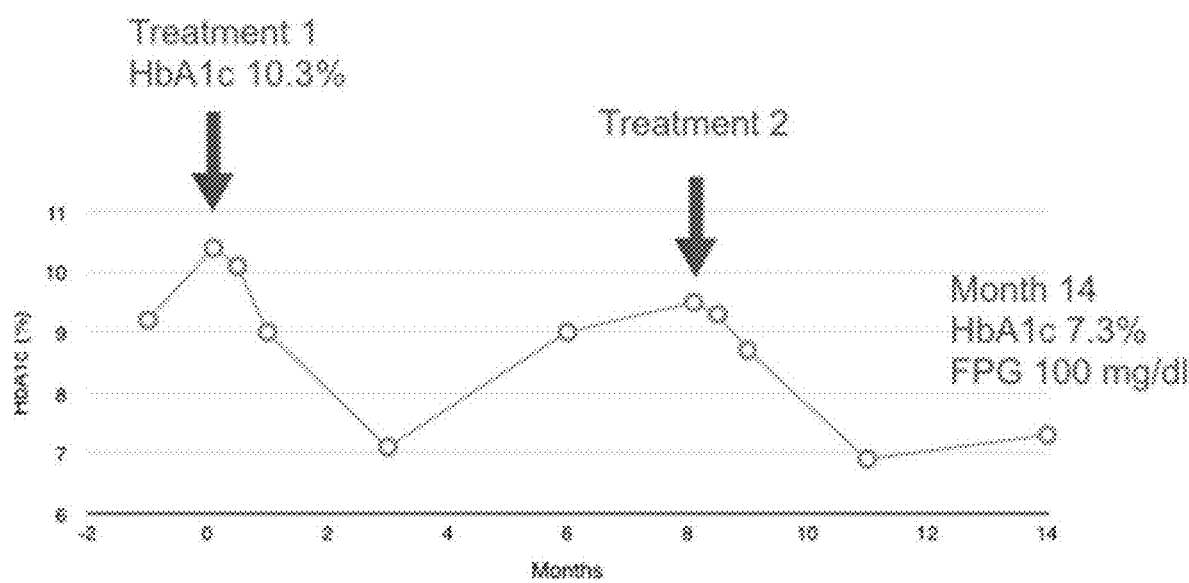
FIG. 28 is a graph showing HbA1c over time in a single patient receiving two treatments at different intervals.

FIG. 28 represents HbA1c over time in a single patient receiving two treatments (at month 0 and month 8, respectively).

The above summary provides clinical data on 39 patients enrolled and treated in an initial study focused on procedural and patient safety and clinical effectiveness. The results demonstrate that the procedure can be safely completed with devices performing as intended, that the procedure can be well tolerated by patients, and that there exists a strong suggestion of significant clinical effectiveness. The limited number and transient nature of adverse events suggest that the safety profile of the technology and procedure is favorable. Although there were three adverse events of duodenal stenosis formation, all were endoscopically treated with non-emergent endoscopic balloon dilation using techniques familiar to operators and resolved with no long-term sequelae. Other significant potential risks, including pancreatitis, perforation, bleeding, infection, or ulcer, have not been observed. No evidence for malabsorption, severe hypoglycemia, or late complications was found. The experience thus far indicates a safe procedure that can be well tolerated by patients. Mean HbA1c is reduced in treated patients despite net medication reductions in the patient cohort. In addition, a statistically significant dosimetric treatment response is also observed, with LS-DMR patients responding more effectively than SS-DMR patients. In addition, LS-DMR patients experienced more medication reductions (to prophylactically avoid hypoglycemia) than SS-DMR patients. This observation was made despite the fact that neither patients nor the treating endocrinologist was aware of the length of treated tissue in individual patients. Furthermore, 23/27 LS-DMR patients experienced an HbA1c reduction of at least 1% at 3 months of follow up, compared to 6/10 SS-DMR patients. Patients on consistent medications with a baseline HbA1c of between 7.5% and 10% showed evidence of a durable response to treatment, with persistent reductions in HbA1c and fasting glucose through 12 months of treatment follow up. This durable treatment response is observed even without aggressive diabetes management on the part of the treating physician, such as may be achieved through education, lifestyle recommendations, or aggressive pharmacotherapy. The treatment of the present inventive concepts may offer an even more significant and durable clinical effect when coupled with intensive medical management. The treatment effect does not appear to be weight dependent. Patients did not report any food intolerance or change in food preference that might explain this HbA1c reduction. While patients lost a small amount of weight, the magnitude of weight loss is likely not enough to explain the degree of HbA1c improvement. Furthermore, there did not appear to be any correlation between the magnitude of HbA1c reduction and weight loss.

In some embodiments, the systems, device and methods of the present inventive concepts can reduce the need for insulin therapy in a larger proportion of patients, such as to provide durable glycemic control with or without the therapies administered to the patient prior to the treatment of the present inventive concepts, or with a decrease in dosage of one or more previously administered medications.

The systems, devices and methods of the present inventive concepts can be configured to treat patients with microvascular disease or patients with a high risk of microvascular disease, such as to improve patient health and/or eliminate or otherwise reduce the need for one or more medications (e.g. one or more insulin medications). The treatment can be configured to reduce diabetic retinopathy (e.g. as shown in a reduction in diabetic retinopathy score), proteinuria and/or peripheral neuropathy severity. Additionally or alternatively, the treatment can be configured to reduce the effects of macrovascular disease such as myocardial infarction, stroke, peripheral vascular disease, CV death, and combinations of these.

Figure 3:
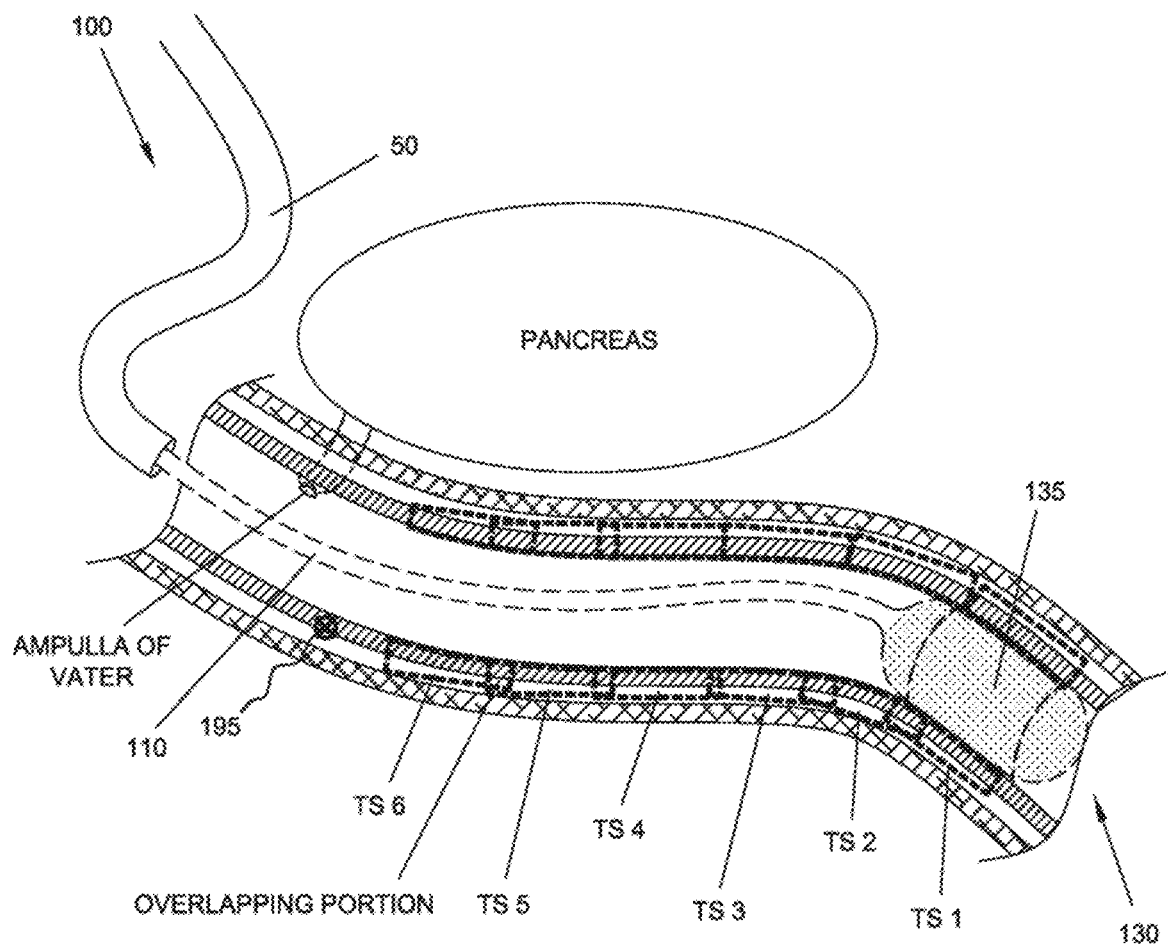
FIG. 3 is a side sectional view of the distal portion of a tissue treatment device inserted into a curvilinear section of duodenum, consistent with the present inventive concepts.

Referring now to FIG. 3, a side sectional view of the distal portion of a tissue treatment device inserted into a curvilinear section of duodenum is illustrated, consistent with the present inventive concepts. Tissue treatment device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control device 100, such as is described hereabove in reference to device 100 of FIG. 1. Tissue treatment device 100 can be configured for delivery over a guidewire, via a lumen from a proximal portion of shaft 110 to a distal portion of shaft 110, or via a rapid exchange sidecar or other lumen in the distal portion of shaft 110 (guidewire lumen and sidecar not shown but known to those of skill in the art). Shaft 110 is shown inserted through introducer 50 which can comprise an endoscope, sheath, vascular introducer, laparoscopic port, or other body introduction device.

Tissue treatment device 100 further comprises a treatment assembly, expandable assembly 130, which can include a balloon and/or be of similar construction and arrangement as expandable assembly 130 of FIG. 1. Fluid at an ablative temperature (i.e. a sufficiently high or low temperature to ablate tissue), treatment element 135, has been delivered to expandable assembly 130, as described hereabove, to deliver energy to one or more portions of a delivery zone and to treat one or more portions of target tissue.

A marker 195 has been positioned on the wall of the GI tract to be used as a reference to identify non-target tissue (e.g. a marker placed on tissue in relation to the ampulla of Vater, such as at a location distal to but proximate the ampulla of Vater). Marker 195 can comprise an element selected from the group consisting of: a visible marker (e.g. visible via camera 52 of endoscope 50); a radiographic marker; an ultrasonically visualizable marker; a magnetic marker; ink; dye; and combinations of these. Marker 195 can comprise multiple markers positioned in various locations (e.g. various locations used as a reference to identify multiple different or similar segments of non-target tissue.

Expandable assembly 130 has been positioned in a distal portion of duodenal tissue, such as a section that includes a previously expanded segment of submucosal tissue (submucosal tissue expansion not shown). Expandable assembly 130 has been radially expanded such as to contact the mucosal surface of the duodenum at a discrete tissue segment of target tissue, tissue segment TS1 as shown. Tissue segment TS1 is located distal to a series of sequential tissue segments of target tissue, tissue segments TS2 through TS6 as shown. Expandable assembly 130 and treatment element 135 (ablative fluid) are shown in FIG. 3 positioned to ablate or otherwise treat tissue segment TS1. Each of tissue segments TS1 through TS6 has a corresponding delivery zone (not shown) to which energy is delivered from expandable assembly 130 to cause the appropriate treatment of target tissue. In some embodiments, a series of adjoining segments are treated sequentially (i.e. from distal segment TS1 to each correspondingly more proximal segment TS2 through TS6 or from proximal segment TS6 to each correspondingly more distal segment TS5 through TS1). In some embodiments, a complete treatment comprises treatment of at least three adjacent segments (e.g. TS1 through at least TS3, TS2 through at least TS4, TS3 through at least TS5 or TS4 through at least TS6). Alternatively, a non-continuous pattern can be treated (e.g. TS1 followed by TS3 followed by TS2, and the like). In some embodiments, marker 195 is positioned in reference to the ampulla of Vater (e.g. proximate the ampulla of Vater), and all segments to be treated are positioned distal to the ampulla of Vater, such as can be determined by visualizing marker 195.

Expandable assembly 130 can be sized to allow positioning in curved segments of the GI tract with a minimum radius of curvature, such as a curved segment of the duodenum and/or jejunum with an average radius of curvature less than 5 cm over a 75° arc, or less than 3 cm over a 75° arc. In these curved segments (and straighter segments as well), expandable assembly 130 can be expanded without exerting undesired force onto tissue (e.g. expanded to contact the tissue wall). In some embodiments, expandable assembly 130 is constructed and arranged to treat curved segments of the GI tract and comprises a length less than or equal to 30 mm, such as less than or equal to 25 mm, less than or equal to 20 mm, or less than or equal to 15 mm.

After treatment of tissue segment TS1, expandable assembly 130 can be repositioned to tissue segment TS2, just proximal to tissue segment TS1, with or without contracting expandable assembly 130 prior to the repositioning. Subsequently, a second tissue treatment (e.g. a second energy delivery) can be performed. The steps of repositioning and treating portions of target tissue are repeated until one or more of tissue segments TS3, TS4, TS5, and TS6 have been treated. In some embodiments, an ablation reducing step is performed after each tissue segment treatment, such as by delivering a treatment neutralizing cooling fluid after a hot fluid ablation or delivery of a treatment neutralizing warming fluid after a cool (e.g. cryogenic) ablation, each as described herein. Alternatively or additionally, a cooling or warming fluid can be delivered, prior to a heat or cryogenic ablation, respectively, as described herein.

In a single clinical procedure, the combined length of target tissue segments TS1 through TS6 can represent between 10% and 100% of the length of the duodenal mucosa length distal to the ampulla of Vater, such as when between 2 and 50 axial segments of tissue receive between 2 and 50 energy deliveries from expandable assembly 130 (e.g. ablative fluid 335 is introduced into expandable assembly 130 2 to 50 sequential times). In some embodiments, each of tissue segments TS1 through TS6 have a maximum axial length of less than 20 cm, less than 15 cm, less than 10 cm, less than 5 cm, less than 3 cm or less than 2 cm. In some embodiments, the cumulative axial length of tissue segments treated, (e.g. two or more of tissue segments TS1 through TS6) is less than 100 cm, less than 50 cm, less than 25 cm, or less than 10 cm. In some embodiments, at least 6 cm or at least 9 cm of the duodenum is treated. Alternatively or additionally, other tissue (e.g. other tissue of the GI tract) can be treated, such as has been described hereabove.

Target tissue segments TS1 through TS6 typically include common border or overlapping tissue segments, such as is shown in FIG. 3. While the embodiment of FIG. 3 shows six target tissue segments being treated, more or fewer segments can be treated. In some embodiments, three axial tissue segments are treated (e.g. TS1, TS2 and TS3). In some embodiments, four axial tissue segments are treated (e.g. TS1, TS2, TS3 and TS4). In some embodiments, five axial tissue segments are treated (e.g. TS1, TS2, TS3, TS4 and TS5). In some embodiments, all GI tract tissue treated is distal to the ampulla of Vater.

Tissue treatments can be performed in a contiguous manner (e.g. a 1st portion, followed by a 2nd portion whose distal end is proximate the proximal end of the 1st portion, followed by 3rd portion whose distal end is proximate the proximal end of the 2nd portion, etc); however any order can be performed. In some embodiments, multiple contiguous or discontiguous tissue segments are treated simultaneously. In some embodiments, contiguous tissue segments are treated by device 100 continuously, as expandable assembly 130 is relatively continuously translated proximally and/or distally, such as via a manual or automated retraction and/or advancement, respectively, as is described in reference to FIG. 6 herebelow. In some embodiments, treatment of target tissue is performed as expandable assembly 130 translates at a rate of at least 1 cm per minute, at least 2 cm per minute, at least 5 cm per minute, or at least 10 cm per minute. In some embodiments, a segment of non-treated GI tissue is positioned between two segments of treated GI tissue, such as a non-treated segment of GI tissue in a sharp bend.

Referring now to FIGS. 4A, 4B and 4C, perspective, side and end views, respectively, of an expandable element comprising a balloon is illustrated, consistent with the present inventive concepts. Balloon 136 comprises an expandable element of the present inventive concepts, which can be configured receive a treatment element comprising fluid at an ablative temperature for treating target tissue, such as balloon 136 of FIG. 1 described hereabove. Balloon 136 can be constructed and arranged of one or more biocompatible materials, such as a material selected from the group consisting of: polyethylene terephthalate (PET); nylon; latex; polyurethane; and combinations of these. In some embodiments, balloon 136 comprises a wall thickness, Dim G, such as a wall thickness between 0.0002" and 0.0010", such as a wall thickness of approximately 0.0005".

In some embodiments, balloon 136 comprises a tissue contacting portion with a diameter of Dim A as shown. Dim A can comprise a diameter of approximately between 16.0 mm and 35.0 mm, such as a diameter between 19.0 mm and 32.0 mm. In some embodiments, balloon 136 comprises a tissue contacting portion, with a length defined by Dim D as shown. Dim D can comprise a length between 16.0 mm and 35.0 mm, such as a length between 19.5 mm and 32.9 mm. In some embodiments, balloon 136 comprises a tapered distal end, distal taper DT, which transitions from the tissue contacting portion with a curved segment, Dim B, with a radius between 7 mm and 9 mm, such as a radius of approximately 8 mm. Distal taper DT can comprise a taper, Dim F as shown, such as a taper between 270 and 33°, such as a taper of approximately 30°. In some embodiments, balloon 136 comprises a tapered proximal end, proximal taper PT, which transitions from the tissue contacting portion with a curved segment, Dim C, with a radius between 0.4 mm and 0.6 mm, such as a radius of approximately 0.5 mm. Proximal taper PT can comprise a taper, Dim E as shown, such as a taper between 420 and 48°, such as a taper of approximately 45°.

In some embodiments, the tissue contacting portion of balloon 136 comprises a surface area of between 1750 mm$^2$ and 2150 mm$^2$, such as a surface area of approximately 1950 mm$^2$. In some embodiments, a system of the present inventive concepts (e.g. system 10 of FIG. 1) comprises multiple tissue treatment devices (e.g. device 100 of FIG. 1), each comprising a balloon 136 with different tissue contacting portion lengths and/or diameters. In these embodiments, the surface area of the tissue contacting portion can comprise a relatively equivalent area for each device, such as when each tissue contacting portion surface area comprises an of between 1750 mm$^2$ and 2150 mm$^2$, such as a surface area of approximately 1950 mm$^2$. Similar surface areas for the different tissue treatment device's tissue contacting portions provide the advantage of: similar ablative fluid delivery settings; similar change in balloon temperature with fluid replacement (i.e. between cold and hot water or hot and cold water) to allow a steep "shoulder" of thermal profile within the balloon; similar uniformity of thermal profile along the balloon surface such as during the replacement of cold/hot water with one another within the balloon; similar tissue contact along the surface of the balloon including in bends of the GI tract.

Balloon 136 can be constructed and arranged to be filled with a particular volume of fluid (e.g. ablative fluid), such as a volume of between 10 ml and 35 ml, such as a volume between 12.5 ml and 30.0 ml. Balloon 136 can comprise a tubular stem extending from each of distal taper DT and/or proximal taper PT, such as to facilitate fluid attachment of balloon 136 to a shaft, such as shaft 110 of FIG. 1.

In some embodiments, the systems of the present inventive concepts can comprise two or more balloons 136, such as a first balloon 136 used in a first tissue treatment device (e.g. device 100 of FIG. 1 or FIG. 6) and a second balloon 136 used in a second tissue treatment device (e.g. device 100' of FIG. 6). The first balloon 136 and the second balloon 136 can comprise similar or dissimilar properties, such as similar or dissimilar tissue contacting lengths and/or diameters, such as to treat different segments of the GI tract.

Figure 5:
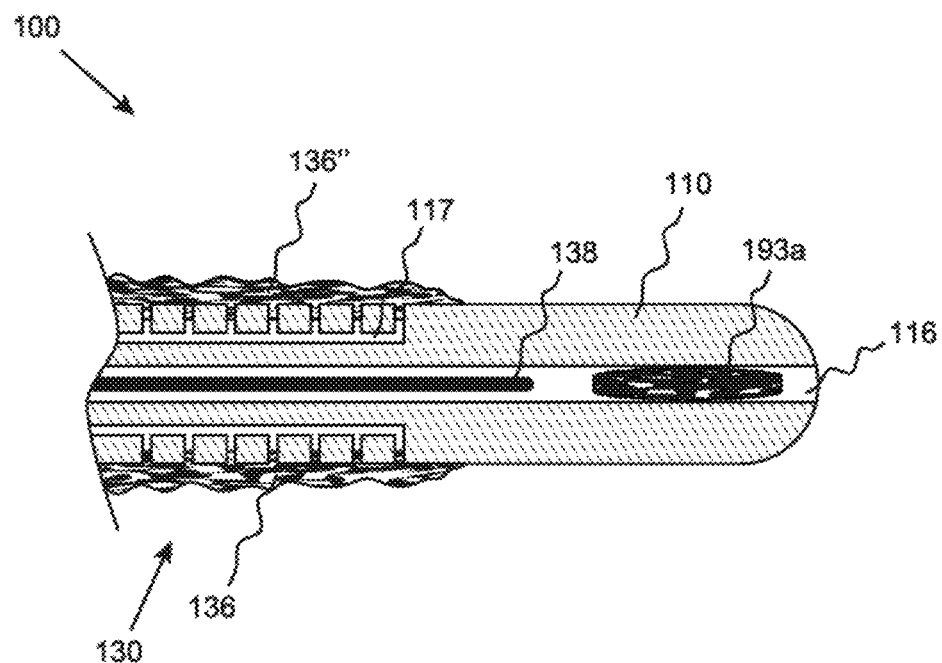
FIG. 5 is a side sectional view of the distal portion of a tissue treatment device including an agent dispensing element, consistent with the present inventive concepts

Referring now to FIG. 5, a side sectional view of the distal portion of a tissue treatment device including an agent dispensing element is illustrated, consistent with the present inventive concepts. Tissue treatment device 100 comprises shaft 110 which includes lumen 116 exiting the distal end of shaft 110. Positioned on a distal portion of shaft 110 is an expandable treatment assembly, expandable assembly 130 which includes a tissue treatment element, agent dispensing element 136". Shaft 110 and expandable assembly 130 are constructed and arranged such that shaft 110 can be inserted within and/or alongside an endoscope, such as endoscope 50 of FIG. 1. Lumen 116 and/or another lumen of shaft 110 can be constructed and arranged to allow over-the-wire delivery of shaft 110. Shaft 110 can comprise a length (e.g. at least 100 cm) such that expandable assembly 130 can be positioned proximate the distal end of the duodenum of a patient.

Agent dispensing element 136" is constructed and arranged to coat or otherwise apply one or more agents to target tissue. Tissue treatment device 100 and/or an associated system 10 can comprise one or more agents to be delivered by agent dispensing element 136", such as tissue modifying agent 135"; described herebelow in reference to FIGS. 5A-5E. Agent dispensing element 136" can comprise a material configured to expand, such as an expansion that occurs when agent dispensing element 136" comes into contact with a fluid (e.g. tissue modifying agent 135" or another fluid). Agent dispensing element 136" can be constructed and arranged to apply one or more tissue modifying agents 135" to target tissue. Tissue modifying agent 135" can comprise a chemical or other agent configured to cause target tissue necrosis or otherwise treat target tissue. Tissue modifying agent 135" can comprise an agent selected from the group consisting of: a chemical peeling agent; a mild acid such as glycolic acid; trichloroacetic acid; a mild base; phenol; retinoic acid; and combinations of these.

In some embodiments, agent dispensing element 136" comprises a material selected from the group consisting of: a sponge material (e.g. a natural or synthetic sponge material); a foamed polyurethane; a polyvinyl alcohol (PVA) sponge; a hydrogel; a super-absorbent polymer; and combinations thereof. Shaft 110 further includes lumen 117 which travels to a proximal portion of shaft 110 and is constructed and arranged to provide one or more fluids to agent dispensing element 136".

Device 100 can comprise one or more deployable occluding elements, such as occluder 193a, shown positioned within lumen 116 of shaft 110. Device 100 can further include translatable push rod 138 configured to be advanced to deploy occluder 193a from the distal end of lumen 116. Occluder 193a can be configured to radially expand to at least partially occlude a segment of the gastrointestinal tract, as described herebelow in reference to FIGS. 5A-5E, such as to prevent undesired migration of tissue modifying agent 135" to non-target tissue. Occluder 193 can comprise one or more expandable materials or elements such as an expandable balloon and/or an expandable sponge (e.g. similar to agent dispensing element 136"). Occluder 193 can include digestible and/or biodegradable materials. Occluder 193 can be configured to evacuate the body via the body's natural digestive system and/or to be removed such as via a grasping element deployed through an endoscope. In some embodiments, additional occluders 193 can be deployed via rod 138 and lumen 116, such as two occluders 193 positioned at opposite ends of a segment of GI tract to be treated by agent dispensing element 136", also as described herebelow in reference to FIGS. 5A-5E.

Device 100 of FIG. 5 can be included as part of a system, such as system 10 of FIG. 1 or FIG. 6. The system can include an agent delivery unit, such as a console 200, configured to deliver one or more agents to agent dispensing element 136", and the system can include the agent to be applied onto target tissue, tissue modifying agent 135". In some embodiments, agent 420 of FIG. 1 comprises tissue modifying agent 135".

Figure 5A:
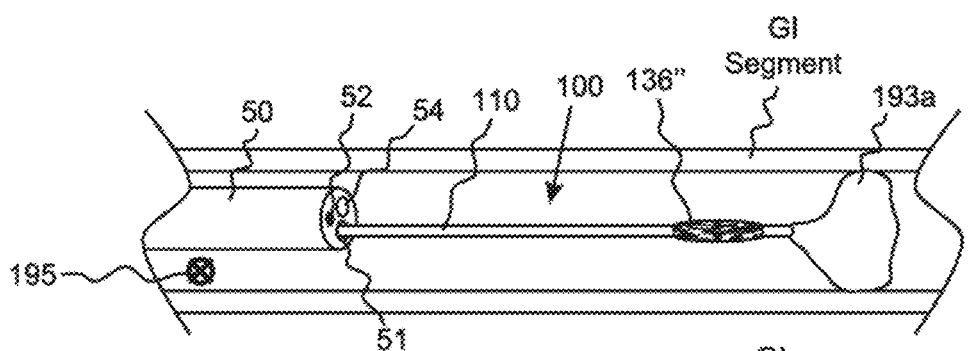
FIGS. 5A-5E are side sectional views of a series of steps for treating a surface of gastrointestinal tissue using the tissue treatment device of FIG. 5, consistent with the present inventive concepts.

Referring now to FIGS. 5A-5E, side sectional views of a series of steps for treating a surface of GI tissue with the tissue treatment device of FIG. 5 are illustrated, consistent with the present inventive concepts. In FIG. 5A, endoscope 50 has been inserted into a segment of GI tract as shown (e.g. the duodenum). Endoscope 50 includes multiple working channels, lumens 51 and 54, and a visualization device, camera 52. A marker 195 has been positioned on the wall of the GI tract to be used as a reference to identify non-target tissue (e.g. tissue of the ampulla of Vater that should not be treated). Marker 195 can comprise one or more markers of similar construction and arrangement and/or placement to marker 195 of FIG. 3 described hereabove. Marker 195 can be positioned on and/or in tissue using device 100 of FIG. 5 and/or another device such as endoscope 50.

Device 100 of FIG. 5 has been inserted through lumen 51 of endoscope 50 and advanced to a location distal to the position of marker 195 as shown. Occluder 193a is partially deployed from the distal end of shaft 110, such as via advancement of rod 138 described hereabove in reference to FIG. 5. Agent dispensing element 136" is in its radially compact state (e.g. prior to introduction of tissue modifying agent 135"). Device 100 can be of similar construction and arrangement to device 100 of FIG. 1 or device 100 of FIG. 6. In alternative embodiments, device 100 is inserted over a guidewire (e.g. not through endoscope 50) and/or through a sheath.

Figure 5B:
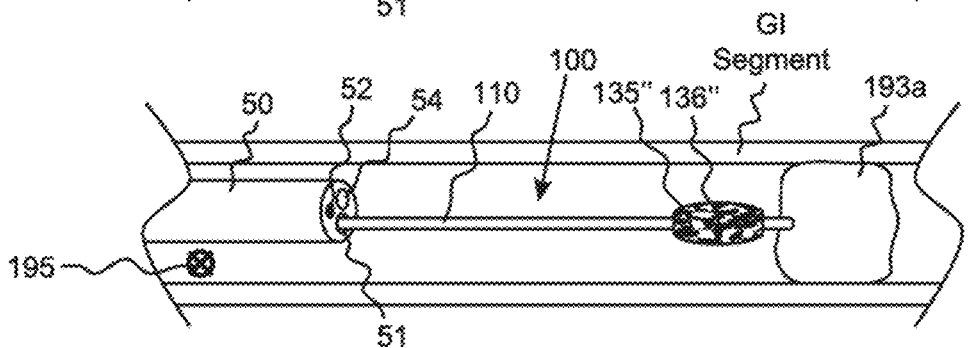

Referring now to FIG. 5B, occluder 193a has been deployed, and tissue modifying agent 135" is being introduced into agent dispensing element 136" such as to partially expand agent dispensing element 136". Tissue modifying agent 135" can be provided via a fluid delivery device (e.g. a fluid pump) fluidly attached to lumen 117 shown in FIG. 5. In some embodiments, the fluid delivery device is constructed and arranged as is described herein in reference to console 200 of system 10 of FIG. 1 or to energy delivery unit 250 and/or console 200 of system 10 of FIG. 6.

Figure 5C:
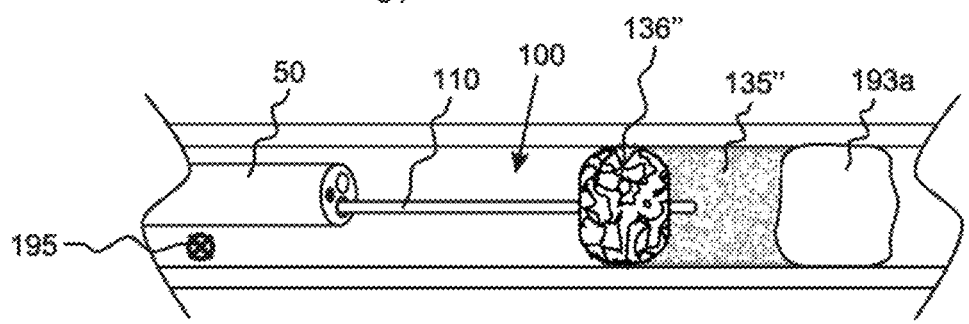

Referring now to FIG. 5C, agent dispensing element 136" has been fully expanded to contact the wall of the GI segment, and device 100 has been partially retracted such that tissue modifying agent 135" coats the full-circumferential wall, or at least a partial-circumferential portion, of the GI segment distal to agent dispensing element 136". During the retraction of device 100, tissue modifying agent 135" is provided (e.g. continuously provided) to agent dispensing element 136".

Figure 5D:
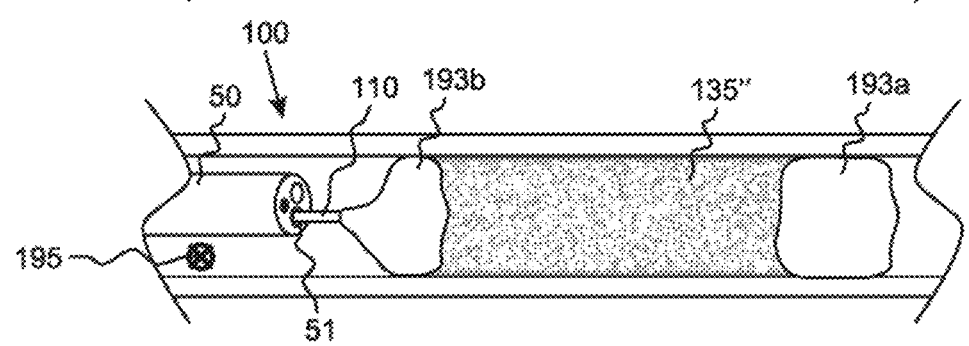

Referring now to FIG. 5D, device 100 has been further retracted to a proximal end of the GI segment to be treated. Additionally, flow of tissue modifying agent 135" to agent dispensing element 136" has been stopped, agent dispensing element 136" has been withdrawn into lumen 51 of endoscope 50 (leaving the distal end of shaft 110 extending out of endoscope 50), device 100 has subsequently been even further retracted, and a second occluding element, occluder 193b has subsequently been partially deployed from the distal end of shaft 110 (e.g. via control rod 138 in a similar fashion to the deployment of occluder 193a).

In some embodiments, agent dispensing element 136" is radially compressed prior to capture into lumen 51 (e.g. via application of a dehydrating agent, application of a vacuum capture via an advanceable sleeve, and the like). In some embodiments, a second agent (e.g. a neutralizing agent configured to stop and/or reverse the effects of tissue modifying agent 135") is delivered by agent dispensing element 136" prior to capture of agent dispensing element 136" into lumen 51. Alternatively or additionally, the neutralizing or other agent can be delivered via lumen 54. Delivery of a neutralizing agent can be performed to prevent adverse effect to non-target tissue.

Figure 5E:
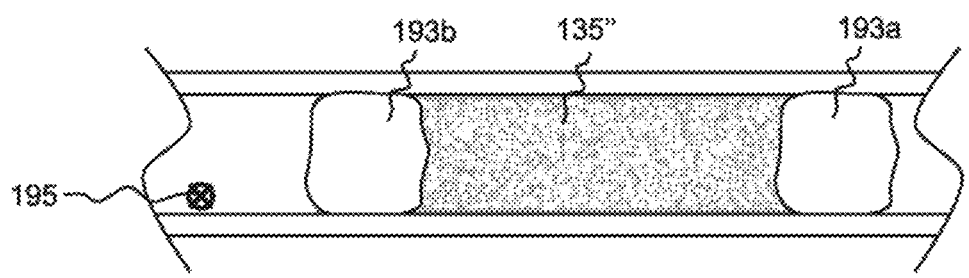

Referring now to FIG. 5E, occluder 193b has been fully deployed, and endoscope 50 and device 100 have been removed from the patient. Tissue modifying agent 135" is present on the inner layer (i.e. mucosal layer) of the GI segment between occluders 193a and 193b, such that this full circumferential segment can be treated. In some embodiments, the segment between occluders 193a and 193b defines the entire segment of tissue to be treated in that clinical procedure. In other embodiments, multiple segments (e.g. defined by additional occluders 193), can be treated in a single clinical procedure. In these single segment and multi-segment embodiments, the amount of target tissue treated with tissue modifying agent 135" (e.g. the inner tissue layer between occluders 193a and 193b as described in reference to FIGS. 5A-5E) can be selected as described herein (e.g. at least 10%, at least 15%, at least 20%, at least 25%, at least 30% or at least 50% of the length of the duodenum distal to the ampulla of Vater). In some embodiments, the amount of target tissue treated with device 100 of FIGS. 5 and 5A-5E is selected to cause the treatment achieved as described hereabove in reference to FIG. 2 and FIGS. 7-28. In some embodiments, the cumulative axial length treated is at least 4 cm, 5 cm, 6 cm, 7 cm, 8 cm or 9 cm of the duodenum.

Referring now to FIG. 6, a schematic view of a system for treating target tissue of a patient is illustrated, consistent with the present inventive concepts. System 10 includes tissue treatment device 100, which includes shaft 110 mounted on its proximal end to handle 102. Shaft 110 can comprise one or more shafts, such as outer shaft 110a and inner shaft 110b, slidingly received by outer shaft 110a. The distal portion of tissue treatment device 100 has been positioned in a segment of the GI tract. System 10 can further include tissue expansion device 20 and/or console 200, each of which can be of similar construction and arrangement to tissue expansion device 20 and/or console 200, respectively, of FIG. 1. Console 200 can be operably (e.g. fluidly, mechanically and/or electrically) attach to tissue treatment device 100, tissue expansion device 20 and/or another device or component of system 10, such as via one or more of ports 201. System 10 is configured to treat target tissue TT, which can include duodenal mucosa or other tissue as described herein to provide therapeutic benefit to the patient, such as the therapeutic benefits and other results presented in FIGS. 7-18. System 10 can be further configured to deliver an injectate into target tissue TT to expand tissue proximate target tissue TT (including target tissue TT itself), such as to expand one or more layers of tissue proximate target tissue TT.

System 10 can be configured to treat one or more patient diseases or disorders selected from the group consisting of: diabetes; pre-diabetes; impaired glucose tolerance; insulin resistance; obesity or otherwise being overweight; a metabolic disorder and/or disease; and combinations of these. In some embodiments, system 10 can be configured to treat one or more patient diseases or disorders selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease; stroke; TIA; cognitive decline; dementia; diabetic nephropathy; neuropathy; retinopathy; diabetic heart disease; diabetic heart failure; and combinations of these.

Treatment of target tissue TT can be performed after expanding target tissue TT and/or after expanding tissue proximate target tissue TT (e.g. expanding a submucosal layer of tissue and subsequently treating the neighboring mucosal layer of tissue). Tissue expansion by device 20 can greatly alleviate the need for precision of treatment, such as precision of delivery of energy, precision of debriding or other removal of tissue and/or precision of delivery of an ablative fluid, due to the increased size (e.g. increased depth) of the target tissue TT including an associated safety-margin of tissue to which treatment causes no significant adverse event (e.g. a submucosal layer expanded prior to neighboring mucosal layer ablation). In the embodiment of FIG. 6, target tissue TT includes one or more tubular tissue segments, such as one or more axial tissue segments within a body lumen of a mammalian patient. In some embodiments, target tissue TT expanded and/or treated comprises a continuous segment (e.g. a continuous, full-circumferentially treated segment) and/or multiple discontinuous segments (e.g. multiple full-circumferentially treated segments) of a duodenum, such as a volume of tissue comprising at least 15% of the duodenal mucosa distal to the ampulla of Vater, at least 20% of the duodenal mucosa distal to the ampulla of Vater, at least 25% of the duodenal mucosa distal to the ampulla of Vater, at least 30% of the duodenal mucosa distal to the ampulla of Vater, at least 50% of the duodenal mucosa distal to the ampulla of Vater, or at least 67% of the duodenal mucosa distal to the ampulla of Vater. The entirety of tissue treated can comprise tissue distal to the ampulla of Vater, such as in a procedure in which at least 50% of post-ampullary duodenal mucosa is treated.

In some embodiments, the target tissue TT comprises a treatment portion including duodenal mucosal tissue and a safety-margin portion comprising at least an innermost layer of the duodenal submucosa (e.g. an innermost layer of duodenal submucosa expanded by a device of the present inventive concepts). System 10 can be configured to treat the duodenal mucosa while avoiding damage to duodenal adventitial tissue (e.g. non-target tissue), such as by avoiding damage to: tissue beyond the mucosa; tissue beyond the superficial submucosa; and/or tissue beyond the deep submucosa. In some embodiments, system 10 comprises marker 195, such as marker 195 shown deployed in segment of the GI tract of FIG. 6 and described hereabove in reference to FIGS. 1 and 3. Marker 195 can be positioned or otherwise deployed via endoscope 50, device 100, and/or another device (e.g. a catheter device) of system 10.

System 10 can include one or more tissue treatment devices such as first tissue treatment device 100 and second tissue treatment device 100' (singly or collectively, device 100). First device 100 and/or second device 100' can be further constructed and arranged to expand tissue, as described in detail herein. Alternatively or additionally, system 10 can include separate tissue expansion device 20. First device 100 can be used in a first clinical procedure comprising expansion and/or treatment of target tissue TT, and second device 100' can be used in a second clinical procedure comprising expansion and/or treatment of target tissue TT. In some embodiments, the second clinical procedure is performed at least twenty-four hours after the first clinical procedure. Tissue expansions and/or treatments performed in the second clinical procedure can be constructed and arranged based on one or more outcomes of the first clinical procedure. Additional tissue expansion and/or tissue treatment devices can be included in system 10, such as to perform a third or other subsequent clinical procedures including tissue expansions and/or treatments.

First device 100 and second device 100' can be similar or dissimilar devices, and can be constructed and arranged to perform similar or dissimilar treatments to similar or dissimilar volumes of tissue. Differences between first device 100 and second device 100' can include but are not limited to: type of ablative treatment provided such as type of energy delivered; type of non-ablative treatment provided; type of tissue treatment assembly; type of tissue treatment element; length of the device; diameter of a portion of the device; and combinations of these. In some embodiments, first device 100 comprises a first tissue treatment element constructed and arranged to deliver a different form of energy than a second tissue treatment element of second device 100'. Alternatively or additionally, first device 100 can comprise a first tissue treatment element with a different geometry (e.g. different diameter, length and/or tissue contact surface area or shape), than a second tissue treatment element of second device 100'.

System 10 can include one or more body introduction devices, such as endoscope 50. Endoscope 50 can comprise a standard GI endoscope such as an endoscope with one or more working channels configured to slidingly receive first device 100 (as shown), second device 100' and/or another elongate device of system 10. Additionally or alternatively, system 10 can include other body introduction devices, such as a laparoscopic port, vascular introducer, sheath (e.g. a scope attached sheath such as sheath 80 of FIG. 1) and/or other introducer.

System 10 includes console 200, which includes user interface 205, controller 210, fluid source 220, vacuum source 230 and inflation source 240. Console 200, via ports 201, is operably connected to handle 102 of device 100 via tubes 203 and/or cable 202. User interface 205, controller 210, fluid source 220, vacuum source 230, inflation source 240, ports 201 can be of similar construction and arrangement to similar components of device 100 of FIG. 1.

System 10 can include injectate 221, which is delivered to device 100 or device 20 by fluid source 220. Injectate 221 can comprise a fluid selected from the group consisting of: water; saline; a fluid with a dye such as a visible dye such as indigo carmine; methylene blue; India ink; SPOT™ dye; a gel; a hydrogel; a protein hydrogel; a fluid containing a visualizable media such as a media visualizable under X-ray, ultrasound imaging and/or magnetic resonance imaging; ethylene vinyl alcohol (EVOH); and combinations of these. In some embodiments, injectate 221 can comprise a material constructed and arranged to cause a narrowing or other restriction that results in a therapeutic benefit to the patient, such as is described in applicant's co-pending International Patent Application Serial Number PCT/US2014/066829, entitled "Systems, Devices and Methods for the Creation of a Therapeutic Restriction in the Gastrointestinal Tract", filed Nov. 21, 2014, the entire content of which is incorporated herein by reference in its entirety. In these embodiments, injectate 221 can comprise a material configured to remain in place (e.g. within one or more tissue layers of the GI tract) for an extended period of time, such as at least 1 day, 1 week, 1 month, 3 months or 6 months. Injectate 221 can comprise a biopolymer (e.g. EVOH) and/or an adhesive (e.g. cyanoacrylate)

In some embodiments, console 200 comprises an energy delivery unit, EDU 250. EDU 250 can be constructed and arranged to deliver ablative fluids or other ablative energy to one or more components of device 100, such as an expandable tissue treatment assembly, expandable assembly 130 described herebelow, or to a separate tissue treatment device, such as device 100'. In some embodiments, console 200 comprises a motion control mechanism, motion transfer assembly 260. Motion transfer assembly 260 can be constructed and arranged to rotate, translate, vibrate and/or otherwise move one or more components of device 100, such as expandable assembly 130 and/or expandable assembly 160, each described in detail herebelow. In some embodiments, motion transfer assembly 260 is constructed and arranged to rotate another device or component of system 10, such as a tissue treatment element or other component of treatment device 100. In some embodiments, motion transfer assembly 260 is constructed and arranged to steer a shaft of one or more components of system 10, such as one or more shafts 110 of device 100.

Tissue treatment device 100 can comprise one or more shafts 110 (e.g. a single shaft or multiple columnal shafts) which attach on their proximal end to handle 102. A distal portion of one or more shafts 110 can include a radially expandable assembly 160 comprising one or more fluid delivery elements 168, each attached to a fluid delivery tube 162. Fluid delivery tubes 162 can travel proximally through one or more shafts 110 and into handle 102. Handle 102 can fluidly attach (e.g. via one or more ports and/or via tubes 203) to console 200 such that injectate 221 and/or another fluid can be provided to fluid delivery element 168 via fluid source 220. In some embodiments, two fluid delivery elements 168 are included (e.g. mounted 180° apart on expandable element 166). In some embodiments, three fluid delivery elements 168 are included (e.g. mounted 120° apart on expandable element 166). In some embodiments, four or more fluid delivery elements 168 are included (e.g. four elements mounted 90° apart on expandable element 166). In some embodiments, three or more fluid delivery tubes 162 are attached to expandable element 166 with spacing to accommodate advancement of endoscope 50 proximate to expandable element 166. A distal portion of one or more shafts 110 further include a tissue treatment assembly, expandable assembly 130 as shown. Expandable assembly 130 can be positioned distal or proximal (as shown) to expandable assembly 160 (i.e. when device 100 is configured to both treat tissue and expand tissue and includes both expandable assembly 130 for tissue treatment and expandable assembly 160 for tissue expansion).

Motion transfer assembly 260 can be configured to rotate expandable assembly 130 and/or expandable assembly 160 independently or in unison. Motion transfer assembly 260 can be configured to translate expandable assembly 130 as treatment is applied to a portion of target tissue TT. In some embodiments, contiguous tissue segments are treated by device 100 continuously as motion transfer assembly 260 causes expandable assembly 130 to translate at a rate of at least 10 cm/minute, or at a rate of at least 20 cm/minute. In some embodiments, expandable assembly 130 is manually translated, such as at a rate of at least 10 cm/minute, or at least 20 cm/minute. Motion transfer assembly 260 can be configured to translate expandable assembly 130 between a first tissue treatment and a second tissue treatment (e.g. between a first segment of duodenal mucosa treated in the first treatment and a second segment of duodenal mucosa treated in the second treatment). Motion transfer assembly 260 can include one or more rotational and/or linear drive assemblies, such as those including rotational motors, magnetic drives, lead screws and/or other linear actuators, and the like which are operably connected to shaft 110a and/or 110b. Shafts 110a and/or 110b are constructed with sufficient column strength and/or torque transfer properties to adequately rotate and/or translate expandable assembly 130 and/or expandable assembly 160, respectively. Motion transfer assembly 260 can be in communication with controller 210, such as to activate, adjust and/or otherwise control motion transfer assembly 260 and thus the motion of expandable assembly 130 and/or expandable assembly 160. Motion transfer assembly 260 can be manually driven and/or automatically (e.g. motor) driven. Alternatively or additionally, motion transfer assembly 260 can be used to advance and/or retract expandable assembly 130 and/or expandable assembly 160 from a first position to treat a first portion of target tissue, to a second position to treat a second portion of target tissue. In these embodiments, repositioning of expandable assembly 130 and/or expandable assembly 160 can be configured to provide overlapping treatment.

Shafts 110a and 110b can include one or more lumens passing therethrough, and can comprise wires and/or optical fibers for transfer of data and/or energy such as RF energy to a functional element. such as functional element 139 of expandable assembly 130 and/or functional element 169 of expandable assembly 160. Shafts 110a and/or 110b can comprise one or more shafts, such as one or more concentric shafts configured to deliver and/or recirculate hot and/or cold fluid through expandable assembly 130 and/or expandable assembly 160. In some embodiments, a heated fluid is used to pre-heat one or more device 100 components and/or to deliver a bolus of hot fluid energy, each as described in applicant's co-pending U.S. patent application Ser. No. 14/470,503, entitled "Heat Ablation Systems, Devices and Methods for the Treatment of Tissue, filed Aug. 27, 2014, the entire content of which is incorporated herein by reference in its entirety. Device 100 can comprise multiple tissue treatment assemblies, such as a second expandable assembly positioned proximal to the expandable assembly 130 and a third expandable assembly positioned distal to expandable assembly 130 (e.g. expandable assembly 160 as shown in FIG. 6).

The distal end of shaft 110 (e.g. the distal end of shaft 110b) can comprise a bulbous element, bulbous tip 115. In these embodiments, bulbous tip 115 can be sized to fit through a working channel of endoscope 50, such as when bulbous tip 115 has a diameter less than 6 mm or less than 4 mm. Alternatively, bulbous tip 115 can have a larger diameter, such as a diameter or other geometry configured to assist in smoothly traversing plicae, such as a diameter of at least 8 mm. In some embodiments, bulbous tip 115 comprises a diameter between 4 mm and 9 mm, such as a diameter between 4 mm and 6 mm. In some embodiments, bulbous tip 115 comprises at least a radiopaque portion.

Shafts 110a and 110b of FIG. 6 are sized and configured such that shaft 110a slidingly receives shaft 110b, such that they can be advanced and/or retracted in unison or independently. Differential motion between shafts 110a and 110b can be used to change the distance between expandable assembly 130 and expandable assembly 160. In some embodiments, motion transfer assembly 260 is configured to rotate and/or axially translate shafts 110a and/or 110b such that expandable assembly 130 and/or expandable assembly 160, respectively, are rotated and/or translated. In some embodiments, device 100 comprises a flexible portion (e.g. a flexible portion of shafts 110a and 110b, such as a flexible distal portion of shaft 110b) with a diameter less than 6 mm. In some embodiments, the flexible portion is configured to pass through a working channel of an endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and subsequently advanced to reach the esophagus, stomach, duodenum and/or jejunum; and/or rectally inserted into a patient, and subsequently advanced to reach the terminal ileum of that patient. In FIG. 6, shafts 110a and 110b have been inserted through a working channel (e.g. a 6 mm working channel), lumen 51, of endoscope 50, typically a GI endoscope. Shafts 110a and/or 110b can be inserted over a standard interventional guidewire, such as guidewire 60 shown exiting the distal end of shaft 110b. In an alternative embodiment, shafts 110a and 110b are positioned in a side-by-side configuration, such as to be placed in two separate lumens of endoscope 50 or in two other non-coaxial locations. In some embodiments, one or both of shafts 110a or 110b passes through a body lumen or other internal body location alongside endoscope 50 (i.e. not through lumen 51, traveling relatively parallel with but external to endoscope 50). Shaft 110a and/or 110b can include a manipulating element constructed and arranged to deflect and/or steer a distal portion of the shaft, such as via one or more handle 102 controlled and/or motion transfer assembly 260 controlled pull wires that extend and are attached to a distal portion of the shaft (pull wires not shown but well known to those of skill in the art), such as to deflect and/or steer expandable assembly 130 and/or expandable assembly 160 towards and/or away from tissue and/or assist in navigating expandable assembly 130 and/or expandable assembly 160 through tortuous anatomy.

Handle 102 can comprise one or more controls included in user interface 105. In some embodiments, user interface 105 comprises one or more controls selected from the group consisting of: electrical control; mechanical control; button; knob; switch; lever; touchscreen; and combinations of these. In some embodiments, a mechanical control is operably attached to a mechanical assembly, such as a cam or other mechanical advantage mechanism used to transmit a force (e.g. transmit force to a pull wire). In some embodiments, an electrical control is used to attach one or more components of system 10 to power and/or to activate an electrically powered mechanical mechanism such as a solenoid or an electronic valve. User interface 105 can be configured to allow an operator to initiate, regulate, modify, stop and/or otherwise control one or more functions of console 200 and/or device 100.

In some embodiments, user interface 105 comprises one or more knobs or other controls used to advance and/or retract one or more fluid delivery elements 168, positioned on expandable element 166 of expandable assembly 160, each described in detail herebelow. In some embodiments, one or more fluid delivery elements 168 are advanced and/or retracted via a force limiting assembly 140. Force limiting assembly 140 can be constructed and arranged to allow a single control (e.g. a sliding knob) to advance multiple fluid delivery elements 168 simultaneously. In some embodiments, advancement and/or retraction of one or more fluid delivery elements 168 is limited by one or more mechanical stops.

In some embodiments, user interface 105 comprises a button, touch screen display and/or other control used to initiate, regulate, modify, stop and/or otherwise control one or more parameters of console 200, such as a tissue expanding fluid parameter selected from the group consisting of: flow rate of tissue expanding fluid; duration of tissue expanding fluid flow; volume of tissue expanding fluid; temperature of tissue expanding fluid; pressure of tissue expanding fluid; a tissue expanding fluid threshold parameter level (e.g. maximum or minimum flow rate, duration, volume, temperature and/or pressure); type of tissue expanding fluid; and combinations thereof. In some embodiments, user interface 105 comprises a button, touch screen display and/or other control used to initiate, regulate, modify, stop and/or otherwise control one or more parameters of EDU 250, such as an ablation parameter selected from the group consisting of: flow rate of ablative fluid; volume of ablative fluid; pressure of ablative fluid; temperature of ablative fluid; type of energy delivered; type of RF energy delivered (e.g. monopolar, bipolar or both); amount of RF energy delivered (e.g. voltage, current and/or power delivered); and combinations of these.

Device 100 of FIG. 6 includes an outer shaft 110a and an inner shaft 110b (generally shaft 110 or shafts 110). Expandable assembly 160 is mounted to shaft 110b, and expandable assembly 130 is mounted proximal to expandable assembly 160, shown positioned on shaft 110a. In some embodiments, device 100 comprises a single shaft, and expandable assembly 130 and/or expandable assembly 160 are mounted to that single shaft. Expandable assembly 160 is constructed and arranged to deliver fluid, via one or more fluid delivery elements 168, into target tissue TT, such as to expand tissue proximate target tissue TT. In some embodiments, expandable assembly 160 can be configured in one or more various forms to treat, modify, manipulate, measure and/or diagnose target tissue TT and/or other tubular tissue. Expandable assembly 160 can comprise one or more expandable elements 166, such as one or more expandable elements selected from the group consisting of: an inflatable or otherwise expandable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. In some embodiments, expandable assembly 160 is inflatable (e.g. an inflatable balloon), and inflation fluid can be delivered into expandable assembly 160 via an inflation tube 161. Inflation tube 161 can comprise a lumen of shaft 110b (or a tube within shaft 110b) that travels proximally through shaft 110b and shaft 110a, such as to receive inflation fluid delivered by inflation source 240. Expandable assembly 160 can be positioned distal to expandable assembly 130 as shown in FIG. 6, or alternatively, expandable assembly 160 can be positioned proximal to expandable assembly 130, such as when expandable assembly 130 is mounted to shaft 110b and expandable assembly 160 is mounted to shaft 110a.

Expandable assembly 130 can be radially expandable, similar to expandable assembly 160 and/or it can include one or more radially expandable elements, such as those described hereabove in reference to expandable assembly 160 and/or expandable element 166. System 10 can be configured to allow expansion of expandable assembly 130 to cause one or more treatment elements 135 to approach and/or contact a tissue wall such as a duodenal wall, such as when one or more treatment elements 135 comprise an ablative fluid delivered to a balloon and configured to ablate tissue, or when one or more treatment elements 135 comprise an electrode configured to deliver RF energy to ablate tissue. Expandable assembly 130 can be configured to expand to a diameter less than the diameter of the target tissue TT, such as when a vacuum is applied to cause the target tissue TT diameter to decrease sufficiently to make contact with expandable assembly 130 and/or one or more treatment elements 135. System 10 can be configured to allow expansion of treatment assembly 130 to cause one or more treatment elements 135 to be positioned at a fixed distance from the luminal wall of tubular tissue, such as a positioning at a fixed distance of at least 250 microns, at least 500 microns, or at least 1 mm from a tissue wall, such as when one or more treatment elements 135 are configured to deliver ablative fluid to the target tissue TT and/or to deliver light energy to the target tissue TT. In addition to treating target tissue TT, treatment assembly 130 and/or one or more treatment elements 135 can be configured in one or more various forms to modify, manipulate, measure and/or diagnose target tissue TT and/or other tubular or non-tubular tissue. Expansion of treatment assembly 130 can occur prior to, during and/or after treatment of target tissue TT by treatment element 135. Treatment element 135 can be mounted on, within and/or inside of an expandable assembly, such as on, within and/or inside of an expandable balloon. Treatment assembly 130 can be constructed and arranged to expand and contact luminal wall tissue without applying an undesired force to the luminal wall tissue, such as by applying a pressure of less than 2.0 psi or less than 1.2 psi. Expandable assembly 130 can be constructed and arranged to expand to a diameter between 20 mm and 35 mm, such as to a diameter between 20 mm and 27.5 mm. Expandable assembly 130 can be constructed and arranged to contact luminal wall tissue with a pressure of at least 0.6 psi.

In some embodiments, expandable element 136 of expandable assembly 130 and/or expandable element 166 of expandable assembly 160 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable element 136 and/or expandable element 166 comprise a balloon which is fluidly attached to an inflation tube, such as inflation tube 161 which travels proximally through shaft 110a and/or 110b and is attached to one or more tubes 203 and/or an inflation port on handle 102.

In some embodiments, expandable assembly 160 is constructed and arranged to exert no more than a maximum threshold force on tissue, such as luminal wall tissue. The threshold force can comprise a force less than 2.0 psi, such as a force less than 1.2 psi. Expandable assembly 160 can be constructed and arranged to contact luminal wall tissue with a force of at least 0.6 psi. Expandable assembly 160 can be constructed and arranged to expand to a target diameter, such as a diameter of at least 10 mm, at least 15 mm, at least 25 mm, at least 30 mm or at least 40 mm. In some embodiments, expandable assembly 160 is constructed and arranged to expand to a diameter between 20 mm and 35 mm, such as a diameter between 20 mm and 27.5 mm. In some embodiments, expandable assembly 160 has its diameter controlled by a component of system 10 (e.g. controller 210 and/or inflation source 240), such as to control the diameter to at least 10 mm, at least 15 mm, at least 20 mm, at least 25 mm, at least 30 mm, or at least 40 mm, or to control the diameter to a diameter between 20 mm and 35 mm. In some embodiments, expandable assembly 160 is constructed and arranged to expand to its target diameter in less than 60 seconds, such as less than 30 seconds or less than 15 seconds. In some embodiments, expandable assembly 160 is expanded to a target diameter by inflating with fluid delivered at a constant pressure (e.g. approximately 0.7 psi) until the target diameter is reached. In some embodiments, expandable assembly 160 is constructed and arranged to expand to a diameter less than the diameter of the lumen of the GI tract proximate expandable assembly 160. In these embodiments, vacuum can be applied (e.g. via an endoscope 50 or device 100 insufflation port), which brings the tissue of the luminal wall toward a tissue capture port 167 and/or a fluid delivery element 168.

In some embodiments, expandable assembly 130 is constructed and arranged to exert no more than a maximum threshold force on tissue, such as luminal wall tissue. Expandable assembly 130 can be constructed and arranged to treat tissue while maintaining a pressure of at least 0.6 psi. Expandable assembly 130 can be constructed and arranged to expand to a target diameter, such as a diameter of at least 10 mm, at least 15 mm, at least 25 mm, at least 30 mm or at least 40 mm. In some embodiments, expandable assembly 130 is constructed and arranged to expand to a diameter between 20 mm and 35 mm, such as a diameter between 20 mm and 27.5 mm. In some embodiments, expandable assembly 130 has its diameter controlled by a component of system 10 (e.g. controller 210, inflation source 240 and/or EDU 250), such as to control the diameter to at least 10 mm, at least 15 mm, at least 20 mm, at least 25 mm, at least 30 mm, or at least 40 mm, or to control the diameter to a diameter between 20 mm and 35 mm. In some embodiments, expandable assembly 130 is constructed and arranged to expand to a diameter less than the diameter of the lumen of the GI tract proximate expandable assembly 130. In these embodiments, vacuum can be applied (e.g. via an endoscope 50 or device 100 insufflation port), which brings the tissue of the luminal wall toward expandable assembly 130 and/or treatment element 135.

In some embodiments, expandable assembly 130 and/or expandable assembly 160 comprise a length of at least 10 mm, such as a length between 10 mm and 40 mm, a length between 15 mm and 30 mm, or a length between 20 mm and 25 mm. In some embodiments, expandable assembly 130 and/or expandable assembly 160 comprise a length less than or equal to 15 mm, such as when configured to treat curvilinear portions of the GI tract. Multiple assemblies positioned on shafts 110a and/or 110b (e.g. between two and twenty treatments and/or expandable assemblies), such as expandable assembly 130 and expandable assembly 160, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and expandable assembly 160 is less than or equal to the expandable assembly 160 length. In these embodiments, expandable assembly 130 can comprise a similar length to that of expandable assembly 160, such as when both expandable assembly 130 and expandable assembly 160 comprise an ablation element as is described herebelow. Expandable assembly 130 and/or expandable assembly 160 can be sized, constructed and/or arranged to expand tissue and/or ablate tissue, or otherwise perform a function, while positioned in a curved segment of the GI tract.

Expandable assembly 130 and/or expandable assembly 160 can be resiliently biased, such as a resilient bias in a radially expanded or radially compacted state. In some embodiments, expandable assembly 130 and/or expandable assembly 160 are expanded and/or compacted by a control shaft, such as control shaft included in conduit 132 or another conduit of device 100 and manipulatable by an operator of system 10 and/or by motion transfer assembly 260. Expandable assembly 130 and/or expandable assembly 160 can be constructed and arranged to achieve a round or non-round shape (e.g. a football shape) when expanded. Expandable assembly 130 and/or expandable assembly 160 can approximate a tubular shape when expanded, such as a relatively constant diameter or varying diameter tubular shape. Expandable assembly 130 and/or expandable assembly 160 can be configured to un-fold to a radially expanded state, or to fold to a radially compacted state.

Expandable assembly 160 and at least one fluid delivery element 168 are configured to expand or otherwise modify tissue, such as to expand one or more layers of tissue. One or more fluid delivery elements 168 can comprise a needle, fluid jet and/or iontophoretic fluid delivery element configured to deliver injectate 221 into target tissue, such as to expand submucosal or other tissue of the GI tract. Console 200 can comprise a reservoir or control means for delivering a pre-determined amount of injectate 221 to tissue by device 100, such as a volume of fluid of at least 1 ml, or a volume of fluid of at least 2 ml, 5 ml, 10 ml or 25 ml. Device 100 can be configured to inject fluid into multiple injection sites (e.g. simultaneously or sequentially), such as a set of multiple injection sites selected from the group consisting of: at least 3 injection sites along a circumference of tubular tissue, a first circumferential injection site separated from a second circumferential injection site by approximately 1 cm, or between 0.5 cm to 5 cm, or between 1 cm and 3 cm, or between 1 cm and 2 cm; two or more injection sites that are axially and/or radially spaced; two or more injections sites that are separated based on the diameter of the tubular tissue into which they are injected; and combinations of these. Fluid can be injected with the assistance of one or more vacuum applying elements positioned on or near fluid delivery elements 168, such as tissue capture ports 167 shown. Tissue capture ports 167 can be of similar construction and arrangement to tissue capture ports 47 of FIG. 1 described hereabove. Tissue capture ports 167 are configured to apply negative pressure proximate the injection site, such as to capture tissue within the port and avoid the fluid delivery element 168 from having to radially exit tissue capture port 167 to penetrate the tissue. Tissue capture ports 167 can comprise one or more portions that are radiopaque. Console 200 and/or tissue capture ports 167 can be configured to discharge or otherwise release tissue from tissue capture port 167, such as by applying a positive pressure to tissue capture port 167. Device 100 can comprise one or more sensors configured to monitor the vacuum level in tissue capture port 167 and/or a fluidly connecting lumen.

As described hereabove, system 10 can be constructed and arranged to both expand tissue and treat tissue. In some embodiments, one or more devices 100 can be constructed and arranged to both expand tissue and treat tissue, such as via a tissue treatment assembly, expandable assembly 130. Alternatively or additionally, system 10 can comprise a separate device for tissue treatment, tissue treatment device 100'. Device 100' can comprise one or more tissue treatment elements configured to treat target tissue TT, such as a tissue treatment assembly similar to expandable assembly 130 described herein. Console 200 can further include an energy delivery unit, EDU 250, which can be operably attached to first device 100 (as shown), tissue second tissue treatment device 100' and/or tissue expansion device 20. EDU 250 can be configured to provide numerous forms of energy to one or more treatment elements of device 100 and/or device 100', such as an energy form selected from the group consisting of: RF energy; microwave energy; laser energy; sound energy such as subsonic sound energy or ultrasound energy; chemical energy; thermal energy such as heat energy or cryogenic energy provided by an ablative fluid; and combinations of these.

In some embodiments, system 10, device 100 and/or device 100' (singly or collectively device 100) can be constructed and arranged as is described in applicant's co-pending U.S. patent application Ser. No. 13/945,138, entitled "Devices and Methods for the Treatment of Tissue", filed Jul. 18, 2013, the entire content of which is incorporated herein by reference in its entirety. In some embodiments, device 100 can be constructed and arranged to ablate tissue with an ablation treatment selected from the group consisting of: delivery of thermal energy from a balloon filled with fluid at an ablative temperature; RF energy ablation such as monopolar and/or bipolar RF energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations of these. In some embodiments, device 100 can be constructed and arranged to perform a non-ablative treatment of target tissue, such as with a non-ablative treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations of these. Device 100 can be constructed and arranged to resect tissue, such as to resect tissue selected from the group consisting of: plicae tissue; mucosal tissue; submucosal tissue; and combinations of these.

One or more components of console 200 can include a pump and/or reservoir which can provide and/or remove one or more fluids to and/or from one or more devices of system 10, such as device 100, device 20 and/or endoscope 50. Fluids can be provided (e.g. by EDU 250) to thermally prime (e.g. hot or cold priming) one or more components of system 10, as described in detail hereinbelow. Tissue ablating fluids can be provided, such as hot or cold ablative fluids provided by EDU 250 to expandable assembly 130 of device 100. Tissue neutralizing fluids can be provided (e.g. by EDU 250) such as cooling fluids provided after elevated temperature ablation, warming fluids provided after cryogenic ablation and/or chemically neutralizing fluids delivered to neutralize a chemical agent. Fluids can be provided (e.g. a gas) to insufflate a portion of the GI tract, such as fluids provided through a lumen of endoscope 50 or a lumen of device 100. Console 200 can include one or more fluid reservoirs (e.g. one or more reservoirs included in fluid source 220, vacuum source 230, inflation source 240 and/or energy delivery unit 250) constructed and arranged to supply or receive fluids to and/or from device 100. In some embodiments, console 200 includes one or more reservoirs, one or more pumps, and one or more cooling or heating units such that console 200 recirculates or otherwise continuously provides one or more hot and/or cold fluids through a device of system 10, such as to recirculate fluid through one or more portions of device 100, device 20 and/or endoscope 50.

Expandable assembly 130 can include one or more elements constructed and arranged to ablate or otherwise treat target tissue TT, such as tissue treatment element 135 shown. Treatment element 135 can comprise one or more elements selected from the group consisting of: a bolus of ablative fluid; recirculating ablative fluid; continuously replenished ablative fluid; an electrical energy delivery element such as one or more electrodes constructed and arranged to deliver RF energy; a fluid delivery element such as a nozzle or permeable surface constructed and arranged to deliver ablative fluid directly in contact with target tissue TT; a balloon such as a balloon constructed and arranged to receive a bolus of ablative fluid and deliver hot or cold thermal energy to ablate target tissue TT; a balloon such as a balloon constructed and arranged to receive a recirculating ablative fluid and deliver hot or cold thermal energy to ablate target tissue TT; a laser energy delivery element such as an optical fiber, a focusing lens and/or other optical component; a sound energy delivery element such as a piezo-based element configured to deliver ultrasonic and/or subsonic energy; a tissue abrading element; and combinations of these. Treatment element 135 can be positioned on, in, within and/or passing through one or more components of expandable assembly 130, such as a balloon, cage, spline or other component as are described herein. Expandable assembly 130 and/or treatment element 135 can comprise an energy distribution element, such as one or more optical components configured to rotate, translate and/or otherwise distribute laser or other light energy to target tissue. In some embodiments, expandable assembly 130 and/or treatment element 135 comprise an energy distribution element including a rotating element such a rotating mirror; a rotating prism and/or a rotating diffractive optic. In some embodiments, device 100 comprises one or more fibers that deliver laser or other light energy to a treatment element 135 when expandable assembly 130 comprises a balloon filled with light-scattering material.

In some embodiments, device 100 delivers thermal (e.g. heat or cryogenic) energy to tissue, such as when expandable assembly 130 and/or treatment element 135 comprises an ablative fluid delivered to a balloon, and the ablative fluid comprises a hot or cold volume of fluid at a temperature sufficient to ablate tissue when the balloon contacts the tissue. The hot or cold volume of fluid can be provided to expandable assembly 130 via EDU 250. System 10 can be configured to deliver thermal energy to tissue as is described in applicant's co-pending U.S. patent application Ser. No. 14/470,503, entitled "Heat Ablation Systems, Devices and Methods for the Treatment of Tissue, filed Aug. 27, 2014, or as is described in applicant's co-pending International Patent Application Serial Number PCT/US2014/055514, entitled "Systems, Methods and Devices for Treatment of Target Tissue", filed Sep. 12, 2014, the entire contents of each of which is incorporated herein by reference in their entirety.

In some embodiments, device 100 delivers RF energy to tissue, such as when treatment element 135 comprises one or more electrodes constructed and arranged to receive RF energy provided by EDU 250. In these embodiments, the one or more electrodes can comprise one or more conductive dots or other conductive elements positioned on an expandable element such as a balloon. In some embodiments, EDU 250 is configured to deliver RF energy to one or more electrodes of device 100, such as in a monopolar mode through a grounding pad such as ground pad 70 and/or in a bipolar mode between two or more electrodes of device 100. System 10 can be configured to deliver RF energy to tissue as is described in applicant's co-pending U.S. patent application Ser. No. 14/609,332, entitled "Electrical Energy Ablation Systems, Devices and Methods for the Treatment of Tissue", filed Jan. 29, 2015, the entire content of which is incorporated herein by reference in its entirety.

In some embodiments, device 100 delivers ablative fluid directly to tissue, such as when treatment element 135 comprises one or more nozzles or other ablative fluid delivery elements. In these embodiments, treatment element 135 can be constructed and arranged to ablate target tissue TT by delivering ablative fluid provided by EDU 250. Treatment element 135 can include one or more fluid delivery elements selected from the group consisting of: nozzle such as a nozzle configured to deliver a cone or other shaped spray of fluid; needle; opening; hole; slit; permeable membrane; misting element; vaporizer; and combinations of these. Treatment element 135 can comprise the fluid delivery element and/or the ablative fluid. Ablative fluid can comprise one or more liquids or gases that are delivered to target tissue TT at a temperature above or below a threshold that would ablate tissue. In some embodiments, the ablative fluid delivered by treatment element 135 comprises steam, such as steam at a temperature of 100° C. or above. In some embodiments, the ablative fluid delivered by treatment element 135 comprises a vaporized fluid at a temperature below 100° C., such as a vaporized fluid at a temperature between 70° C. and 90° C. In some embodiments, the ablative fluid delivered by treatment element 135 comprises a gas, such as a gas between 60° C. and 99° C., such as a gas delivered to tissue at a temperature between 70° C. and 90° C. In some embodiments, the ablative fluid delivered by treatment element 135 comprises a vaporized liquid, such as a vaporized liquid delivered to tissue at a temperature below 100° C., such as at a temperature between 70° C. and 90° C. Alternatively or additionally, an ablative fluid delivered by treatment element 135 can comprise one or more liquids or gases that cause tissue necrosis or otherwise treat target tissue TT using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting neutralizing agent can be included, such as a neutralizing agent delivered by device 100 or another device or component of system 10 that is used to neutralize, impede, reduce and/or limit tissue ablation caused by the delivery of a necrotic agent-based ablative fluid. The counter-acting agent can be delivered by treatment element 135 and/or another component of device 100 or system 10. The neutralizing agent can comprise an agent selected from the group consisting of: anti-sclerotic agent; base; acid; buffer solution; saline; water; and combinations of these. System 10 can be configured to deliver ablative fluid directly to tissue as is described in applicant's co-pending U.S. patent application Ser. No. 14/609,334, entitled "Ablation Systems, Devices and Methods for the Treatment of Tissue", filed Jan. 29, 2015, the entire content of which is incorporated herein by reference in its entirety.

Expandable assembly 130 can be positioned on shaft 110a as shown. Treatment element 135 is electrically, fluidly, mechanically and/or otherwise operably connected to conduit 132. Conduit 132 can comprise one or more elongate filaments selected from the group consisting of: a wire such as one or more wires configured to deliver electrical or other power and/or transmit electrical or other data signals; an optical fiber such as one or more optical fibers configured to deliver power and/or transmit data signals; a tube such as a fluid delivery or a vacuum supplying tube; a lumen such as a fluid delivery lumen or a vacuum supplying lumen; a control rod such as an advanceable and/or retractable control rod; and combinations of these. Conduit 132 travels proximally through shaft 110a and operably attaches to console 200 (e.g. via one or more ports 201), such as to operably attach to one or more of: fluid source 220; vacuum source 230; inflation source 240; EDU 250; motion transfer assembly 260; and/or combinations of these, and/or to attach to another component, assembly or device of system 10. In some embodiments, one or more portions (e.g. one or more filaments) of conduit 132 extend to expandable assembly, such as one or more filaments selected from the group consisting of: a control rod; an inflation tube; an inflation lumen; a fluid delivery tube; a wire; an optical fiber; and combinations of these.

In some embodiments, conduit 132 comprises one or more fluid delivery tubes and/or lumens constructed and arranged to deliver and/or recirculate heated or chilled fluid into expandable assembly 130, such as heated or chilled fluid received from EDU 250 and delivered into treatment element 135, such as when treatment element 135 comprises ablative fluid and/or a balloon or other fluid reservoir receiving the ablative fluid, where the ablative fluid is at a temperature sufficient to ablate tissue when expandable assembly 130 contacts the tissue. Alternatively or additionally, conduit 132 can comprise one or more fluid delivery tubes constructed and arranged to deliver an ablative fluid to expandable assembly 130, such as ablative fluid provided by EDU 250 and delivered directly to target tissue TT by one or more treatment elements 135, such as when treatment element 135 comprises a fluid delivery element such as a nozzle. Conduit 132 can further comprise one or more insulating layers configured to prevent transfer of heat into and/or out of conduit 132. Conduit 132 can include a surrounding lumen which receives a circulating fluid configured to provide an insulating, warming and/or cooling effect on conduit 132 and/or any fluid contained within conduit 132. Conduit 132 and/or another fluid delivery tube of system 10 can comprise one or more elongate hollow tubes, such as a hollow tube positioned within shaft 110a. Alternatively, conduit 132 and/or another fluid delivery tube of system 10 can comprise a lumen within a shaft, such as a lumen within shaft 110a. In some embodiments, conduit 132 and/or another fluid delivery tube of system 10 comprises both a lumen and a hollow tube, such as when the lumen and hollow tube are fluidly connected in an end-to-end configuration. Conduit 132 typically attaches to console 200 with one or more operator attachable fluid connection ports (e.g. attaching to tubes 203), such as a fluid connection port included in handle 102 positioned on the proximal end of shaft 110a. Conduit 132 can comprise one or more fluid delivery tubes including one or more valves, not shown but such as a duck-bill or other valve used to regulate flow within conduit 132, such as to regulate flow pressure and/or direction.

In some embodiments, conduit 132 comprises one or more elongate filaments constructed and arranged to transmit energy and/or data. Conduit 132 can comprise one or more wires constructed and arranged to deliver RF energy to one or more electrode-type treatment elements 135, such as when the treatment elements 135 are configured to ablate target tissue TT in monopolar and/or bipolar modes as described herein. Conduit 132 can comprise one or more filaments constructed and arranged to deliver laser energy, such as one or more optical fibers constructed and arranged to deliver laser energy to one or more lenses or other optical component-type treatment elements 135, such as to ablate target tissue TT with laser or other light energy. Conduit 132 can comprise one or more wires or other energy transfer filaments constructed and arranged to allow a sound producing-type treatment element to ablate target tissue TT with sound energy such as ultrasonic or subsonic sound energy. Conduit 132 can comprise one or more wires or optical fibers configured to transmit information, such as information received from a sensor of system 10 as described herebelow.

In some embodiments, conduit 132 and/or shaft 110 comprises one or more control rods constructed and arranged to cause one or more treatment elements 135 and/or fluid delivery elements 168 to rotate and/or translate, such as when conduit 132 is operably attached to motion transfer assembly 260, such as prior to, during and/or after expansion of a tissue layer and/or delivery of energy to target tissue. In some embodiments, one or more treatment elements 135 comprise a surface configured to abrade or otherwise disrupt tissue as it is rotated and/or translated by movement of conduit 132. Alternatively or additionally, one or more fluid delivery elements 168 and/or treatment elements 135 can deliver energy and/or fluid to tissue, and movement of one or more control rod of conduit 132 and/or shaft 110 changes the location of the tissue segment receiving the energy and/or fluid. Motion of one or more fluid delivery elements 168 and/or treatment elements 135 can be configured to expand and/or treat a full circumferential (i.e. 360°) segment of tubular tissue, or a partial circumferential (e.g. 45°-350°) segment of tubular tissue. Motion of one or more treatment elements 135 and/or fluid delivery elements 168 can be configured to expand and/or treat a particular axial length of tubular tissue, such as an axial length comprising at least 15% of the axial length of the duodenum distal to the ampulla of Vater, or at least 20% of the axial length of the duodenum distal to the ampulla of Vater, or at least 25% of the axial length of the duodenum distal to the ampulla of Vater, or at least 30% of the axial length of the duodenum distal to the ampulla of Vater; or at least 50% of the axial length of the duodenum distal to the ampulla of Vater. In some embodiments, only tissue distal to the ampulla of Vater is expanded and/or treated, as has been described in detail hereabove.

EDU 250 can comprise multiple heat or cold sources used to modify the temperature of one or more fluids provided by and/or passing through EDU 250, console 200, device 100 and/or device 20. The heat or cold sources can be at a fixed temperature or they can be variable. In some embodiments, a first heat or cold source is at a fixed temperature and a second heat or cold source is at a variable temperature.

In some embodiments, a cooling fluid is delivered, prior to, during and/or after a heat ablation treatment of target tissue TT, such as to precisely control target tissue ablation and avoid ablation of non-target tissue. The cooling fluid can be provided by EDU 250 or another component of console 200, and it can be delivered to tissue, such as target or non-target tissue, and/or it can be delivered to a component of system 10 such as to reduce the temperature of a component of treatment assembly 160 or a component of device 500. Expandable assembly 130, expandable assembly 160, treatment element 135, fluid delivery element 168 and/or another component of system 10 can be constructed and arranged to deliver the cooling fluid to one or more tissue surfaces, such as a cooling fluid delivered to expandable assembly 130 via conduit 132 and/or a separate inflation tube or lumen (e.g. inflation tube 131 shown) and configured to reduce the temperature of one or more volumes of tissue (e.g. a cooling step performed prior to a hot fluid ablation step and/or a cooling step performed subsequent to a hot fluid ablation step). In some embodiments, system 10 is configured to deliver fluid at a sufficiently high temperature to ablate target tissue TT, after which a cooling fluid is automatically and/or semi-automatically delivered to remove thermal energy from target tissue TT and/or other tissue, such as cooling fluid delivered for a time period of at least 2 seconds, at least 5 seconds, at least 10 seconds or at least 20 seconds. In these embodiments, a cooling step can be performed prior to the heat ablation step, such as is described hereabove in reference to FIG. 2.

Ablation provided by system 10 can comprise a non-desiccating or a desiccating ablation. In some embodiments, a non-desiccating ablation is performed for a first portion of target tissue TT such as in a first tissue treatment, and a desiccating ablation is performed for a second portion of target tissue TT such as in a second tissue treatment. Non-desiccating ablations can be performed to treat overlapping portions of target tissue TT, and/or to avoid creation of tissue debris if desired. Desiccating ablations can be performed to achieve a higher thermal gradient, to remove excess tissue, and/or to ablate rapidly if desired. Console 200, treatment element 135 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of electrical current, such as through the innermost 50% of a mucosal layer, or through the innermost 20% of a mucosal layer. In some embodiments, system 10 can be configured to avoid detachment of tissue particles.

EDU 250 can be configured to deliver a hot or cold fluid to thermally prime (i.e. pre-heat or pre-chill, respectively) one or more components of system 10. In some embodiments, the one or more components include: conduit 132; a fluid delivery tube such as a tube within shaft 110*a* (e.g. inflation tube 131); a fluid delivery lumen such as a lumen within shaft 110*a* and/or shaft 110*b*; shaft 110*a*; shaft 110*b*; fluid delivery element 168; treatment element 135; and combinations of these. System 10 can be configured to thermally prime one or more components by circulating or recirculating hot fluid (pre-heat) or cold fluid (pre-chill), such as a hot or cold liquid or gas. In some embodiments, expandable assembly 130 contains and/or treatment element 135 delivers a hot fluid, and one or more components of system 10 are pre-treated with a hot gas. Alternatively or additionally, system 10 can comprise one or more insulators surrounding one or more conduits, lumens and/or shafts of device 100 and/or system 10, such as an insulator surrounding conduit 132 and/or tube 131 and configured to prevent transfer of heat across (e.g. into or out of) conduit 132 and/or tube 131.

Console 200, treatment element 135 and/or other components of system 10 can be configured to treat target tissue TT such that the temperature of at least a portion of the target tissue TT rises rapidly, such as at a rate of greater than or equal to 17.5° C. per second. Treatment can be delivered to cause the temperature of at least a portion of the target tissue TT to reach a setpoint temperature between 60° C. and 90° C., such as a setpoint temperature between 65° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 65° C. and 85° C. that is maintained for between 5 and 15 seconds. In some embodiments, after a setpoint temperature is achieved and/or maintained, the treatment can be adjusted (e.g. by adjusting energy delivery from EDU 250) such that tissue temperature decreases over time, such as to match a tissue response of the target tissue TT.

System 10 can be configured to maintain target tissue TT or other tissue under a threshold (e.g. below a maximum temperature of a heat ablation or above a minimum temperature of a cryogenic ablation) and/or within a temperature range, such as in a closed-loop configuration through the use of one or more sensors such as functional element 139 of expandable assembly 130 or functional element 169 of expandable assembly 160, each described in detail herebelow. In some embodiments, tissue temperature is maintained below 100° C., such as between 60° C. and 90° C., such as between 65° C. and 85° C. In some embodiments, system 10 is configured to maintain the temperature of target tissue TT at a setpoint temperature. The setpoint temperature can vary over time. System 10 can be configured to deliver energy at a level that increases and/or decreases over time. In some embodiments, treatment element 135 is constructed and arranged to cause the temperature of at least a portion of target tissue TT to rapidly rise to a setpoint (e.g. a setpoint between 60° C. and 75° C.). After the target tissue TT reaches the setpoint temperature, system 10 can deliver energy or otherwise treat the target tissue TT to maintain the setpoint temperature for an extended time period.

In some embodiments, EDU 250 is configured to heat or chill one or more fluids, such as one or more ablative fluids provided by EDU 250, or other fluids. In some embodiments, expandable assembly 130 is configured to heat or chill one or more fluids, such as when functional element 139 comprises a heating and/or cooling element. Applicable heating and cooling elements include but are not limited to heat exchangers, heating coils, peltier components, refrigeration assemblies, gas expansion coolers, and the like. Heating and cooling can be applied to a source of fluid (e.g. a reservoir of console 200), or to fluid that is withdrawn from device 100 (e.g. a recirculating fluid and/or a body extracted fluid such as recovered, previously delivered, ablative or insufflating fluid). EDU 250 can include one or more pumps configured to deliver and/or extract fluid at a particular flow rate, pressure, or other fluid delivery parameter.

Expandable assembly 130 and/or expandable assembly 160 can be configured to seal a body lumen location, such as to create a full or partial occlusive barrier at a location within the duodenum or other location in the GI tract. System 10 can be configured to cause a fluid or other seal comprising an occlusive barrier selected from the group consisting of: a pressure seal; a cryogenically applied seal such as an ice ball seal; a vacuum seal; a full circumferential seal; a partial circumferential seal; and combinations of these. In some embodiments, treatment element 135 treats a portion of target tissue TT located proximal or distal to the occlusive barrier. System 10 can include multiple expandable assemblies configured to seal a body lumen location, such as first expandable assembly which provides a seal at a proximal end of a segment of tubular tissue, and a second expandable assembly which provides a seal at a distal end of the tubular tissue segment. In some embodiments, treatment element 135 treats a portion of target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more treatment elements 135, via one or more functional elements 139 of expandable assembly 130 and/or functional element 169 of expandable assembly 160, and/or by another device or component of system 10. Applied vacuum can be used to modify (e.g. change the shape of) the tubular tissue between the two occlusive elements and/or to increase the sealing force and/or the circumferentiality of the seal. In some embodiments, system 10 is configured to deploy a detached-balloon configured to occlude a body lumen, where the detached-balloon can later be punctured or otherwise deflated for physiologic removal by the GI tract (e.g. similar to occlusive element 193 of FIGS. 5 and 5A-5E). Deployed balloons or other occlusive elements of system 10 can be positioned to protect tissue, such as to protect the ampulla of Vater and/or the pylorus from adverse effects that can be caused by treatment of target tissue TT by treatment element 135.

Expandable assembly 130 can comprise at least one functional element 139, and expandable assembly 160 can comprise at least one functional element 169, each as shown. Functional elements 139 and/or 169 can be elements selected from the group consisting of: a sensor; a transducer; an ablation element such as one or more electrodes configured to deliver electrical energy such as radiofrequency (RF) energy; a fluid delivery element such as a needle, a fluid jet, a permeable membrane and/or an exit port; a heating element; a cooling element; and combinations of these.

In some embodiments, expandable assembly 160 is configured to ablate tissue, such as via functional element 169. Functional element 169 of expandable assembly 160 can comprise one or more ablation elements, such as those described herein. In some embodiments, functional element 169 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 and expandable assembly 160 can be used to ablate target tissue TT. EDU 250 or another component of system 10 can be configured to deliver RF or other energy to any functional element 139 and/or 169. System 10 can include ground pad 70, such as a standard RF energy delivery ground pad typically placed on the patient's back, such that EDU 250 can supply RF energy to a functional element 139 and/or 169 and/or any other electrodes of system 10 in monopolar, bipolar and/or combined monopolar-bipolar energy delivery modes.

In some embodiments, functional element 139 of expandable assembly 130 and/or functional element 169 of expandable assembly 160 comprises an abrasive element configured for abrading target tissue, such as an abrasive element attached to a balloon or expandable cage.

In some embodiments, expandable assembly 160 is further configured to perform at least one non-tissue expanding function. In some embodiments, expandable assembly 160 is configured to ablate tissue, as described hereabove. Alternatively or additionally, expandable assembly 160 and/or expandable assembly 130 can be configured to occlude or partially occlude a lumen surrounded by tissue (as described hereabove), such as a lumen of the GI tract to be occluded during an insufflation procedure, also as described hereabove. Expandable assembly 130 and/or expandable assembly 160 can be configured to manipulate tissue, such as to linearize and/or distend GI tissue by frictionally engaging (e.g. when expanded) and applying forces to the tissue (e.g. by advancing and/or retracting shaft 110a and/or 110b). In some embodiments, one or more expandable assemblies 130 and/or expandable assemblies 160 can perform a function selected from the group consisting of: linearizing curvilinear tissue; distending tissue; expanding tissue; occluding a body lumen; and combinations of these. Expandable assembly 130 and/or expandable assembly 160 can be configured to test and/or diagnose tissue, such as when expandable assembly 130 and/or expandable assembly 160 is used to measure a diameter of tubular tissue into which it has been inserted. Diameter measurements can be performed in various ways, including but not limited to: injection of a radiopaque fluid into expandable assembly 130 and/or expandable assembly 160 and fluoroscopic measurement of the injected fluid; controlled inflation of expandable assembly 130 and/or expandable assembly 160 to a pressure whose level corresponds to a luminal diameter; and combinations of these. In some embodiments, device 100 includes an expandable assembly that can be expanded with one or more control rods (e.g. one or more control rods of conduit 132), such as to perform a diametric measurement of tubular tissue by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device used to perform a diameter measurement, such as sizing device 30 shown. Sizing device 30 can be of similar construction and arrangement to device 30 described hereabove in reference to FIG. 1. One or more energy delivery or other ablation parameters can be adjusted based on the measured diameter of target tissue TT and/or a target tissue segment.

Treatment element 135 can be configured to treat various thicknesses of GI tissue, such as at least the innermost 500 microns of duodenal tissue, or at least the innermost 1 mm of duodenal tissue. In some embodiments, treatment element 135 can be configured to ablate or otherwise treat a thickness of at least 600 microns, at least 1 mm or at least 1.25 mm, such as when treating the mucosa of the stomach. Treatment element 135 can be configured to treat a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or expandable assembly 160 are configured to be in a relatively rigid state, such as during treatment of target tissue TT.

Treatment element 135 and/or other treatment elements of the present inventive concepts can be arranged in an array of elements, such as a circumferential or linear array of elements. The circumferential array can comprise a partial circumferential array of treatment elements 135, such as an array covering approximately 45° to 300° of circumferential area. Partial circumferential arrays of treatment elements 135 can treat a first target tissue segment and a second target tissue segment in two sequential steps, where the array is rotated between treatments (e.g. energy deliveries). The circumferential array can comprise a full 360° array of treatment elements 135, such that a full circumferential volume of target tissue TT can be treated in single or multiple treatments (e.g. energy deliveries) that do not require repositioning of expandable assembly 130. In some embodiments, less than 360° of tubular tissue is treated, such as by treating a circumferential portion of tissue comprising less than or equal to a 350°, or between 300° and 350°, such as to prevent a full circumferential scar from being created.

Two or more treatment elements 135 can be arranged in a helical array. In some embodiments, at least three, four or five treatment elements 135 independently treat target tissue, in similar or dissimilar treatments (e.g. similar or dissimilar amounts of energy, provided simultaneously and/or sequentially by EDU 250).

In some embodiments, console 200, EDU 250 and/or another device or component of system 10 provides electrical or other energy to a component of device 100, such as electrical energy provided to a heating coil in a distal portion of device 100, now shown but typically connected to one or more wires of conduit 132 that travel proximally through shaft 110a to handle 102. Console 200, EDU 250 and/or another device or component of system 10 can provide energy such as electrical energy to one or more functional elements 139 and/or 169 such as when a functional element 139 and/or 169 comprises a transducer or other powered component.

In some embodiments, treatment element 135 comprises one or more treatment elements that are constructed and arranged to treat the entire amount of tissue to be treated ("desired treatment area") with a single energy delivery and/or at least without having to reposition device 100. In these embodiments, treatment element 135 can comprise an array of treatment elements positioned along substantially the entire desired treatment area of the target tissue, or treatment element 135 can comprise one or more treatment elements configured to rotate and/or translate along substantially the entire desired treatment area of tissue. Treatment element 135 and/or other tissue treatment elements of the present inventive concepts can be configured to treat at least 25% of the desired treatment area of the duodenum simultaneously and/or without having to reposition device 100. Alternatively, treatment element 135 and/or other ablation elements of the present inventive concepts can be configured to treat a first portion of the desired treatment area followed by a second portion of the desired treatment area. The first and second treated tissue segments can be overlapping and they can have non-parallel central axes (e.g. tissue segments in a curved portion of the duodenum). Three or more target tissue segments can be treated, such as to cumulatively ablate at least 10% or at least 25% of the duodenal mucosa (e.g. at least 10% or 25% of the duodenal mucosa distal to the ampulla of Vater).

System 10 can be configured to ablate or otherwise treat target tissue TT, such as duodenal mucosal tissue, while avoiding damaging non-target tissue, such as the GI adventitia. Target tissue TT can include at least a portion of safety-margin tissue comprising tissue whose ablation causes minimal or no adverse effect to the patient, such as sub-mucosal tissue of the GI tract. Target tissue TT can comprise one or more portions of tissue that are treated simultaneously or sequentially. In some embodiments, the target tissue TT comprises at least 10% or at least 25% of the duodenal mucosa distal to the ampulla of Vater. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 50 can be a standard endoscope, such as a standard GI endoscope, or a customized endoscope, such as an endoscope including sensor 53 configured to provide information related to the tissue expansion and/or tissue treatment of the present inventive concepts. Endoscope 50 can include camera 52, such as a visible light, ultrasound and/or other visualization device used by the operator of system 10 prior to, during and/or after the expansion and/or treatment of target tissue TT, such as during insertion and/or removal of endoscope 50 and/or shafts 110a and 110b of device 100. Camera 52 can provide direct visualization of internal body spaces and tissue, such as the internal organs of the GI tract. Endoscope 50 can be coupled with or otherwise include a guidewire, e.g. guidewire 60, such as to allow insertion of endoscope 50 into the jejunum and/or advancement of device 100. Device 100 can be constructed and arranged such that endoscope 50 can be advanced within 5 cm of expandable assembly 130 and/or expandable assembly 160.

System 10 can be constructed and arranged to perform insufflation of a body lumen, such as insufflation of a segment of the GI tract. The body lumen can be pressurized, such as by using one or more standard insufflation techniques. Insufflation fluid can be introduced through second lumen 54 of endoscope 50. Second lumen 54 travels proximally and connects to a source of insufflation liquid and/or gas, such as console 200, and typically a source of air, carbon dioxide, water and/or saline. Alternatively or additionally, insufflation fluid can be delivered by device 100, such as through shaft 110a and/or 110b, and/or through a port in expandable assembly 130 and/or expandable assembly 160, such as when an associated functional element 139 and/or 169, respectively comprises a fluid delivery port attached to a source of insufflation liquid and/or gas (e.g. provided by console 200). Alternatively or additionally, a separate device configured to be inserted through endoscope 50 and/or to be positioned alongside endoscope 50, can have one or more lumens configured to deliver the insufflation fluid. System 10 can include one or more occlusive elements and/or devices, such as expandable assembly 130, expandable assembly 160, occlusive element 193 of FIG. 5 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Console 200 can be configured to remove fluid from a body lumen such as a segment of the GI tract. Removed fluids include but are not limited to: tissue expansion fluid; ablative fluid; condensate of delivered ablative fluid; insufflation fluids; excess bodily fluids; chyme; digestive fluids; gas; and combinations of these. Fluids can be removed prior to, during and/or after expansion of target tissue TT by one or more fluid delivery elements 168 and/or treatment of target tissue TT by treatment element 135. Treatment element 135, fluid delivery element 168, a functional element 139 and/or a functional element 169 can be constructed and arranged to remove fluid from a body lumen. Console 200 can be configured to apply a vacuum (e.g. suction), such as to remove fluid via at least one treatment element 135, fluid delivery element 168, an outflow drain, or other fluid extraction port of system 10. In some embodiments, extracted fluids are recycled, such as for subsequent delivery by at least one treatment element 135 and/or fluid delivery element 168 to tissue.

Console 200 can be configured to deliver one or more gases (e.g. carbon dioxide, nitrogen, nitrous oxide and/or air) to at least one treatment element 135, fluid delivery element 168 and/or another gas delivering component of system 10. In some embodiments, at least one treatment element 135 and/or fluid delivery element 168 comprises a gas jet nozzle configured to deliver gas to target tissue, such as a gas than has been processed to remove moisture or otherwise is relatively dry (e.g. less than the dew point of air, or at a relative humidity less than 20% or less than 10%). In some embodiments, system 10 is configured to deliver gas to cause agitation of an ablative fluid previously delivered within a body lumen. System 10 can be configured to deliver relatively dry or other gas to move ablative fluid in a body lumen. The delivered gas can comprise a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or equal to 10 seconds, or less than or equal to 5 seconds. In some embodiments, system 10 is configured to deliver gas at a temperature at or above 42° C., such as to remove moisture or otherwise dry a tissue wall of the GI tract. System 10 can be configured to deliver carbon dioxide gas.

Functional elements 139 and/or 169 can comprise a sensor. In some embodiments, functional element 139 and/or 169, sensor 53 and/or another sensor of system 10 can comprise a sensor selected from the group consisting of: temperature sensor such as a thermocouple, thermistor, resistance temperature detector or an optical temperature sensor; strain gauge; impedance sensor such as a tissue impedance sensor; pressure sensor; blood sensor; optical sensor such as a light sensor; sound sensor such as an ultrasound sensor; electromagnetic sensor such as an electromagnetic field sensor; visual sensor; and combinations of these. The sensors can be configured to provide information to one or more components of system 10, such as to controller 210 and/or console 200, such as to monitor the expansion and/or treatment of target tissue TT and/or to expand and/or treat target tissue TT in a closed loop configuration. Fluid delivery by fluid source 220 and/or energy delivery from EDU 250 can be initiated, regulated, modified, stopped and/or otherwise controlled based on one or more sensor readings.

Controller 210 can comprise one or more algorithms 211, which can be constructed and arranged to automatically and/or manually control and/or monitor one or more devices, assemblies and/or components of system 10. Algorithm 211 of controller 210 can be configured to determine one or more tissue expansion and/or tissue treatment parameters. In some embodiments, algorithm 211 processes one or more functional element 139 and/or 169 sensor signals to modify one or more of: volume of tissue expansion fluid delivered; rate of tissue expansion fluid delivery; temperature of tissue expansion fluid delivery; amount of ablative fluid delivered; rate of ablative fluid delivery; energy delivered; power of energy delivered; voltage of energy delivered; current of energy delivered; and/or temperature of ablative fluid or energy delivered. Expandable assembly 130 can deliver energy to a surface of tissue, an "delivery zone", which is a subset of the target tissue TT treated by that energy delivery (i.e. due to the conduction of heat or other energy to neighboring tissue). Algorithm 211 can comprise an algorithm configured to determine a delivery zone parameter such as a delivery zone parameter selected from the group consisting of: anatomical location of a delivery zone; size of delivery zone; percentage of delivery zone to receive energy; type of energy to be delivered to a delivery zone; amount of energy to be delivered to a delivery zone; and combinations of these. Information regarding the delivery zone parameter can be provided to an operator of system 10. This information can be employed to set a delivery zone parameter, assist the operator in determining the completion status of the procedure (e.g. determining when the procedure is sufficiently complete) and/or to advise the operator to continue to complete a pre-specified area or volume of target tissue. The total area of treatment or number of delivery zones or number of treatments during a particular procedure (any of which can be employed in algorithm 211) can be defined by patient clinical or demographic data.

Functional elements 139 and/or 169 can comprise a gravimetric sensor. In some embodiments, functional element 139 comprises an accelerometer or other sensor configured to provide a signal representing the orientation of expandable assembly 130 and/or treatment element 135 as it relates to the force of earth's gravity. In embodiments in which treatment element 135 delivers ablative fluid to target tissue TT, the signal provided by functional element 139 can provide information for manual and/or automated control of ablative fluid delivery direction. In some embodiments, gravimetric orientation of device 100 is provided to an operator, such as via a screen on user interface 205 of console 200 and/or user interface 105 of handle 102. In some embodiments, the signal from functional element 139 is recorded by controller 210, such as to adjust a spray pattern delivered by expandable assembly 130 and/or treatment element 135, such as via algorithm 211. Based on a signal from functional element 139, treatment element 135 and/or shaft 110a can be positioned to deliver ablative fluid in upward and/or side-ways (i.e. horizontal) directions, such as to allow delivered fluid to flow across the walls of a lumen in a downward direction. Controller 210 and/or algorithm 211 can be configured to adjust the flow pattern of ablative fluid delivery by adjusting the rotation and/or translation of expandable assembly 130 (e.g. by creating an asymmetric movement). Controller 210 can be configured to adjust the flow pattern of ablative fluid delivery by adjusting which of multiple treatment elements 135 deliver ablative fluid (e.g. by turning on one or more electronic fluid valves) or by adjusting a nozzle direction or nozzle flow path geometry of treatment element 135 (e.g. when treatment element 135 comprises a rotatable nozzle and/or a nozzle with an adjustable orifice). In some embodiments, controller 210 utilizes a signal from functional element 139 to manipulate one or more treatment elements 135 to deliver fluid in a relatively upward direction. In some embodiments, system 10 includes a fluid removal element as described hereinabove, such as a treatment element 135 configured to remove fluid by an outflow drain, and the fluid removal element is gravimetrically oriented by a signal provided by functional element 139.

Functional elements 139 and/or 169 can comprise a chemical detection sensor, such as a chemical detection sensor to confirm proper apposition of expandable assembly 130 and/or expandable assembly 160. In this configuration, a chemical sensor such as a carbon dioxide sensor can be placed distal to expandable assembly 130 and/or expandable assembly 160, and a fluid such as carbon dioxide gas can be introduced proximal to the expandable assembly 130 and/or expandable assembly 160. Detection of the introduced fluid by a functional element 139 and/or 169 can indicate inadequate apposition of expandable assembly 130 and/or expandable assembly 160, respectively. Readjustment to achieve sufficient apposition can prevent inadequate expansion and/or treatment of target tissue TT (e.g. inadequate delivery of fluid and/or inadequate transfer of energy) and/or prevent inadequate measurement, modification, manipulation and/or diagnosis of target tissue TT.

Functional element 139, functional element 169, sensor 53 and/or another sensor of system 10 can be a sensor configured to provide information related to the tissue treatment and/or expansion performed by expandable assembly 130 and/or expandable assembly 160, respectively, such as a visual sensor mounted to expandable assembly 130 and/or expandable assembly 160 that is configured to differentiate tissue types that are proximate expandable assembly 130 and/or expandable assembly 160. In some embodiments, system 10 is constructed and arranged to differentiate mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy provided by EDU 250 is based on one or more signals from the visible sensor, such as a sensor providing a signal correlating to tissue color wherein the energy delivered is modified based on a tissue color change and/or tissue expansion injectate 221 comprise a visible dye or other visualizable marker used to assess tissue expansion.

One or more functional elements 139 and/or 169 can comprise a temperature sensor configured to monitor the temperature of treatment provided by expandable assembly 130 and/or expandable assembly 160 and/or tissue proximate expandable assembly 130 and/or expandable assembly 160. Functional elements 139 and/or 169 can each comprise multiple temperature sensors, such as multiple temperature sensors positioned on expandable assembly 130 and/or expandable assembly 160, respectively, with a spacing of at least one sensor per square centimeter. Energy delivered by EDU 250 can be based on signals recorded by the multiple temperature sensors.

Fluid delivered by fluid source 220 (e.g. injectate 221) can be based on signals recorded by one or functional elements 139 and/or 169. One or more functional elements 139 and/or 169 can comprise one or more sensors, such as one or more of: a visual sensor such as a camera; a temperature sensor; a pH sensor; an ultrasound transducer; and combinations of these. In some embodiments, injectate 221 comprises one or more dyes (e.g. visible dye, ultrasonically visualizable material and/or radiopaque dye), and functional element 139 and/or 169 comprises one or more cameras (e.g. visible light camera, ultrasound imager and/or x-ray camera) that image the tissue being expanded and produce a signal correlating to the amount of tissue expansion based on the amount of dye present in the expanded tissue. In some embodiments, injectate 221 is delivered at a temperature different than the temperature of the tissue being expanded (e.g. above or below body temperature), and functional element 139 and/or 169 comprises a sensor that measures the temperature proximate the tissue being expanded and produces a signal correlating to the amount of tissue expansion based on the measured temperature (e.g. based on the difference between the measured temperature and body temperature). In some embodiments, injectate 221 comprises a pH different than the pH of the tissue being expanded, and functional element 139 and/or 169 comprises a sensor that measures the pH proximate the tissue being expanded and produces a signal correlating to the amount of tissue expansion based on the measured pH (e.g. based on a change in the measured pH that occurs during tissue expansion). In some embodiments, functional element 139 and/or 169 comprises an ultrasound transducer directed at the tissue being expanded and produces a signal correlating to the amount of tissue expansion based on an analysis of an image of the expanding tissue produced by the ultrasound transducer.

A functional element 139 and/or 169 can comprise a transducer. In these and other embodiments, functional element 139, functional element 169 and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; a fluid agitating element; and combinations of these.

In some embodiments, console 200 and/or another device of component of system 10 is configured to deliver a visualizable material, such as when injectate 221 and/or another fluid of system 10 includes a visualizable material delivered to one or more fluid delivery elements 168 and/or one or more treatment elements 135. In some embodiments, visualizable material is delivered by fluid delivery element 168 onto and/or beneath the surface of tissue, to assist in the tissue expansion of target tissue TT, such as to assess the status of tissue expansion as described hereabove. In some embodiments, visualizable material is delivered by treatment element 135 onto and/or beneath the surface of tissue, to assist in the treatment of target tissue TT, such as to assess the status of tissue ablation, such as via a camera-based functional element 139. In some embodiments, the visualizable material is selected from the group consisting of: colored dye; radiopaque agent; ultrasonically visible material; magnetically visible material; and combinations of these. An imaging device of system 10, such as a camera based functional element 139 and/or 169 and/or imaging device 410 described herebelow, can be used to create an image of the visualizable material during and/or after delivery of the visualizable material.

In some embodiments, console 200 or another device of component of system 10 is configured to deliver abrasive particles, such as abrasive particles delivered to one or more treatment elements 135 and/or fluid delivery elements 168. In some embodiments, visualizable material is also delivered by console 200 to assist in the treatment of tissue, such as to improve cellular disruption caused by a mechanical abrasion treatment by visualizing the treatment in real time.

In some embodiments, EDU 250 is configured to deliver at least RF energy, and system 10 includes ground pad 70 configured to be attached to the patient (e.g. on the back of the patient), such that RF energy can be delivered in monopolar delivery mode to one or more electrode-based treatment elements 135 of device 100 or to one or more electrodes of another device of system 10 (e.g. second device 100'). Alternatively or additionally, EDU 250 can be configured to deliver energy in a bipolar RF mode, such as bipolar energy delivered between any two electrode-based treatment elements 135 of device 100 or between any other two electrodes of another treatment device of system 10. Alternatively or additionally, EDU 250 can be configured to deliver energy in a combined monopolar-bipolar mode.

EDU 250 can be configured to deliver RF and/or other forms of energy to one or more treatment elements 135 of expandable assembly 130 and/or a treatment element of expandable assembly 160. In some embodiments, EDU 250 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 250, such as in a closed loop fashion based on one or more signals provided by a sensor-based functional element 139 and/or 169. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery. Alternatively or additionally, one or more energy delivery parameters can be varied between a first treatment of target tissue and a second treatment of target tissue, for example a first treatment performed during a first clinical procedure and a second treatment performed during a second clinical procedure, such as when the second treatment is performed at least twenty-four hours after the first treatment.

As described hereabove, console 200 typically includes one or more fluid pumps, such as one or more peristaltic, displacement and/or other fluid pumps; as well as one or more heat exchangers and/or other fluid heating elements internal and/or external to device 100. EDU 250 and/or another component of console 200 or system 10 can be configured to rapidly deliver and/or withdraw fluid to and/or from expandable assembly 130 and/or expandable assembly 160 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, console 200 is configured to deliver fluid, such as a liquid, at a flow rate of at least 500 ml/min, or at least 750 ml/min. A pump and/or vacuum source can be configured to continuously exchange hot fluid and/or to perform a negative pressure priming event to remove fluid from one or more fluid pathways of device 100. Console 200, device 100 and/or device 20 can include one or more valves in the fluid delivery and/or fluid withdrawal pathways or one or more other valves in the fluid pathway within expandable assembly 130 and/or expandable assembly 160. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Console 200 can be configured to rapidly inflate and/or deflate expandable assembly 130 and/or expandable assembly 160. Console 200 can be configured to purge the fluid pathways of device 100 and/or device 20 with a gas such as air, such as to remove cold and/or hot fluid from the devices and/or to remove gas bubbles from the devices.

User interface 205 of console 200 and/or user interface 105 of handle 102 can include a graphical user interface configured to allow one or more operators of system 10 to perform one or more functions such as entering of one or more system input parameters and visualizing and/or recording of one or more system output parameters. User interface 205 and/or user interface 105 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: volume of tissue expanding fluid to be delivered; flow rate of tissue expanding fluid; temperature of tissue expanding fluid; type of tissue expanding fluid to be delivered; temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or pen-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Console 200, device 100 and/or one or more other components of system 10 can include an electronics module, such as an electronics module including a processor, memory, software, and the like. User interface 205 and/or user interface 105 are typically configured to allow an operator to initiate, regulate, modify, stop and/or otherwise control expansion and/or treatment of target tissue TT by the various components of system 10, such as by controlling fluid source 220 and/or EDU 250. User interface 205 and/or user interface 105 can be configured to modify one or more tissue treatment parameters, such as a parameter selected from the group consisting of: volume of tissue expanding fluid to be delivered; flow rate of tissue expanding fluid; temperature of tissue expanding fluid; type of tissue expanding fluid to be delivered; temperature of an ablative fluid to be delivered directly to tissue or to an expandable reservoir such as a balloon; type of ablative fluid to be delivered; rate of ablative fluid to be delivered; volume of ablative fluid to be delivered; pulse width modulation on-time and/or off-time; a time division multiplexing parameter; and combinations of these. System 10 can be configured for manual control, so that the operator first initiates the tissue treatment, then allows the treatment element 135 and/or another associated treatment element to treat the target tissue TT for some time period, after which the operator terminates the treatment.

System 10 can be configured to treat target tissue TT in constant, varied, continuous and discontinuous energy delivery or other treatment delivery profiles. Pulse width modulation and/or time division multiplexing (TDM) can be incorporated to achieve precision of an ablative treatment, such as to ensure ablation of target tissue TT while leaving non-target tissue intact.

In some embodiments, where system 10 is configured to perform hot fluid ablation, controller 210 can be configured to adjust the temperature, flow rate and/or pressure of fluid delivered to an expandable reservoir, such as when expandable assembly 130 and/or expandable assembly 160 comprise a balloon. Controller 210 can be configured to receive commands from user interface 205 or user interface 105 of device 100. In some embodiments, controller 210 receives wireless (e.g. Bluetooth) commands from user device 100 via user interface 105. Controller 210 can be configured to initiate insufflation and/or to adjust insufflation pressure. Controller 210 can be configured to deliver energy or otherwise treat target tissue in a closed-loop fashion, such as by modifying one or more tissue treatment parameters based on signals from one or more sensors of system 10, such as those described hereabove. Controller 210 can be programmable such as to allow an operator to store predetermined system settings for future use. Controller 210 can comprise memory configured to store one or more system or patient parameters.

Controller 210 can comprise an impedance monitoring assembly, such as an impedance monitoring assembly that receives impedance information from one or both of functional element 139 of expandable assembly 130 and/or functional element 169 of expandable assembly 160. EDU 250 can deliver RF energy to one or more electrode-based treatment elements of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Console 200 can be configured to deliver a fluid to tissue and/or a component and/or assembly of system 10, such as to warm and/or cool the tissue, component and/or assembly. Console 200 can be configured to deliver a cooling fluid to a luminal wall such as the duodenal wall, such as prior to a delivery of energy, during a delivery of energy and/or after a delivery of energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between treatment of a first portion of target tissue and a second portion of target tissue (e.g. to the same or different tissue), such as to remove residual heat remaining after the first treatment. The cooling fluid can be delivered through functional element 139 of expandable assembly 130 and/or functional element 169 of expandable assembly 160, such as when functional elements 139 and/or 169 comprise a fluid delivery element such as a nozzle, an exit hole, a slit, or a permeable membrane. The cooling fluid can be supplied to a location within expandable assembly 130 and/or expandable assembly 160, such as when expandable assembly 130 and/or expandable assembly 160 comprises a balloon or other expandable reservoir configured to contact tissue. Alternatively or additionally, console 200 can be fluidly attached to another component of device 100 and/or system 10, the attached component not shown but configured to deliver fluid to tissue and/or a component of system 10 such as to add and/or absorb heat. Console 200 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

In some embodiments, console 200 includes a desiccant and/or drying assembly configured to dehydrate or otherwise remove moisture from one or more delivered gases prior to their delivery by device 100, device 20 and/or another device of system 10.

In some embodiments, system 10 and/or device 100 are constructed and arranged to perform a fractional treatment of tissue. Device 100 can be constructed and arranged to treat target tissue with a fractional delivery of RF energy, such as monopolar and/or bipolar RF energy delivered from an array of electrodes positioned on an expandable element. In some embodiments, device 100 is configured as a laser or other light energy delivery device constructed and arranged to provide a fractional energy delivery to target tissue. In some embodiments, device 100 is configured to vaporize at least a portion of target tissue.

As described hereabove, system 10 can include one or more additional tissue expanding and/or tissue treating devices, such as treatment device 100'. Device 100' and/or other treatment devices of the present inventive concepts can be configured to treat and/or expand target tissue TT in the same clinical procedure, or in a clinical procedure performed at least twenty-four hours after the first clinical procedure. Second device 100' can be of similar or dissimilar construction to device 100. In some embodiments, second device 100' comprises an expandable assembly with a different diameter than expandable assembly 130 of device 100. In some embodiments, second device 100' comprises a treatment element with a different construction and arrangement than treatment element 135 of device 100. In some embodiments, second device 100' comprises a device selected from the group consisting of: injectate delivery device; tissue expansion device; hot fluid filled balloon device; RF energy delivery device; vapor ablation device; cryoablation device; laser ablation device; ultrasound ablation device; mechanical abrasion device; and combinations of these. Second device 100' can comprise at least one fluid delivery element selected from the group consisting of: needle; fluid jet; iontophoretic element; and combinations of these. Second device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 110a and/or 110b. Imaging device 410 can be inserted through a separate working channel of endoscope 50, such as lumen 51. In one embodiment, imaging device 410 is an ultrasound transducer connected to a shaft, not shown but surrounded by shaft 110a and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these. Image and other information provided by imaging device 410 can be provided to an operator of system 10 and/or used by a component of system 10, such as controller 210, to automatically or semi-automatically adjust one or more system parameters such as one or more energy delivery parameters.

System 10 can further include protective element 191, configured to be positioned proximate tissue to prevent damage to certain tissue during tissue ablative fluid delivery, other energy delivery, tissue expansion and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 50 and/or another elongate device such that protective element 191 can be placed over or otherwise positioned to protect non-target tissue, such as tissue selected from the group consisting of: ampulla of Vater; bile duct; pancreas; pylorus; muscularis externae; serosa; and combinations of these. In some embodiments, protective element 191 is placed prior to treatment of at least a portion of target tissue TT, and removed in the same clinical procedure. In other embodiments, protective element 191 is implanted in a first clinical procedure, and removed in a second clinical procedure, such as a second clinical procedure as described herein. In some embodiments, protective element 191 is evacuated from the body by the patient's digestive system. System 10 can be configured to identify non-target tissue, such as via a camera used to identify the ampulla of Vater.

System 10 can be configured to prevent excessive or otherwise undesired distension of the duodenum such as distension that could cause tearing of the serosa. In some embodiments, system 10 is configured such that all tissue contacting components and/or fluids delivered by system 10 maintain forces applied on a GI wall below 2.0 psi, such as less than 1.2 psi. System 10 can be configured to avoid or otherwise minimize damage to the muscularis layer of the GI tract, such as by controlling pressure of target tissue treatment (e.g. via controlling expansion force of expandable assembly 130 and or expandable assembly 160) and/or by otherwise minimizing trauma imparted on any tissue by one or more components of system 10.

System 10 can further include one or more pharmaceutical and/or other agents 420, such as an agent configured for systemic and/or local delivery to a patient. Agents 420 can be delivered pre-procedurally, peri-procedurally and/or post-procedurally. Agents 420 can comprise one or more imaging agents, such an imaging agent used with imaging device 410. Agents 420 can be one or more pharmaceutical or agents configured to improve healing, such as agents selected from the group consisting of: antibiotics; steroids; mucosal cytoprotective agents such as sucralfate, proton pump inhibitors and/or other acid blocking drugs; and combinations of these. Alternative or in addition to agents 420, pre-procedural and/or post-procedural diets can be employed. For example, pre-procedural diets can include food intake that is low in carbohydrates and/or low in calories, and post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of: a stent; a sleeve; and/or a drug delivery device such as a coated stent, a coated sleeve and/or an implanted pump. Implant 192 can be inserted into the patient and remain implanted for a period of at least one month, at least 6 months or at least 1 year. In some embodiments, a first clinical procedure is performed treating target tissue, and a subsequent second clinical procedure is performed, as is described herein. In these two clinical procedure embodiments, a device can be implanted in the first clinical procedure, and removed in the second clinical procedure.

System 10 can include sizing device 30 which can be constructed and arranged to be placed into one or more locations of the gastrointestinal tract or other internal location of the patient and measure the size or other geometric parameter of tissue. In some embodiments, sizing device 30 has a similar construction and arrangement to sizing device 30 of FIG. 1. In some embodiments, sizing device 30 comprises a balloon, expandable cage or other sizing element constructed and arranged to measure the inner surface diameter of a tubular tissue such as duodenal and/or jejunal tissue. A diameter measurement can be performed by inflating a balloon of sizing device 30 to one or more predetermined pressures, or pressure profiles, and performing a visualization procedure or other procedure to determine balloon diameter. Alternatively or additionally, a balloon can be filled with a fluid and one or more of fluid volume or fluid pressure is measured to determine balloon diameter and subsequently diameter of tubular tissue proximate the balloon. In some embodiments, subsequent selection (e.g. size selection) and/or expansion diameter (e.g. sized for apposition) of expandable assembly 130, expandable assembly 160 and/or a treatment assembly of treatment device 100' can be determined using these tissue geometry measurements. Alternatively or additionally, an expandable element such as a balloon or cage can comprise two or more electrodes configured to provide a tissue impedance measurement whose value can be correlated to a level of apposition of the expandable element, and whose expanded diameter (e.g. visually measured) subsequently correlated to a diameter of tubular tissue proximate the expandable element. In some embodiments, expandable assembly 130 and/or expandable assembly 160 comprise sizing device 30, such as when expandable assembly 130 and/or expandable assembly 160 comprise a balloon or other sizing element used to measure a diameter of the inner surface of tubular tissue.

System 10 can be constructed and arranged to control one or more system parameters, such as controlling one or more system parameters prior to, during or after the delivery of a thermal dose of energy, during a priming procedure, during a sizing procedure and/or during a tissue expansion procedure. System 10 can be constructed and arranged to control a system parameter selected from the group consisting of: a priming procedure parameter such as priming temperature or priming duration; a target tissue treatment parameter such as target tissue temperature or target tissue treatment duration; fluid flow rate such as treatment fluid flow rate; a pressure parameter such as a treatment element pressure maintained during treatment of target tissue; a treatment element diameter such as a treatment element diameter maintained during treatment of target tissue; and combinations thereof. System 10 can be constructed and arranged to control the size of an expandable reservoir, such as by controlling the diameter of expandable assembly 130, expandable assembly 160 and/or another expandable reservoir or assembly as described herein. In some embodiments, a user of system 10 selects a size of an expandable reservoir, such as by selecting the size from a range of available sizes of expandable assembly 130 and/or expandable assembly 160 provided to the user in a kit.

Any of the components of system 10 can include a coating, such as a lubricious coating. In some embodiments, expandable assembly 130, expandable assembly 160 and/or other radially expandable elements such as balloons include a lubricious or other material property modifying coating. In some embodiments, a radially expandable and radially compactable expandable assembly 130 and/or expandable assembly 160 comprise a hydrophilic coating, for example configured to disperse or otherwise move an ablative fluid.

Each of the components and/or devices of system 10 can be removably attached to another component, particularly device 100, device 20, console 200, EDU 250, motion transfer assembly 260, ground pad 70, endoscope 50 and/or second device 100'. Typical attachment means include but are not limited to mechanical or electromechanical connectors providing an electrical, optical and/or fluidic connection between the attached components.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth below not be construed as being order-specific unless such order specificity is expressly stated in the claim.

What is claimed is:

1. A system for modifying tissue to provide a therapeutic benefit to a patient, the system comprising:
    a tissue treatment device (100) for treating target tissue comprising:
        a tissue treatment element constructed and arranged to apply a tissue modifying agent to the target tissue, wherein the tissue treatment element is configured to expand prior to the delivery of the tissue modifying agent; and
        a shaft (110) with a proximal end and a distal portion and a lumen (116), wherein the tissue treatment element is positioned on the distal portion of the shaft (110);
        a tissue modifying agent delivery unit configured to deliver the tissue modifying agent to the tissue treatment element through the lumen (116); and
        one or more deployable occluding elements (193) for preventing migration of the tissue modifying agent to non-target tissue;
        wherein the one or more deployable occluding elements (193) are positioned within the lumen;
        a translatable push rod (138) configured to be advanced to deploy the one or more deployable occluding elements (193) from a distal end of the lumen (116);
    wherein the target tissue comprises duodenal mucosal tissue, and wherein the system is configured to modify the target tissue to provide the therapeutic benefit.

2. The system according to claim 1, wherein the system is configured to treat a cumulative length of duodenal mucosa of at least 3.4 cm to achieve the therapeutic benefit.

3. The system according to claim 1, wherein the system is configured to treat at least one of a disease or disorder selected from the group consisting of: diabetes; pre-diabetes; impaired glucose tolerance; insulin resistance; obesity or otherwise being overweight; a metabolic disorder; a metabolic disease; and combinations thereof.

4. The system according to claim 1, wherein the target tissue comprises duodenal mucosa located distal to the ampulla of Vater.

5. The system according to claim 1, wherein the tissue treatment device (100) is configured to be inserted through an endoscope.

6. The system according to claim 1, wherein the tissue treatment element is configured to expand when contacted with a fluid.

7. The system according to claim 6, wherein the contacting fluid configured to cause the expansion comprises the tissue modifying agent.

8. The system according to claim 1, wherein the tissue treatment element is configured to be radially compressed and captured within an endoscope.

9. The system according to claim 1, wherein the tissue treatment element comprises a sponge material.

10. The system according to claim 9, wherein the sponge material is selected from the group consisting of: a natural sponge material; a synthetic sponge material; a foamed polyurethane; a polyvinyl alcohol (PVA) sponge; a hydrogel; a super-absorbent polymer; and combinations thereof.

11. The system according to claim 1, wherein the tissue treatment element comprises a balloon.

12. The system according to claim 11, wherein the balloon comprises a permeable balloon, and wherein the tissue modifying agent is configured to be delivered to the target tissue through the permeable balloon.

13. The system according to claim 1, wherein the tissue modifying agent is configured to cause necrosis of the target tissue.

14. The system according to claim 13, wherein the tissue modifying agent is selected from the group consisting of: a chemical peeling agent; a mild acid; glycolic acid; trichloroacetic acid; a mild base; phenol; retinoic acid; and combinations thereof.

15. The system according to claim 1, further comprising a neutralizing agent configured to stop and/or reverse the effects of the tissue modifying agent.

16. The system according to claim 1, further comprising at least one deployable marker, wherein the target tissue comprises tissue locatable by the at least one deployable marker.

17. The system according to claim 1, wherein the one or more deployable occluding elements is/are biodegradable and configured to evacuate the body via the body's natural digestive system.

18. The system according to claim 1, wherein the one or more deployable occluding elements is/are arranged to be removed via a grasping element deployed through an endoscope.

* * * * *